(12) United States Patent
Hogenhaug

(10) Patent No.: US 7,250,398 B2
(45) Date of Patent: Jul. 31, 2007

(54) SYNTHETIC ANTIMICROBIAL POLYPEPTIDES

(75) Inventor: Hans-Henrik Kristensen Hogenhaug, Holte (DK)

(73) Assignee: Novozymes A/S, Baqsvaerd (DK)

( * ) Notice: Subject to any disclaimer, the term of this patent is extended or adjusted under 35 U.S.C. 154(b) by 0 days.

(21) Appl. No.: 11/030,232

(22) Filed: Jan. 6, 2005

(65) Prior Publication Data

US 2005/0239709 A1 Oct. 27, 2005

Related U.S. Application Data

(63) Continuation of application No. PCT/DK04/00606, filed on Sep. 13, 2004.

(60) Provisional application No. 60/546,541, filed on Feb. 20, 2004.

(30) Foreign Application Priority Data

Sep. 12, 2003 (DK) .............................. 2003 01324

(51) Int. Cl.
 A61K 38/16 (2006.01)
 C07K 14/00 (2006.01)
(52) U.S. Cl. ........................................ 514/12; 530/324
(58) Field of Classification Search ..................... None
 See application file for complete search history.

(56) References Cited

FOREIGN PATENT DOCUMENTS

WO    WO 92/22578    12/1992

OTHER PUBLICATIONS

International Search Report received in PCT/DK2004/000606, the PCT counterpart to the instant application (Mar. 23, 2006).
Nidome et al., Journal of Peptide Research, vol. 51, pp. 347-345 (1998).
Raj et al., Biochemistry, vol. 35, pp. 4314-4325 (1996).
Chan et al., The Journal of Biological Chemistry, vol. 273, Part 44, pp. 28978-28995 (1998).
Nidome et al., Chemical Society of Japan, vol. 73, pp. 1397-1402 (2000).
Nidome et al., Journal of Peptide Research, vol. 6, pp. 271-279 (2000).

*Primary Examiner*—Robert A. Wax
(74) *Attorney, Agent, or Firm*—Elias J. Lambiris

(57) ABSTRACT

The present invention relates to polypeptides having antimicrobial activity and polynucleotides having a nucleotide sequence which encodes for the polypeptides. The invention also relates to nucleic acid constructs, vectors, and host cells comprising the nucleic acid constructs as well as methods for producing and using the polypeptides.

20 Claims, No Drawings

```
SEQUENCE LISTING

<160> NUMBER OF SEQ ID NOS: 353

<210> SEQ ID NO 1
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 1

Arg Arg Arg Pro Pro Arg Phe Pro Pro Arg Phe Pro Pro Arg Phe Pro
1               5                   10                  15

Pro Arg Phe Pro Pro Arg Phe Pro Pro Arg Phe
                20                  25

<210> SEQ ID NO 2
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 2

Arg Arg Arg Pro Arg Phe Pro Pro Arg Phe Pro Pro Arg Phe Pro Pro
1               5                   10                  15

Arg Phe Pro Pro Arg Phe Pro Pro Arg Phe Pro
                20                  25

<210> SEQ ID NO 3
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 3

Arg Arg Arg Arg Phe Pro Pro Arg Phe Pro Pro Arg Phe Pro Pro Arg
1               5                   10                  15

Phe Pro Pro Arg Phe Pro Pro Arg Phe Pro Pro
                20                  25
```

<210> SEQ ID NO 4
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 4

Arg Arg Arg Phe Pro Pro Arg Phe Pro Pro Arg Phe Pro Pro Arg Phe
1               5                   10                  15

Pro Pro Arg Phe Pro Pro Arg Phe Pro Pro Arg
            20                  25

<210> SEQ ID NO 5
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 5

Arg Arg Arg Pro Arg Pro Phe Pro Arg Pro Phe Pro Arg Pro Phe Pro
1               5                   10                  15

Arg Pro Phe Pro Arg Pro Phe Pro Arg Pro Phe
            20                  25

<210> SEQ ID NO 6
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 6

Arg Arg Arg Arg Pro Phe Pro Arg Pro Phe Pro Arg Pro Phe Pro Arg
1               5                   10                  15

Pro Phe Pro Arg Pro Phe Pro Arg Pro Phe Pro
            20                  25

<210> SEQ ID NO 7
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 7

Arg Arg Arg Pro Phe Pro Arg Pro Phe Pro Arg Pro Phe Pro Arg Pro
1               5                   10                  15

Phe Pro Arg Pro Phe Pro Arg Pro Phe Pro Arg
            20                  25

<210> SEQ ID NO 8
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 8

Arg Arg Arg Phe Pro Arg Pro Phe Pro Arg Pro Phe Pro Arg Pro Phe
1               5                   10                  15

Pro Arg Pro Phe Pro Arg Pro Phe Pro Arg Pro

```
            20                  25

<210> SEQ ID NO 9
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 9

Arg Arg Arg Pro Pro Phe Arg Pro Pro Phe Arg Pro Pro Phe Arg Pro
1               5                  10                  15

Pro Phe Arg Pro Pro Phe Arg Pro Pro Phe Arg
            20                  25

<210> SEQ ID NO 10
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 10

Arg Arg Arg Pro Phe Arg Pro Pro Phe Arg Pro Pro Phe Arg Pro Pro
1               5                  10                  15

Phe Arg Pro Pro Phe Arg Pro Pro Phe Arg Pro
            20                  25

<210> SEQ ID NO 11
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 11

Arg Arg Arg Phe Arg Pro Pro Phe Arg Pro Pro Phe Arg Pro Pro Phe
1               5                  10                  15

Arg Pro Pro Phe Arg Pro Pro Phe Arg Pro Pro
            20                  25

<210> SEQ ID NO 12
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 12

Arg Arg Arg Arg Pro Pro Phe Arg Pro Pro Phe Arg Pro Pro Phe Arg
1               5                  10                  15

Pro Pro Phe Arg Pro Pro Phe Arg Pro Pro Phe
            20                  25

<210> SEQ ID NO 13
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 13

Arg Arg Arg Pro Pro Arg Phe Pro Pro Arg Phe Pro Pro Arg Phe Pro
1               5                  10                  15
```

```
Pro Arg Phe Pro Pro Arg Phe Pro Pro Arg Phe
            20                  25

<210> SEQ ID NO 14
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 14

Arg Arg Arg Pro Pro Arg Phe Pro Pro Arg Ile Pro Pro Arg Phe Pro
1               5                   10                  15

Pro Arg Leu Pro Pro Arg Ile Pro Pro Arg Leu
            20                  25

<210> SEQ ID NO 15
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 15

Arg Arg Arg Pro Pro Arg Phe Pro Pro Arg Ile Pro Pro Arg Leu Pro
1               5                   10                  15

Pro Arg Val Pro Pro Arg Val Pro Pro Arg Leu
            20                  25

<210> SEQ ID NO 16
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 16

Arg Arg Arg Pro Pro Arg Ile Pro Pro Arg Phe Pro Pro Arg Val Pro
1               5                   10                  15

Pro Arg Phe Pro Pro Arg Val Pro Pro Arg Val
            20                  25

<210> SEQ ID NO 17
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 17

Arg Arg Arg Pro Pro Arg Ile Pro Pro Arg Leu Pro Pro Arg Ile Pro
1               5                   10                  15

Pro Arg Phe Pro Pro Arg Phe Pro Pro Arg Leu
            20                  25

<210> SEQ ID NO 18
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 18

Arg Arg Arg Pro Pro Arg Leu Pro Pro Arg Phe Pro Pro Arg Phe Pro
1               5                   10                  15
```

```
Pro Arg Ile Pro Pro Arg Phe Pro Pro Arg Ile
            20                  25
```

<210> SEQ ID NO 19
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 19

```
Arg Arg Arg Pro Pro Arg Leu Pro Pro Arg Phe Pro Pro Arg Phe Pro
1               5                   10                  15

Pro Arg Ile Pro Pro Arg Phe Pro Pro Arg Ile
            20                  25
```

<210> SEQ ID NO 20
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 20

```
Arg Arg Arg Pro Pro Arg Leu Pro Pro Arg Phe Pro Pro Arg Phe Pro
1               5                   10                  15

Pro Arg Val Pro Pro Arg Phe Pro Pro Arg Val
            20                  25
```

<210> SEQ ID NO 21
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 21

```
Arg Arg Arg Pro Pro Arg Leu Pro Pro Arg Phe Pro Pro Arg Phe Pro
1               5                   10                  15

Pro Arg Val Pro Pro Arg Phe Pro Pro Arg Val
            20                  25
```

<210> SEQ ID NO 22
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 22

```
Arg Arg Arg Pro Pro Arg Leu Pro Pro Arg Phe Pro Pro Arg Phe Pro
1               5                   10                  15

Pro Arg Val Pro Pro Arg Leu Pro Pro Arg Phe
            20                  25
```

<210> SEQ ID NO 23
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 23

```
Arg Arg Arg Pro Pro Arg Leu Pro Pro Arg Phe Pro Pro Arg Phe Pro
```

```
                1               5                  10                 15
Pro Arg Val Pro Pro Arg Val Pro Pro Arg Phe
                20                 25

<210> SEQ ID NO 24
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 24

Arg Arg Arg Pro Pro Arg Leu Pro Pro Arg Phe Pro Pro Arg Phe Pro
1               5                  10                 15
Pro Arg Val Pro Pro Arg Val Pro Pro Arg Phe
                20                 25

<210> SEQ ID NO 25
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 25

Arg Arg Arg Pro Pro Arg Leu Pro Pro Arg Phe Pro Pro Arg Phe Pro
1               5                  10                 15
Pro Arg Val Pro Pro Arg Val Pro Pro Arg Ile
                20                 25

<210> SEQ ID NO 26
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 26

Arg Arg Arg Pro Pro Arg Val Pro Pro Arg Phe Pro Pro Arg Val Pro
1               5                  10                 15
Pro Arg Phe Pro Pro Arg Val Pro Leu Arg Leu
                20                 25

<210> SEQ ID NO 27
<211> LENGTH: 41
<212> TYPE: PRT
<213> ORGANISM: Artificial
<220> FEATURE:
<223> OTHER INFORMATION: Synthetic antimicrobial peptide

<400> SEQUENCE: 27

Arg Arg Arg Pro Pro Arg Leu Pro Pro Arg Leu Pro Pro Arg Leu Pro
1               5                  10                 15
Pro Arg Val Pro Pro Arg Val Pro Leu Val Ser Asn Cys Ser Arg Thr
                20                 25                 30
Lys Thr His Leu Arg Arg Gly Ser Glu
            35                 40

<210> SEQ ID NO 28
<211> LENGTH: 27
<212> TYPE: PRT
<213> ORGANISM: Artificial
<220> FEATURE:
<223> OTHER INFORMATION: Synthetic antimicrobial peptide
```

```
<400> SEQUENCE: 28

Arg Arg Arg Pro Arg Pro Phe Pro Arg Pro Phe Pro Arg Pro Phe Pro
1               5                   10                  15

Arg Pro Phe Pro Arg Pro Phe Pro Arg Pro Phe
            20                  25

<210> SEQ ID NO 29
<211> LENGTH: 26
<212> TYPE: PRT
<213> ORGANISM: Artificial
<220> FEATURE:
<223> OTHER INFORMATION: Synthetic antimicrobial peptide

<400> SEQUENCE: 29

Arg Arg Arg Pro Arg Leu Pro Arg Pro Phe Pro Arg Pro Val Pro Arg
1               5                   10                  15

Pro Leu Pro Arg Pro Val Pro Arg Pro Ile
            20                  25

<210> SEQ ID NO 30
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 30

Arg Arg Arg Pro Arg Pro Phe Pro Pro Pro Phe Pro Arg Pro Ile Pro
1               5                   10                  15

Arg Pro Phe Pro Arg Pro Phe Pro Arg Pro Leu
            20                  25

<210> SEQ ID NO 31
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 31

Arg Arg Arg Pro Arg Pro Phe Pro Arg Pro Phe Pro His Pro Phe Pro
1               5                   10                  15

Arg Pro Phe Pro Arg Pro Ile Pro Arg Pro Ile
            20                  25

<210> SEQ ID NO 32
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 32

Arg Arg Arg Pro Arg Pro Phe Pro Arg Pro Phe Pro His Pro Ile Pro
1               5                   10                  15

Arg Pro Leu Pro Arg Pro Phe Pro Arg Pro Ile
            20                  25

<210> SEQ ID NO 33
<211> LENGTH: 27
<212> TYPE: PRT
<213> ORGANISM: Artificial
<220> FEATURE:
```

<223> OTHER INFORMATION: Synthetic antimicrobial peptide

<400> SEQUENCE: 33

Arg Arg Arg Pro Arg Pro Phe Pro Arg Pro Phe Pro Arg Pro Phe Pro
1               5                   10                  15

Arg Pro Phe Pro Arg Pro Phe Pro Arg Pro Phe
            20                  25

<210> SEQ ID NO 34
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 34

Arg Arg Arg Pro Arg Pro Phe Pro Arg Pro Phe Pro Arg Pro Phe Pro
1               5                   10                  15

Arg Pro Phe Pro Arg Pro Phe Pro Arg Pro Leu
            20                  25

<210> SEQ ID NO 35
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 35

Arg Arg Arg Pro Arg Pro Phe Pro Arg Pro Phe Pro Arg Pro Phe Pro
1               5                   10                  15

Arg Pro Phe Pro Arg Pro Ile Pro Arg Pro Phe
            20                  25

<210> SEQ ID NO 36
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 36

Arg Arg Arg Pro Arg Pro Phe Pro Arg Pro Phe Pro Arg Pro Phe Pro
1               5                   10                  15

Arg Pro Phe Pro Arg Pro Ile Pro Arg Pro Ile
            20                  25

<210> SEQ ID NO 37
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 37

Arg Arg Arg Pro Arg Pro Phe Pro Arg Pro Phe Pro Arg Pro Phe Pro
1               5                   10                  15

Arg Pro Ile Pro Arg Pro Phe Pro Arg Pro Val
            20                  25

<210> SEQ ID NO 38
<211> LENGTH: 27
<212> TYPE: PRT
<213> ORGANISM: Artificial

<220> FEATURE:
<223> OTHER INFORMATION: Synthetic antimicrobial peptide

<400> SEQUENCE: 38

Arg Arg Arg Pro Arg Pro Phe Pro Arg Pro Phe Pro Arg Pro Phe Pro
1               5                   10                  15

Arg Pro Ile Pro Arg Pro Val Pro Arg Pro Ile
            20                  25

<210> SEQ ID NO 39
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 39

Arg Arg Arg Pro Arg Pro Phe Pro Arg Pro Phe Pro Arg Pro Phe Pro
1               5                   10                  15

Arg Pro Leu Pro Arg Pro Phe Pro Arg Pro Phe
            20                  25

<210> SEQ ID NO 40
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 40

Arg Arg Arg Pro Arg Pro Phe Pro Arg Pro Phe Pro Arg Pro Phe Pro
1               5                   10                  15

Arg Pro Val Pro Arg Pro Leu Pro Arg Pro Ile
            20                  25

<210> SEQ ID NO 41
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 41

Arg Arg Arg Pro Arg Pro Phe Pro Arg Pro Phe Pro Arg Pro Phe Pro
1               5                   10                  15

Arg Pro Val Pro Arg Pro Leu Pro Arg Pro Val
            20                  25

<210> SEQ ID NO 42
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 42

Arg Arg Arg Pro Arg Pro Phe Pro Arg Pro Phe Pro Arg Pro Ile Pro
1               5                   10                  15

Arg Pro Phe Pro Arg Pro Leu Pro Arg Pro Ile
            20                  25

<210> SEQ ID NO 43
<211> LENGTH: 27
<212> TYPE: PRT

```
<213> ORGANISM: Artificial
<220> FEATURE:
<223> OTHER INFORMATION: Synthetic antimicrobial peptide

<400> SEQUENCE: 43

Arg Arg Arg Pro Arg Pro Phe Pro Arg Pro Phe Pro Arg Pro Ile Pro
1               5                   10                  15
Arg Pro Phe Pro Arg Pro Val Pro Arg Pro Val
            20                  25

<210> SEQ ID NO 44
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 44

Arg Arg Arg Pro Arg Pro Phe Pro Arg Pro Phe Pro Arg Pro Leu Pro
1               5                   10                  15
Arg Pro Phe Pro Arg Pro Val Pro Arg Pro Phe
            20                  25

<210> SEQ ID NO 45
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 45

Arg Arg Arg Pro Arg Pro Phe Pro Arg Pro Phe Pro Arg Pro Leu Pro
1               5                   10                  15
Arg Pro Ile Pro Arg Pro Phe Pro Arg Pro Val
            20                  25

<210> SEQ ID NO 46
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 46

Arg Arg Arg Pro Arg Pro Phe Pro Arg Pro Phe Pro Arg Pro Val Pro
1               5                   10                  15
Arg Pro Phe Pro Arg Pro Phe Pro Arg Pro Ile
            20                  25

<210> SEQ ID NO 47
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 47

Arg Arg Arg Pro Arg Pro Phe Pro Arg Pro Phe Pro Arg Pro Val Pro
1               5                   10                  15
Arg Pro Ile Pro Arg Pro Phe Pro Arg Pro Phe
            20                  25

<210> SEQ ID NO 48
<211> LENGTH: 27
```

```
<212> TYPE: PRT
<213> ORGANISM: Artificial
<220> FEATURE:
<223> OTHER INFORMATION: Synthetic antimicrobial peptide

<400> SEQUENCE: 48

Arg Arg Arg Pro Arg Pro Phe Pro Arg Pro Phe Pro Arg Pro Val Pro
1               5                   10                  15

Arg Pro Val Pro Arg Pro Val Pro Arg Pro Phe
            20                  25

<210> SEQ ID NO 49
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 49

Arg Arg Arg Pro Arg Pro Phe Pro Arg Pro Leu Pro Arg Pro Val Pro
1               5                   10                  15

Arg Pro Phe Pro Arg Pro Val Pro Arg Pro Leu
            20                  25

<210> SEQ ID NO 50
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 50

Arg Arg Arg Pro Arg Pro Phe Pro Arg Pro Leu Pro Arg Pro Val Pro
1               5                   10                  15

Arg Pro Phe Pro Arg Pro Val Pro Arg Pro Val
            20                  25

<210> SEQ ID NO 51
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 51

Arg Arg Arg Pro Arg Pro Phe Pro Arg Pro Val Pro Arg Pro Phe Pro
1               5                   10                  15

Arg Pro Phe Pro Arg Pro Phe Pro Arg Pro Phe
            20                  25

<210> SEQ ID NO 52
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 52

Arg Arg Arg Pro Arg Pro Phe Pro Arg Pro Val Pro Arg Pro Ile Pro
1               5                   10                  15

Arg Pro Phe Pro Arg Pro Val Pro Arg Pro Phe
            20                  25

<210> SEQ ID NO 53
```

```
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 53

Arg Arg Arg Pro Arg Pro Phe Pro Arg Pro Val Pro Arg Pro Ile Pro
1               5                   10                  15

Arg Pro Phe Pro Arg Pro Val Pro Arg Pro Val
            20                  25

<210> SEQ ID NO 54
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 54

Arg Arg Arg Pro Arg Pro Phe Pro Arg Pro Val Pro Arg Pro Val Pro
1               5                   10                  15

Arg Pro Phe Pro Arg Pro Ile Pro Arg Pro Leu
            20                  25

<210> SEQ ID NO 55
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 55

Arg Arg Arg Pro Arg Pro Phe Pro Arg Pro Val Pro Arg Pro Val Pro
1               5                   10                  15

Arg Pro Phe Pro Arg Pro Leu Pro Arg Pro Ile
            20                  25

<210> SEQ ID NO 56
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 56

Arg Arg Arg Pro Arg Pro Ile Pro Arg Pro Phe Pro Arg Pro Phe Pro
1               5                   10                  15

Arg Pro Phe Pro Arg Pro Phe Pro Arg Pro Ile
            20                  25

<210> SEQ ID NO 57
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 57

Arg Arg Arg Pro Arg Pro Ile Pro Arg Pro Phe Pro Arg Pro Ile Pro
1               5                   10                  15

Arg Pro Ile Pro Arg Pro Phe Pro Arg Pro Phe
            20                  25
```

<210> SEQ ID NO 58
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 58

Arg Arg Arg Pro Arg Pro Ile Pro Arg Pro Phe Pro Arg Pro Ile Pro
1               5                   10                  15

Arg Pro Val Pro Arg Pro Phe Pro Arg Pro Phe
            20                  25

<210> SEQ ID NO 59
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 59

Arg Arg Arg Pro Arg Pro Ile Pro Arg Pro Phe Pro Arg Pro Ile Pro
1               5                   10                  15

Arg Pro Val Pro Arg Pro Phe Pro Arg Pro Phe
            20                  25

<210> SEQ ID NO 60
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 60

Arg Arg Arg Pro Arg Pro Ile Pro Arg Pro Phe Pro Arg Pro Val Pro
1               5                   10                  15

Arg Pro Val Pro Arg Pro Phe Pro Arg Pro Phe
            20                  25

<210> SEQ ID NO 61
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 61

Arg Arg Arg Pro Arg Pro Val Pro Arg Pro Phe Pro Arg Pro Val Pro
1               5                   10                  15

Arg Pro Leu Pro Arg Pro Phe Pro Arg Pro Phe
            20                  25

<210> SEQ ID NO 62
<211> LENGTH: 41
<212> TYPE: PRT
<213> ORGANISM: Artificial
<220> FEATURE:
<223> OTHER INFORMATION: Synthetic antimicrobial peptide

<400> SEQUENCE: 62

Arg Arg Arg Pro Arg Pro Ile Pro Arg Pro Ile Pro Arg Pro Phe Pro
1               5                   10                  15

Arg Pro Phe Pro Arg Pro Phe His Ala Gln Ser Asn Cys Ser Arg Thr
            20                  25                  30

Lys Thr His Leu Arg Arg Gly Ser Glu
        35                  40

<210> SEQ ID NO 63
<211> LENGTH: 41
<212> TYPE: PRT
<213> ORGANISM: Artificial
<220> FEATURE:
<223> OTHER INFORMATION: Synthetic antimicrobial peptide

<400> SEQUENCE: 63

Arg Arg Arg Pro Arg Pro Phe Pro Arg Pro Phe Pro Arg Pro Val Pro
1               5                   10                  15

Arg Pro Phe Pro Arg Pro Phe Pro Arg Gln Ser Asn Cys Ser Arg Thr
            20                  25                  30

Lys Thr His Leu Arg Arg Gly Ser Glu
        35                  40

<210> SEQ ID NO 64
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 64

Arg Arg Arg Pro Phe Arg Pro Pro Phe Arg Pro Pro Phe Arg Pro Pro
1               5                   10                  15

Phe Arg Pro Pro Phe Arg Pro Pro Phe Arg Pro
            20                  25

<210> SEQ ID NO 65
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 65

Arg Arg Arg Pro Leu Arg Pro Pro Leu Arg Pro Pro Val Arg Pro Pro
1               5                   10                  15

Val Arg Pro Pro Phe Arg Pro Pro Phe Arg Pro
            20                  25

<210> SEQ ID NO 66
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 66

Arg Arg Arg Pro Phe Arg Pro Pro Phe Arg Pro Pro Phe Arg Pro Pro
1               5                   10                  15

Ile Arg Pro Pro Leu Arg Pro Pro Ile Arg Pro
            20                  25

<210> SEQ ID NO 67
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 67

Arg Arg Arg Pro Leu Arg Pro Pro Leu Arg Pro Pro Ile Arg Pro Pro
1               5                   10                  15

Phe Arg Pro Pro Val Arg Pro Pro Phe Arg Pro
            20                  25

<210> SEQ ID NO 68
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 68

Arg Arg Arg Pro Ile Arg Pro Pro Phe Arg Pro Pro Phe Arg Pro Pro
1               5                   10                  15

Leu Arg Pro Pro Val Arg Pro Pro Phe Arg Pro
            20                  25

<210> SEQ ID NO 69
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 69

Arg Arg Arg Pro Ile Arg Pro Pro Phe Arg Pro Pro Phe Arg Pro Pro
1               5                   10                  15

Leu Arg Pro Pro Phe Arg Pro Pro Ile Arg Pro
            20                  25

<210> SEQ ID NO 70
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 70

Arg Arg Arg Pro Leu Arg Pro Pro Leu Arg Pro Pro Phe Arg Pro Pro
1               5                   10                  15

Ile Arg Pro Pro Leu Arg Pro Pro Phe Arg Pro
            20                  25

<210> SEQ ID NO 71
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 71

Arg Arg Arg Pro Leu Arg Pro Pro Ile Arg Pro Pro Phe Arg Pro Pro
1               5                   10                  15

Ile Arg Pro Pro Phe Arg Pro Pro Phe Arg Pro
            20                  25

<210> SEQ ID NO 72
<211> LENGTH: 27
<212> TYPE: PRT
<213> ORGANISM: Artificial
<220> FEATURE:
<223> OTHER INFORMATION: Synthetic antimicrobial peptide

```
<400> SEQUENCE: 72

Arg Arg Arg Pro Ile Arg Pro Pro Phe Arg Pro Pro Phe Arg Pro Pro
1               5                   10                  15

Phe Arg Pro Pro Phe Arg Pro Pro Phe Arg Pro
            20                  25

<210> SEQ ID NO 73
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 73

Arg Arg Arg Pro Phe Arg Pro Pro Val Arg Pro Pro Phe Arg Pro Pro
1               5                   10                  15

Val Arg Pro Pro Ile Arg Pro Pro Val Arg Pro
            20                  25

<210> SEQ ID NO 74
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 74

Arg Arg Arg Pro Phe Arg Pro Pro Val Arg Pro Pro Phe Arg Pro Pro
1               5                   10                  15

Phe Arg Pro Pro Ile Arg Pro Pro Ile Arg Pro
            20                  25

<210> SEQ ID NO 75
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 75

Arg Arg Arg Pro Phe Arg Pro Pro Ile Arg Pro Pro Val Arg Pro Pro
1               5                   10                  15

Phe Arg Pro Pro Phe Arg Pro Pro Phe Arg Pro
            20                  25

<210> SEQ ID NO 76
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 76

Arg Arg Arg Pro Ile Arg Pro Pro Phe Arg Pro Pro Ile Arg Pro Pro
1               5                   10                  15

Val Arg Pro Pro Phe Arg Pro Pro Ile Arg Pro
            20                  25

<210> SEQ ID NO 77
<211> LENGTH: 27
<212> TYPE: PRT
<213> ORGANISM: Artificial
<220> FEATURE:
<223> OTHER INFORMATION: Synthetic antimicrobial peptide
```

```
<400> SEQUENCE: 77

Arg Arg Arg Pro Phe Arg Pro Pro Phe Arg Pro Ile Arg Pro Pro
1               5                   10                  15

Val Arg Pro Pro Phe Arg Pro Pro Phe Arg Pro
            20                  25

<210> SEQ ID NO 78
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 78

Arg Arg Arg Pro Leu Arg Pro Pro Phe Arg Pro Pro Phe Arg Pro Pro
1               5                   10                  15

Phe Arg Pro Pro Ile Arg Pro Pro Val Arg Pro
            20                  25

<210> SEQ ID NO 79
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 79

Arg Arg Arg Pro Phe Arg Pro Pro Phe Arg Pro Pro Phe Arg Pro Pro
1               5                   10                  15

Val Arg Pro Pro Val Arg Pro Pro Phe Arg Pro
            20                  25

<210> SEQ ID NO 80
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 80

Arg Arg Arg Pro Phe Arg Pro Pro Phe Arg Pro Pro Ile Arg Pro Pro
1               5                   10                  15

Val Arg Pro Pro Val Arg Pro Pro Phe Arg Pro
            20                  25

<210> SEQ ID NO 81
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 81

Arg Arg Arg Pro Phe Arg Pro Pro Ile Arg Pro Pro Phe Arg Pro Pro
1               5                   10                  15

Phe Arg Pro Pro Val Arg Pro Pro Ile Arg Pro
            20                  25

<210> SEQ ID NO 82
<211> LENGTH: 27
<212> TYPE: PRT
<213> ORGANISM: Artificial
<220> FEATURE:
```

<223> OTHER INFORMATION: Synthetic antimicrobial peptide

<400> SEQUENCE: 82

Arg Arg Arg Pro Ile Arg Pro Pro Phe Arg Pro Pro Val Arg Pro Pro
1               5                   10                  15
Phe Arg Pro Pro Phe Arg Pro Pro Phe Arg Pro
            20                  25

<210> SEQ ID NO 83
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 83

Arg Arg Arg Pro Leu Arg Pro Pro Phe Arg Pro Pro Ile Arg Pro Pro
1               5                   10                  15
Val Arg Pro Pro Phe Arg Pro Pro Val Arg Pro
            20                  25

<210> SEQ ID NO 84
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 84

Arg Arg Arg Pro Ile Arg Pro Pro Leu Arg Pro Pro Ile Arg Pro Pro
1               5                   10                  15
Phe Arg Pro Pro Phe Arg Pro Pro Leu Arg Pro
            20                  25

<210> SEQ ID NO 85
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 85

Arg Arg Arg Pro Phe Arg Pro Pro Ile Arg Pro Pro Ile Arg Pro Pro
1               5                   10                  15
Phe Arg Pro Pro Phe Arg Pro Pro Ile Arg Pro
            20                  25

<210> SEQ ID NO 86
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 86

Arg Arg Arg Pro Ile Arg Pro Pro Phe Arg Pro Pro Leu Arg Pro Pro
1               5                   10                  15
Leu Arg Pro Pro Val Arg Pro Pro Phe Arg Pro
            20                  25

<210> SEQ ID NO 87
<211> LENGTH: 27
<212> TYPE: PRT
<213> ORGANISM: Artificial

```
<220> FEATURE:
<223> OTHER INFORMATION: Synthetic antimicrobial peptide

<400> SEQUENCE: 87

Arg Arg Arg Pro Phe Arg Pro Pro Phe Arg Pro Pro Ile Arg Pro Pro
1               5                   10                  15

Phe Arg Pro Pro Val Arg Pro Pro Val Arg Pro
            20                  25

<210> SEQ ID NO 88
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 88

Arg Arg Arg Pro Phe Arg Pro Pro Leu Arg Pro Pro Leu Arg Pro Pro
1               5                   10                  15

Val Arg Pro Pro Val Arg Pro Pro Phe Arg Pro
            20                  25

<210> SEQ ID NO 89
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 89

Arg Arg Arg Pro Phe Arg Pro Pro Phe Arg Pro Pro Phe Arg Pro Pro
1               5                   10                  15

Val Arg Pro Pro Val Arg Pro Pro Leu Arg Pro
            20                  25

<210> SEQ ID NO 90
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 90

Arg Arg Arg Pro Phe Arg Pro Pro Ile Arg Pro Pro Phe Arg Pro Pro
1               5                   10                  15

Phe Arg Pro Pro Val Arg Pro Pro Phe Arg Pro
            20                  25

<210> SEQ ID NO 91
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 91

Arg Arg Arg Pro Phe Arg Pro Pro Val Arg Pro Pro Ile Arg Pro Pro
1               5                   10                  15

Val Arg Pro Pro Phe Arg Pro Pro Val Arg Pro
            20                  25

<210> SEQ ID NO 92
<211> LENGTH: 27
<212> TYPE: PRT
```

<213> ORGANISM: Artificial
<220> FEATURE:
<223> OTHER INFORMATION: Synthetic antimicrobial peptide

<400> SEQUENCE: 92

Arg Arg Arg Pro Val Arg Pro Pro Ile Arg Pro Pro Phe Arg Pro
1               5                   10                  15

Phe Arg Pro Pro Phe Arg Pro Pro Phe Arg Pro
            20                  25

<210> SEQ ID NO 93
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 93

Arg Arg Arg Pro Phe Arg Pro Pro Phe Arg Pro Pro Phe Arg Pro
1               5                   10                  15

Val Arg Pro Pro Leu Arg Pro Pro Ile Arg Pro
            20                  25

<210> SEQ ID NO 94
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 94

Arg Arg Arg Pro Phe Arg Pro Pro Val Arg Pro Pro Ile Arg Pro
1               5                   10                  15

Val Arg Pro Pro Phe Arg Pro Pro Phe Arg Pro
            20                  25

<210> SEQ ID NO 95
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 95

Arg Arg Arg Pro Phe Arg Pro Pro Leu Arg Pro Pro Leu Arg Pro
1               5                   10                  15

Ile Arg Pro Pro Val Arg Pro Pro Phe Arg Pro
            20                  25

<210> SEQ ID NO 96
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 96

Arg Arg Arg Pro Phe Arg Pro Pro Ile Arg Pro Pro Phe Arg Pro
1               5                   10                  15

Ile Arg Pro Pro Leu Arg Pro Pro Ile Arg Pro
            20                  25

<210> SEQ ID NO 97
<211> LENGTH: 27

```
<212> TYPE: PRT
<213> ORGANISM: Artificial
<220> FEATURE:
<223> OTHER INFORMATION: Synthetic antimicrobial peptide

<400> SEQUENCE: 97

Arg Arg Arg Pro Leu Arg Pro Pro Phe Arg Pro Phe Arg Pro Pro
1               5                  10                  15

Leu Arg Pro Pro Phe Arg Pro Pro Ile Arg Pro
            20                  25

<210> SEQ ID NO 98
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 98

Arg Arg Arg Pro Phe Arg Pro Pro Phe Arg Pro Pro Val Arg Pro Pro
1               5                  10                  15

Ile Arg Pro Pro Leu Arg Pro Pro Phe Arg Pro
            20                  25

<210> SEQ ID NO 99
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 99

Arg Arg Arg Pro Phe Arg Pro Pro Ile Arg Pro Pro Ile Arg Pro Pro
1               5                  10                  15

Phe Arg Pro Pro Ile Arg Pro Pro Phe Arg Pro
            20                  25

<210> SEQ ID NO 100
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 100

Arg Arg Arg Pro Ile Arg Pro Pro Phe Arg Pro Pro Phe Arg Pro Pro
1               5                  10                  15

Phe Arg Pro Pro Phe Arg Pro Pro Phe Arg Pro
            20                  25

<210> SEQ ID NO 101
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 101

Arg Arg Arg Pro Ile Arg Pro Pro Phe Arg Pro Pro Leu Arg Pro Pro
1               5                  10                  15

Phe Arg Pro Pro Ile Arg Pro Pro Ile Arg Pro
            20                  25

<210> SEQ ID NO 102
```

<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 102

Arg Arg Arg Pro Ile Arg Pro Pro Phe Arg Pro Pro Ile Arg Pro Pro
1               5                   10                  15

Phe Arg Pro Pro Leu Arg Pro Pro Phe Arg Pro
            20                  25

<210> SEQ ID NO 103
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 103

Arg Arg Arg Pro Leu Arg Pro Pro Ile Arg Pro Pro Ile Arg Pro Pro
1               5                   10                  15

Val Arg Pro Pro Phe Arg Pro Pro Ile Arg Pro
            20                  25

<210> SEQ ID NO 104
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 104

Arg Arg Arg Pro Phe Arg Pro Pro Phe Arg Pro Pro Ile Arg Pro Pro
1               5                   10                  15

Phe Arg Pro Pro Phe Arg Pro Pro Leu Arg Pro
            20                  25

<210> SEQ ID NO 105
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 105

Arg Arg Arg Pro Ile Arg Pro Pro Leu Arg Pro Pro Leu Arg Pro Pro
1               5                   10                  15

Phe Arg Pro Pro Phe Arg Pro Pro Phe Arg Pro
            20                  25

<210> SEQ ID NO 106
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 106

Arg Arg Arg Pro Phe Arg Pro Pro Phe Arg Pro Pro Phe Arg Pro Pro
1               5                   10                  15

Ile Arg Pro Pro Ile Arg Pro Pro Leu Arg Pro
            20                  25

```
<210> SEQ ID NO 107
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 107

Arg Arg Arg Pro Phe Arg Pro Pro Phe Arg Pro Pro Val Arg Pro Pro
1               5                   10                  15

Phe Arg Pro Pro Ile Arg Pro Pro Phe Arg Pro
            20                  25

<210> SEQ ID NO 108
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 108

Arg Arg Arg Pro Leu Arg Pro Pro Phe Arg Pro Pro Ile Arg Pro Pro
1               5                   10                  15

Val Arg Pro Pro Val Arg Pro Pro Phe Arg Pro
            20                  25

<210> SEQ ID NO 109
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 109

Arg Arg Arg Pro Phe Arg Pro Pro Ile Arg Pro Pro Val Arg Pro Pro
1               5                   10                  15

Leu Arg Pro Pro Val Arg Pro Pro Phe Arg Pro
            20                  25

<210> SEQ ID NO 110
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 110

Arg Arg Arg Pro Phe Arg Pro Pro Leu Arg Pro Pro Phe Arg Pro Pro
1               5                   10                  15

Ile Arg Pro Pro Ile Arg Pro Pro Val Arg Pro
            20                  25

<210> SEQ ID NO 111
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 111

Arg Arg Arg Pro Leu Arg Pro Pro Val Arg Pro Pro Phe Arg Pro Pro
1               5                   10                  15

Val Arg Pro Pro Leu Arg Pro Pro Phe Arg Pro
            20                  25
```

<210> SEQ ID NO 112
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 112

Arg Arg Arg Pro Phe Arg Pro Pro Ile Arg Pro Pro Phe Arg Pro Pro
1               5                   10                  15

Val Arg Pro Pro Val Arg Pro Pro Val Arg Pro
            20                  25

<210> SEQ ID NO 113
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 113

Arg Arg Arg Pro Leu Arg Pro Pro Val Arg Pro Pro Phe Arg Pro Pro
1               5                   10                  15

Val Arg Pro Pro Phe Arg Pro Pro Phe Arg Pro
            20                  25

<210> SEQ ID NO 114
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 114

Arg Arg Arg Pro Leu Arg Pro Pro Leu Arg Pro Pro Phe Arg Pro Pro
1               5                   10                  15

Leu Arg Pro Pro Phe Arg Pro Pro Phe Arg Pro
            20                  25

<210> SEQ ID NO 115
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 115

Arg Arg Arg Pro Leu Arg Pro Pro Phe Arg Pro Pro Ile Arg Pro Pro
1               5                   10                  15

Phe Arg Pro Pro Phe Arg Pro Pro Phe Arg Pro
            20                  25

<210> SEQ ID NO 116
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 116

Arg Arg Arg Pro Ile Arg Pro Pro Phe Arg Pro Pro Phe Arg Pro Pro
1               5                   10                  15

Val Arg Pro Pro Ile Arg Pro Pro Phe Arg Pro
            20                  25

<210> SEQ ID NO 117
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 117

Arg Arg Arg Pro Ile Arg Pro Pro Ile Arg Pro Phe Arg Pro Pro
1               5                   10                  15

Phe Arg Pro Pro Ile Arg Pro Pro Phe Arg Pro
            20                  25

<210> SEQ ID NO 118
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 118

Arg Arg Arg Pro Phe Arg Pro Pro Phe Arg Pro Leu Arg Pro Pro
1               5                   10                  15

Phe Arg Pro Pro Val Arg Pro Pro Leu Arg Pro
            20                  25

<210> SEQ ID NO 119
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 119

Arg Arg Arg Pro Ile Arg Pro Pro Phe Arg Pro Ile Arg Pro Pro
1               5                   10                  15

Phe Arg Pro Pro Val Arg Pro Pro Val Arg Pro
            20                  25

<210> SEQ ID NO 120
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 120

Arg Arg Arg Pro Leu Arg Pro Pro Phe Arg Pro Pro Phe Arg Pro
1               5                   10                  15

Phe Arg Pro Pro Val Arg Pro Pro Ile Arg Pro
            20                  25

<210> SEQ ID NO 121
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 121

Arg Arg Arg Pro Ile Arg Pro Pro Leu Arg Pro Pro Val Arg Pro
1               5                   10                  15

Ile Arg Pro Pro Phe Arg Pro Pro Phe Arg Pro 20                  25

<210> SEQ ID NO 122
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 122

Arg Arg Arg Pro Phe Arg Pro Pro Phe Arg Pro Pro Phe Arg Pro Pro
1               5                   10                  15

Val Arg Pro Pro Phe Arg Pro Pro Leu Arg Pro
            20                  25

<210> SEQ ID NO 123
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 123

Arg Arg Arg Pro Phe Arg Pro Pro Leu Arg Pro Pro Ile Arg Pro Pro
1               5                   10                  15

Ile Arg Pro Pro Phe Arg Pro Pro Phe Arg Pro
            20                  25

<210> SEQ ID NO 124
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 124

Arg Arg Arg Pro Phe Arg Pro Pro Ile Arg Pro Pro Leu Arg Pro Pro
1               5                   10                  15

Val Arg Pro Pro Leu Arg Pro Pro Phe Arg Pro
            20                  25

<210> SEQ ID NO 125
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 125

Arg Arg Arg Pro Ile Arg Pro Pro Phe Arg Pro Pro Leu Arg Pro Pro
1               5                   10                  15

Phe Arg Pro Pro Val Arg Pro Pro Val Arg Pro
            20                  25

<210> SEQ ID NO 126
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 126

Arg Arg Arg Pro Ile Arg Pro Pro Ile Arg Pro Pro Leu Arg Pro Pro
1               5                   10                  15

```
Phe Arg Pro Pro Phe Arg Pro Pro Phe Arg Pro
            20                  25
```

<210> SEQ ID NO 127
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 127

```
Arg Arg Arg Pro Ile Arg Pro Pro Phe Arg Pro Pro Leu Arg Pro Pro
1               5                   10                  15

Phe Arg Pro Pro Phe Arg Pro Pro Leu Arg Pro
            20                  25
```

<210> SEQ ID NO 128
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 128

```
Arg Arg Arg Pro Phe Arg Pro Pro Phe Arg Pro Pro Leu Arg Pro Pro
1               5                   10                  15

Phe Arg Pro Pro Val Arg Pro Pro Leu Arg Pro
            20                  25
```

<210> SEQ ID NO 129
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 129

```
Arg Arg Arg Pro Phe Arg Pro Pro Phe Arg Pro Pro Val Arg Pro Pro
1               5                   10                  15

Phe Arg Pro Pro Ile Arg Pro Pro Leu Arg Pro
            20                  25
```

<210> SEQ ID NO 130
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 130

```
Arg Arg Arg Pro Phe Arg Pro Pro Ile Arg Pro Pro Leu Arg Pro Pro
1               5                   10                  15

Phe Arg Pro Pro Val Arg Pro Pro Leu Arg Pro
            20                  25
```

<210> SEQ ID NO 131
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 131

```
Arg Arg Arg Pro Ile Arg Pro Pro Phe Arg Pro Pro Phe Arg Pro Pro
1               5                   10                  15
```

Ile Arg Pro Pro Ile Arg Pro Pro Val Arg Pro
            20                  25

<210> SEQ ID NO 132
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 132

Arg Arg Arg Pro Phe Arg Pro Pro Phe Arg Pro Pro Leu Arg Pro Pro
1               5                   10                  15

Val Arg Pro Pro Val Arg Pro Pro Ile Arg Pro
            20                  25

<210> SEQ ID NO 133
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 133

Arg Arg Arg Pro Phe Arg Pro Pro Ile Arg Pro Pro Phe Arg Pro Pro
1               5                   10                  15

Val Arg Pro Pro Ile Arg Pro Pro Val Arg Pro
            20                  25

<210> SEQ ID NO 134
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 134

Arg Arg Arg Pro Phe Arg Pro Pro Phe Arg Pro Pro Phe Arg Pro Pro
1               5                   10                  15

Val Arg Pro Pro Leu Arg Pro Pro Val Arg Pro
            20                  25

<210> SEQ ID NO 135
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 135

Arg Arg Arg Pro Ile Arg Pro Pro Ile Arg Pro Pro Ile Arg Pro Pro
1               5                   10                  15

Ile Arg Pro Pro Ile Arg Pro Pro Leu Arg Pro
            20                  25

<210> SEQ ID NO 136
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 136

Arg Arg Arg Pro Phe Arg Pro Pro Phe Arg Pro Pro Ile Arg Pro Pro

```
            1               5                  10                 15
Phe Arg Pro Pro Ile Arg Pro Pro Leu Arg Pro
            20              25

<210> SEQ ID NO 137
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 137

Arg Arg Arg Pro Leu Arg Pro Pro Phe Arg Pro Phe Arg Pro Pro
1               5                  10                 15
Ile Arg Pro Pro Phe Arg Pro Pro Val Arg Pro
            20              25

<210> SEQ ID NO 138
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 138

Arg Arg Arg Pro Leu Arg Pro Pro Phe Arg Pro Val Arg Pro Pro
1               5                  10                 15
Phe Arg Pro Pro Phe Arg Pro Pro Phe Arg Pro
            20              25

<210> SEQ ID NO 139
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 139

Arg Arg Arg Pro Phe Arg Pro Pro Phe Arg Pro Pro Ile Arg Pro
1               5                  10                 15
Phe Arg Pro Pro Ile Arg Pro Pro Val Arg Pro
            20              25

<210> SEQ ID NO 140
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 140

Arg Arg Arg Pro Ile Arg Pro Pro Ile Arg Pro Pro Phe Arg Pro
1               5                  10                 15
Val Arg Pro Pro Val Arg Pro Pro Phe Arg Pro
            20              25

<210> SEQ ID NO 141
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 141
```

Arg Arg Arg Pro Ile Arg Pro Pro Ile Arg Pro Pro Phe Arg Pro Pro
1               5                   10                  15

Phe Arg Pro Pro Leu Arg Pro Pro Ile Arg Pro
            20                  25

<210> SEQ ID NO 142
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 142

Arg Arg Arg Pro Leu Arg Pro Pro Ile Arg Pro Pro Val Arg Pro Pro
1               5                   10                  15

Phe Arg Pro Pro Val Arg Pro Pro Phe Arg Pro
            20                  25

<210> SEQ ID NO 143
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 143

Arg Arg Arg Pro Phe Arg Pro Pro Val Arg Pro Pro Val Arg Pro Pro
1               5                   10                  15

Phe Arg Pro Pro Leu Arg Pro Pro Val Arg Pro
            20                  25

<210> SEQ ID NO 144
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 144

Arg Arg Arg Pro Ile Arg Pro Pro Leu Arg Pro Pro Val Arg Pro Pro
1               5                   10                  15

Val Arg Pro Pro Phe Arg Pro Pro Phe Arg Pro
            20                  25

<210> SEQ ID NO 145
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 145

Arg Arg Arg Pro Leu Arg Pro Pro Val Arg Pro Pro Phe Arg Pro Pro
1               5                   10                  15

Phe Arg Pro Pro Leu Arg Pro Pro Phe Arg Pro
            20                  25

<210> SEQ ID NO 146
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 146

Arg Arg Arg Pro Leu Arg Pro Pro Phe Arg Pro Pro Ile Arg Pro Pro
1               5                   10                  15

Phe Arg Pro Pro Phe Arg Pro Pro Leu Arg Pro
            20                  25

<210> SEQ ID NO 147
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 147

Arg Arg Arg Pro Phe Arg Pro Pro Phe Arg Pro Pro Ile Arg Pro Pro
1               5                   10                  15

Val Arg Pro Pro Val Arg Pro Pro Phe Arg Pro
            20                  25

<210> SEQ ID NO 148
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 148

Arg Arg Arg Pro Ile Arg Pro Pro Phe Arg Pro Pro Phe Arg Pro Pro
1               5                   10                  15

Phe Arg Pro Pro Phe Arg Pro Pro Leu Arg Pro
            20                  25

<210> SEQ ID NO 149
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 149

Arg Arg Arg Pro Ile Arg Pro Pro Ile Arg Pro Pro Phe Arg Pro Pro
1               5                   10                  15

Phe Arg Pro Pro Val Arg Pro Pro Val Arg Pro
            20                  25

<210> SEQ ID NO 150
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 150

Arg Arg Arg Pro Ile Arg Pro Pro Ile Arg Pro Pro Phe Arg Pro Pro
1               5                   10                  15

Ile Arg Pro Pro Phe Arg Pro Pro Val Arg Pro
            20                  25

<210> SEQ ID NO 151
<211> LENGTH: 27
<212> TYPE: PRT
<213> ORGANISM: Artificial
<220> FEATURE:
<223> OTHER INFORMATION: Synthetic antimicrobial peptide -continued

```
<400> SEQUENCE: 151

Arg Arg Arg Pro Leu Arg Pro Pro Val Arg Pro Pro Leu Arg Pro Pro
1               5                   10                  15
Val Arg Pro Pro Phe Arg Pro Pro Phe Arg Pro
            20                  25

<210> SEQ ID NO 152
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 152

Arg Arg Arg Pro Phe Arg Pro Pro Phe Arg Pro Pro Phe Arg Pro Pro
1               5                   10                  15
Phe Arg Pro Pro Val Arg Pro Pro Ile Arg Pro
            20                  25

<210> SEQ ID NO 153
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 153

Arg Arg Arg Pro Ile Arg Pro Pro Phe Arg Pro Pro Ile Arg Pro Pro
1               5                   10                  15
Val Arg Pro Pro Ile Arg Pro Pro Phe Arg Pro
            20                  25

<210> SEQ ID NO 154
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 154

Arg Arg Arg Pro Phe Arg Pro Pro Phe Arg Pro Pro Val Arg Pro Pro
1               5                   10                  15
Val Arg Pro Pro Phe Arg Pro Pro Phe Arg Pro
            20                  25

<210> SEQ ID NO 155
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 155

Arg Arg Arg Pro Phe Arg Pro Pro Phe Arg Pro Pro Phe Arg Pro Pro
1               5                   10                  15
Phe Arg Pro Pro Phe Arg Pro Pro Leu Arg Pro
            20                  25

<210> SEQ ID NO 156
<211> LENGTH: 27
<212> TYPE: PRT
<213> ORGANISM: Artificial
<220> FEATURE:
<223> OTHER INFORMATION: Synthetic antimicrobial peptide
```

```
<400> SEQUENCE: 156

Arg Arg Arg Pro Phe Arg Pro Pro Leu Arg Pro Pro Phe Arg Pro Pro
1               5                   10                  15

Phe Arg Pro Pro Ile Arg Pro Pro Phe Arg Pro
            20                  25

<210> SEQ ID NO 157
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 157

Arg Arg Arg Pro Ile Arg Pro Pro Phe Arg Pro Pro Ile Arg Pro Pro
1               5                   10                  15

Phe Arg Pro Pro Val Arg Pro Pro Leu Arg Pro
            20                  25

<210> SEQ ID NO 158
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 158

Arg Arg Arg Pro Ile Arg Pro Pro Phe Arg Pro Pro Ile Arg Pro Pro
1               5                   10                  15

Ile Arg Pro Pro Ile Arg Pro Pro Val Arg Pro
            20                  25

<210> SEQ ID NO 159
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 159

Arg Arg Arg Pro Val Arg Pro Pro Ile Arg Pro Pro Ile Arg Pro Pro
1               5                   10                  15

Val Arg Pro Pro Leu Arg Pro Pro Val Arg Pro
            20                  25

<210> SEQ ID NO 160
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 160

Arg Arg Arg Pro Phe Arg Pro Pro Val Arg Pro Pro Phe Arg Pro Pro
1               5                   10                  15

Val Arg Pro Pro Phe Arg Pro Pro Phe Arg Pro
            20                  25

<210> SEQ ID NO 161
<211> LENGTH: 27
<212> TYPE: PRT
<213> ORGANISM: Artificial
<220> FEATURE:
```

<223> OTHER INFORMATION: Synthetic antimicrobial peptide

<400> SEQUENCE: 161

Arg Arg Arg Pro Phe Arg Pro Pro Val Arg Pro Pro Ile Arg Pro Pro
1               5                   10                  15

Val Arg Pro Pro Phe Arg Pro Pro Phe Arg Pro
            20                  25

<210> SEQ ID NO 162
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 162

Arg Arg Arg Pro Phe Arg Pro Pro Ile Arg Pro Pro Phe Arg Pro Pro
1               5                   10                  15

Phe Arg Pro Pro Leu Arg Pro Pro Leu Arg Pro
            20                  25

<210> SEQ ID NO 163
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 163

Arg Arg Arg Pro Ile Arg Pro Pro Phe Arg Pro Pro Phe Arg Pro Pro
1               5                   10                  15

Phe Arg Pro Pro Ile Arg Pro Pro Ile Arg Pro
            20                  25

<210> SEQ ID NO 164
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 164

Arg Arg Arg Pro Phe Arg Pro Pro Ile Arg Pro Pro Leu Arg Pro Pro
1               5                   10                  15

Phe Arg Pro Pro Phe Arg Pro Pro Phe Arg Pro
            20                  25

<210> SEQ ID NO 165
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 165

Arg Arg Arg Pro Phe Arg Pro Pro Leu Arg Pro Pro Phe Arg Pro Pro
1               5                   10                  15

Val Arg Pro Pro Leu Arg Pro Pro Val Arg Pro
            20                  25

<210> SEQ ID NO 166
<211> LENGTH: 27
<212> TYPE: PRT
<213> ORGANISM: Artificial

<220> FEATURE:
<223> OTHER INFORMATION: Synthetic antimicrobial peptide

<400> SEQUENCE: 166

Arg Arg Arg Pro Leu Arg Pro Pro Val Arg Pro Pro Phe Arg Pro
1               5                   10                  15

Val Arg Pro Pro Val Arg Pro Pro Leu Arg Pro
            20                  25

<210> SEQ ID NO 167
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 167

Arg Arg Arg Pro Phe Arg Pro Pro Leu Arg Pro Pro Phe Arg Pro
1               5                   10                  15

Leu Arg Pro Pro Leu Arg Pro Pro Val Arg Pro
            20                  25

<210> SEQ ID NO 168
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 168

Arg Arg Arg Pro Leu Arg Pro Pro Phe Arg Pro Pro Ile Arg Pro
1               5                   10                  15

Val Arg Pro Pro Leu Arg Pro Pro Phe Arg Pro
            20                  25

<210> SEQ ID NO 169
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 169

Arg Arg Arg Pro Ile Arg Pro Pro Leu Arg Pro Pro Val Arg Pro
1               5                   10                  15

Phe Arg Pro Pro Val Arg Pro Pro Phe Arg Pro
            20                  25

<210> SEQ ID NO 170
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 170

Arg Arg Arg Pro Ile Arg Pro Pro Phe Arg Pro Pro Phe Arg Pro
1               5                   10                  15

Phe Arg Pro Pro Val Arg Pro Pro Phe Arg Pro
            20                  25

<210> SEQ ID NO 171
<211> LENGTH: 27
<212> TYPE: PRT

<213> ORGANISM: Artificial
<220> FEATURE:
<223> OTHER INFORMATION: Synthetic antimicrobial peptide

<400> SEQUENCE: 171

Arg Arg Arg Pro Ile Arg Pro Pro Ile Arg Pro Pro Ile Arg Pro Pro
1               5                   10                  15

Ile Arg Pro Pro Phe Arg Pro Pro Phe Arg Pro
            20                  25

<210> SEQ ID NO 172
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 172

Arg Arg Arg Pro Phe Arg Pro Pro Ile Arg Pro Pro Phe Arg Pro Pro
1               5                   10                  15

Ile Arg Pro Pro Val Arg Pro Pro Phe Arg Pro
            20                  25

<210> SEQ ID NO 173
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 173

Arg Arg Arg Pro Leu Arg Pro Pro Ile Arg Pro Pro Leu Arg Pro Pro
1               5                   10                  15

Val Arg Pro Pro Phe Arg Pro Pro Phe Arg Pro
            20                  25

<210> SEQ ID NO 174
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 174

Arg Arg Arg Pro Ile Arg Pro Pro Ile Arg Pro Pro Phe Arg Pro Pro
1               5                   10                  15

Leu Arg Pro Pro Phe Arg Pro Pro Phe Arg Pro
            20                  25

<210> SEQ ID NO 175
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 175

Arg Arg Arg Pro Phe Arg Pro Pro Val Arg Pro Pro Phe Arg Pro Pro
1               5                   10                  15

Leu Arg Pro Pro Phe Arg Pro Pro Phe Arg Pro
            20                  25

<210> SEQ ID NO 176
<211> LENGTH: 27

```
<212> TYPE: PRT
<213> ORGANISM: Artificial
<220> FEATURE:
<223> OTHER INFORMATION: Synthetic antimicrobial peptide

<400> SEQUENCE: 176

Arg Arg Arg Pro Leu Arg Pro Pro Val Arg Pro Ile Arg Pro Pro
1               5                  10                  15

Ile Arg Pro Pro Phe Arg Pro Pro Phe Arg Pro
            20                  25

<210> SEQ ID NO 177
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 177

Arg Arg Arg Pro Phe Arg Pro Pro Ile Arg Pro Phe Arg Pro Pro
1               5                  10                  15

Ile Arg Pro Pro Val Arg Pro Pro Ile Arg Pro
            20                  25

<210> SEQ ID NO 178
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 178

Arg Arg Arg Pro Leu Arg Pro Pro Phe Arg Pro Pro Val Arg Pro Pro
1               5                  10                  15

Phe Arg Pro Pro Phe Arg Pro Pro Phe Arg Pro
            20                  25

<210> SEQ ID NO 179
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 179

Arg Arg Arg Pro Phe Arg Pro Pro Ile Arg Pro Pro Ile Arg Pro Pro
1               5                  10                  15

Phe Arg Pro Pro Phe Arg Pro Pro Phe Arg Pro
            20                  25

<210> SEQ ID NO 180
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 180

Arg Arg Arg Pro Leu Arg Pro Pro Ile Arg Pro Pro Ile Arg Pro Pro
1               5                  10                  15

Ile Arg Pro Pro Phe Arg Pro Pro Phe Arg Pro
            20                  25

<210> SEQ ID NO 181
```

```
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 181

Arg Arg Arg Pro Ile Arg Pro Pro Ile Arg Pro Pro Phe Arg Pro Pro
1               5                   10                  15

Phe Arg Pro Pro Phe Arg Pro Pro Phe Arg Pro
            20                  25

<210> SEQ ID NO 182
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 182

Arg Arg Arg Pro Phe Arg Pro Pro Ile Arg Pro Pro Phe Arg Pro Pro
1               5                   10                  15

Ile Arg Pro Pro Val Arg Pro Pro Phe Arg Pro
            20                  25

<210> SEQ ID NO 183
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 183

Arg Arg Arg Pro Phe Arg Pro Pro Val Arg Pro Pro Leu Arg Pro Pro
1               5                   10                  15

Phe Arg Pro Pro Phe Arg Pro Pro Phe Arg Pro
            20                  25

<210> SEQ ID NO 184
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 184

Arg Arg Arg Pro Ile Arg Pro Pro Ile Arg Pro Pro Phe Arg Pro Pro
1               5                   10                  15

Leu Arg Pro Pro Phe Arg Pro Pro Phe Arg Pro
            20                  25

<210> SEQ ID NO 185
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 185

Arg Arg Arg Pro Leu Arg Pro Pro Ile Arg Pro Pro Ile Arg Pro Pro
1               5                   10                  15

Phe Arg Pro Pro Phe Arg Pro Pro Phe Arg Pro
            20                  25
```

```
<210> SEQ ID NO 186
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 186

Arg Arg Arg Pro Ile Arg Pro Pro Ile Arg Pro Pro Ile Arg Pro Pro
1               5                   10                  15

Phe Arg Pro Pro Phe Arg Pro Pro Phe Arg Pro
            20                  25

<210> SEQ ID NO 187
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 187

Arg Arg Arg Pro Ile Arg Pro Pro Phe Arg Pro Pro Phe Arg Pro Pro
1               5                   10                  15

Val Arg Pro Pro Phe Arg Pro Pro Phe Arg Pro
            20                  25

<210> SEQ ID NO 188
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 188

Arg Arg Arg Pro Phe Arg Pro Pro Phe Arg Pro Pro Ile Arg Pro Pro
1               5                   10                  15

Val Arg Pro Pro Val Arg Pro Pro Phe Arg Pro
            20                  25

<210> SEQ ID NO 189
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 189

Arg Arg Arg Pro Phe Arg Pro Pro Phe Arg Pro Pro Ile Arg Pro Pro
1               5                   10                  15

Val Arg Pro Pro Ile Arg Pro Pro Phe Arg Pro
            20                  25

<210> SEQ ID NO 190
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 190

Arg Arg Arg Pro Phe Arg Pro Pro Ile Arg Pro Pro Phe Arg Pro Pro
1               5                   10                  15

Ile Arg Pro Pro Phe Arg Pro Pro Phe Arg Pro
            20                  25
```

```
<210> SEQ ID NO 191
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 191

Arg Arg Arg Pro Phe Arg Pro Pro Phe Arg Pro Pro Ile Arg Pro Pro
1               5                   10                  15

Phe Arg Pro Pro Val Arg Pro Pro Phe Arg Pro
            20                  25

<210> SEQ ID NO 192
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 192

Arg Arg Arg Pro Phe Arg Pro Pro Phe Arg Pro Pro Phe Arg Pro Pro
1               5                   10                  15

Val Arg Pro Pro Val Arg Pro Pro Phe Arg Pro
            20                  25

<210> SEQ ID NO 193
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 193

Arg Arg Arg Pro Phe Arg Pro Pro Ile Arg Pro Pro Phe Arg Pro Pro
1               5                   10                  15

Ile Arg Pro Pro Phe Arg Pro Pro Phe Arg Pro
            20                  25

<210> SEQ ID NO 194
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 194

Arg Arg Arg Pro Leu Arg Pro Pro Phe Arg Pro Pro Phe Arg Pro Pro
1               5                   10                  15

Ile Arg Pro Pro Phe Arg Pro Pro Phe Arg Pro
            20                  25

<210> SEQ ID NO 195
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 195

Arg Arg Arg Pro Phe Arg Pro Pro Ile Arg Pro Pro Phe Arg Pro Pro
1               5                   10                  15

Val Arg Pro Pro Val Arg Pro Pro Val Arg Pro
            20                  25
```

<210> SEQ ID NO 196
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 196

Arg Arg Arg Pro Phe Arg Pro Pro Leu Arg Pro Ile Arg Pro Pro
1               5                   10                  15

Ile Arg Pro Pro Phe Arg Pro Pro Phe Arg Pro
            20                  25

<210> SEQ ID NO 197
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 197

Arg Arg Arg Pro Phe Arg Pro Pro Phe Arg Pro Phe Arg Pro Pro
1               5                   10                  15

Phe Arg Pro Pro Leu Arg Pro Pro Phe Arg Pro
            20                  25

<210> SEQ ID NO 198
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 198

Arg Arg Arg Pro Phe Arg Pro Pro Phe Arg Pro Phe Arg Pro Pro
1               5                   10                  15

Phe Arg Pro Pro Phe Arg Pro Pro Phe Arg Pro
            20                  25

<210> SEQ ID NO 199
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 199

Arg Arg Arg Pro Leu Arg Pro Pro Ile Arg Pro Pro Phe Arg Pro
1               5                   10                  15

Val Arg Pro Pro Phe Arg Pro Pro Phe Arg Pro
            20                  25

<210> SEQ ID NO 200
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 200

Arg Arg Arg Pro Phe Arg Pro Pro Phe Arg Pro Pro Leu Arg Pro
1               5                   10                  15

Phe Arg Pro Pro Val Arg Pro Pro Phe Arg Pro 20                  25

<210> SEQ ID NO 201
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 201

Arg Arg Arg Pro Phe Arg Pro Pro Ile Arg Pro Pro Ile Arg Pro Pro
1               5                   10                  15

Phe Arg Pro Pro Ile Arg Pro Pro Phe Arg Pro
                20                  25

<210> SEQ ID NO 202
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 202

Arg Arg Arg Pro Phe Arg Pro Pro Phe Arg Pro Pro Phe Arg Pro Pro
1               5                   10                  15

Leu Arg Pro Pro Phe Arg Pro Pro Phe Arg Pro
                20                  25

<210> SEQ ID NO 203
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 203

Arg Arg Arg Pro Phe Arg Pro Pro Ile Arg Pro Pro Phe Arg Pro Pro
1               5                   10                  15

Ile Arg Pro Pro Phe Arg Pro Pro Phe Arg Pro
                20                  25

<210> SEQ ID NO 204
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 204

Arg Arg Arg Pro Leu Arg Pro Pro Leu Arg Pro Pro Phe Arg Pro Pro
1               5                   10                  15

Ile Arg Pro Pro Phe Arg Pro Pro Phe Arg Pro
                20                  25

<210> SEQ ID NO 205
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 205

Arg Arg Arg Pro Phe Arg Pro Pro Phe Arg Pro Pro Ile Arg Pro Pro
1               5                   10                  15

Val Arg Pro Pro Phe Arg Pro Pro Phe Arg Pro
            20                  25

<210> SEQ ID NO 206
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 206

Arg Arg Arg Pro Phe Arg Pro Pro Phe Arg Pro Pro Phe Arg Pro Pro
1               5                   10                  15

Phe Arg Pro Pro Phe Arg Pro Pro Phe Arg Pro
            20                  25

<210> SEQ ID NO 207
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 207

Arg Arg Arg Pro Pro Arg Phe Pro Arg Pro Phe Pro Ile Arg Pro Pro
1               5                   10                  15

Pro Arg Phe Pro Arg Pro Ile Pro Phe Arg Pro
            20                  25

<210> SEQ ID NO 208
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 208

Arg Arg Arg Pro Pro Arg Phe Pro Arg Pro Phe Pro Val Arg Pro Pro
1               5                   10                  15

Pro Arg Phe Pro Arg Pro Ile Pro Val Arg Pro
            20                  25

<210> SEQ ID NO 209
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 209

Arg Arg Arg Pro Pro Arg Ile Pro Arg Pro Phe Pro Ile Arg Pro Pro
1               5                   10                  15

Pro Arg Phe Pro Arg Pro Ile Pro Phe Arg Pro
            20                  25

<210> SEQ ID NO 210
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 210

Arg Arg Arg Pro Pro Arg Ile Pro Arg Pro Ile Pro Val Arg Pro Pro
1               5                   10                  15

-continued

Pro Arg Ile Pro Arg Pro Ile Pro Phe Arg Pro
            20                  25

<210> SEQ ID NO 211
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 211

Arg Arg Arg Pro Pro Arg Leu Pro Arg Pro Phe Pro Phe Arg Pro Pro
1               5                   10                  15

Pro Arg Phe Pro Arg Pro Ile Pro Phe Arg Pro
            20                  25

<210> SEQ ID NO 212
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 212

Arg Arg Arg Pro Pro Arg Leu Pro Arg Pro Phe Pro Phe Arg Pro Pro
1               5                   10                  15

Pro Arg Phe Pro Arg Pro Val Pro Ile Arg Pro
            20                  25

<210> SEQ ID NO 213
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 213

Arg Arg Arg Pro Pro Arg Leu Pro Arg Pro Phe Pro Phe Arg Pro Pro
1               5                   10                  15

Pro Arg Leu Pro Arg Pro Phe Pro Ile Arg Pro
            20                  25

<210> SEQ ID NO 214
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 214

Arg Arg Arg Pro Pro Arg Leu Pro Arg Pro Phe Pro Phe Arg Pro Pro
1               5                   10                  15

Pro Arg Leu Pro Arg Pro Ile Pro Leu Arg Pro
            20                  25

<210> SEQ ID NO 215
<211> LENGTH: 26
<212> TYPE: PRT
<213> ORGANISM: Artificial
<220> FEATURE:
<223> OTHER INFORMATION: Synthetic antimicrobial peptide

<400> SEQUENCE: 215

Arg Arg Arg Pro Pro Arg Leu Pro Arg Pro Phe Pro Phe Arg Pro Pro

```
                1               5                  10                 15
Pro Arg Pro Arg Pro Phe Pro Phe Arg Pro
            20              25

<210> SEQ ID NO 216
<211> LENGTH: 26
<212> TYPE: PRT
<213> ORGANISM: Artificial
<220> FEATURE:
<223> OTHER INFORMATION: Synthetic antimicrobial peptide

<400> SEQUENCE: 216

Arg Arg Arg Pro Pro Arg Leu Pro Arg Pro Phe Pro Phe Arg Pro Pro
1               5                  10                 15
Pro Arg Pro Arg Pro Leu Pro Val Arg Pro
            20              25

<210> SEQ ID NO 217
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 217

Arg Arg Arg Pro Pro Arg Leu Pro Arg Pro Phe Pro Phe Arg Pro Pro
1               5                  10                 15
Pro Arg Val Pro Arg Pro Phe Pro Leu Arg Pro
            20              25

<210> SEQ ID NO 218
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 218

Arg Arg Arg Pro Pro Arg Leu Pro Arg Pro Phe Pro Phe Arg Pro Pro
1               5                  10                 15
Pro Arg Val Pro Arg Pro Ile Pro Val Arg Pro
            20              25

<210> SEQ ID NO 219
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 219

Arg Arg Arg Pro Pro Arg Leu Pro Arg Pro Phe Pro Phe Arg Pro Pro
1               5                  10                 15
Pro Arg Val Pro Arg Pro Leu Pro Phe Arg Pro
            20              25

<210> SEQ ID NO 220
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 220
```

Arg Arg Arg Pro Pro Arg Leu Pro Arg Pro Phe Pro Ile Arg Pro Pro
1               5                   10                  15

Pro Arg Phe Pro Arg Pro Phe Pro Val Arg Pro
            20                  25

<210> SEQ ID NO 221
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 221

Arg Arg Arg Pro Pro Arg Leu Pro Arg Pro Phe Pro Ile Arg Pro Pro
1               5                   10                  15

Pro Arg Phe Pro Arg Pro Leu Pro Phe Arg Pro
            20                  25

<210> SEQ ID NO 222
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 222

Arg Arg Arg Pro Pro Arg Leu Pro Arg Pro Phe Pro Ile Arg Pro Pro
1               5                   10                  15

Pro Arg Phe Pro Arg Pro Val Pro Leu Arg Pro
            20                  25

<210> SEQ ID NO 223
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 223

Arg Arg Arg Pro Pro Arg Leu Pro Arg Pro Phe Pro Ile Arg Pro Pro
1               5                   10                  15

Pro Arg Leu Pro Arg Pro Leu Pro Phe Arg Pro
            20                  25

<210> SEQ ID NO 224
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 224

Arg Arg Arg Pro Pro Arg Leu Pro Arg Pro Phe Pro Ile Arg Pro Pro
1               5                   10                  15

Pro Arg Val Pro Arg Pro Phe Pro Val Arg Pro
            20                  25

<210> SEQ ID NO 225
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 225

```
Arg Arg Arg Pro Pro Arg Leu Pro Arg Pro Phe Pro Ile Arg Pro Pro
1               5                   10                  15

Pro Arg Val Pro Arg Pro Ile Pro Ile Arg Pro
            20                  25

<210> SEQ ID NO 226
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 226

Arg Arg Arg Pro Pro Arg Leu Pro Arg Pro Phe Pro Ile Arg Pro Pro
1               5                   10                  15

Pro Arg Val Pro Arg Pro Ile Pro Val Arg Pro
            20                  25

<210> SEQ ID NO 227
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 227

Arg Arg Arg Pro Pro Arg Leu Pro Arg Pro Phe Pro Ile Arg Pro Pro
1               5                   10                  15

Pro Arg Val Pro Arg Pro Val Pro Ile Arg Pro
            20                  25

<210> SEQ ID NO 228
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 228

Arg Arg Arg Pro Pro Arg Leu Pro Arg Pro Phe Pro Leu Arg Pro Pro
1               5                   10                  15

Pro Arg Phe Pro Arg Pro Phe Pro Ile Arg Pro
            20                  25

<210> SEQ ID NO 229
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 229

Arg Arg Arg Pro Pro Arg Leu Pro Arg Pro Phe Pro Leu Arg Pro Pro
1               5                   10                  15

Pro Arg Phe Pro Arg Pro Phe Pro Leu Arg Pro
            20                  25

<210> SEQ ID NO 230
<211> LENGTH: 27
<212> TYPE: PRT
<213> ORGANISM: Artificial
<220> FEATURE:
<223> OTHER INFORMATION: Synthetic antimicrobial peptide
```

-continued

<400> SEQUENCE: 230

Arg Arg Arg Pro Pro Arg Leu Pro Arg Pro Phe Pro Leu Arg Pro Pro
1               5                   10                  15

Pro Arg Phe Pro Arg Pro Leu Pro Leu Arg Pro
            20                  25

<210> SEQ ID NO 231
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 231

Arg Arg Arg Pro Pro Arg Leu Pro Arg Pro Phe Pro Leu Arg Pro Pro
1               5                   10                  15

Pro Arg Leu Pro Arg Pro Phe Pro Phe Arg Pro
            20                  25

<210> SEQ ID NO 232
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 232

Arg Arg Arg Pro Pro Arg Leu Pro Arg Pro Phe Pro Leu Arg Pro Pro
1               5                   10                  15

Pro Arg Leu Pro Arg Pro Ile Pro Val Arg Pro
            20                  25

<210> SEQ ID NO 233
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 233

Arg Arg Arg Pro Pro Arg Leu Pro Arg Pro Phe Pro Leu Arg Pro Pro
1               5                   10                  15

Pro Arg Leu Pro Arg Pro Leu Pro Val Arg Pro
            20                  25

<210> SEQ ID NO 234
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 234

Arg Arg Arg Pro Pro Arg Leu Pro Arg Pro Phe Pro Leu Arg Pro Pro
1               5                   10                  15

Pro Arg Val Pro Arg Pro Leu Pro Ile Arg Pro
            20                  25

<210> SEQ ID NO 235
<211> LENGTH: 27
<212> TYPE: PRT
<213> ORGANISM: Artificial
<220> FEATURE:
<223> OTHER INFORMATION: Synthetic antimicrobial peptide -continued

```
<400> SEQUENCE: 235

Arg Arg Arg Pro Pro Arg Leu Pro Arg Pro Phe Pro Leu Arg Pro Pro
1               5                   10                  15

Pro Arg Val Pro Arg Pro Val Pro Phe Arg Pro
            20                  25

<210> SEQ ID NO 236
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 236

Arg Arg Arg Pro Pro Arg Leu Pro Arg Pro Phe Pro Leu Arg Pro Pro
1               5                   10                  15

Pro Arg Val Pro Arg Pro Val Pro Phe Arg Pro
            20                  25

<210> SEQ ID NO 237
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 237

Arg Arg Arg Pro Pro Arg Leu Pro Arg Pro Phe Pro Leu Arg Pro Pro
1               5                   10                  15

Pro Arg Val Pro Arg Pro Val Pro Val Arg Pro
            20                  25

<210> SEQ ID NO 238
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 238

Arg Arg Arg Pro Pro Arg Leu Pro Arg Pro Phe Pro Val Arg Pro Pro
1               5                   10                  15

Pro Arg Phe Pro Arg Pro Phe Pro Ile Arg Pro
            20                  25

<210> SEQ ID NO 239
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 239

Arg Arg Arg Pro Pro Arg Leu Pro Arg Pro Phe Pro Val Arg Pro Pro
1               5                   10                  15

Pro Arg Phe Pro Arg Pro Phe Pro Leu Arg Pro
            20                  25

<210> SEQ ID NO 240
<211> LENGTH: 27
<212> TYPE: PRT
<213> ORGANISM: Artificial
<220> FEATURE:
```

<223> OTHER INFORMATION: Synthetic antimicrobial peptide

<400> SEQUENCE: 240

Arg Arg Arg Pro Pro Arg Leu Pro Arg Pro Phe Pro Val Arg Pro Pro
1               5                   10                  15

Pro Arg Phe Pro Arg Pro Val Pro Phe Arg Pro
            20                  25

<210> SEQ ID NO 241
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 241

Arg Arg Arg Pro Pro Arg Leu Pro Arg Pro Phe Pro Val Arg Pro Pro
1               5                   10                  15

Pro Arg Ile Pro Arg Pro Ile Pro Phe Arg Pro
            20                  25

<210> SEQ ID NO 242
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 242

Arg Arg Arg Pro Pro Arg Leu Pro Arg Pro Phe Pro Val Arg Pro Pro
1               5                   10                  15

Pro Arg Leu Pro Arg Pro Val Pro Phe Arg Pro
            20                  25

<210> SEQ ID NO 243
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 243

Arg Arg Arg Pro Pro Arg Leu Pro Arg Pro Phe Pro Val Arg Pro Pro
1               5                   10                  15

Pro Arg Leu Pro Arg Pro Val Pro Phe Arg Pro
            20                  25

<210> SEQ ID NO 244
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 244

Arg Arg Arg Pro Pro Arg Leu Pro Arg Pro Phe Pro Val Arg Pro Pro
1               5                   10                  15

Pro Arg Leu Pro Arg Pro Val Pro Phe Arg Pro
            20                  25

<210> SEQ ID NO 245
<211> LENGTH: 27
<212> TYPE: PRT
<213> ORGANISM: Artificial

<220> FEATURE:
<223> OTHER INFORMATION: Synthetic antimicrobial peptide

<400> SEQUENCE: 245

Arg Arg Arg Pro Pro Arg Leu Pro Arg Pro Phe Pro Val Arg Pro
1               5                   10                  15

Pro Arg Val Pro Arg Pro Phe Pro Val Arg Pro
            20                  25

<210> SEQ ID NO 246
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 246

Arg Arg Arg Pro Pro Arg Leu Pro Arg Pro Phe Pro Val Arg Pro
1               5                   10                  15

Pro Arg Val Pro Arg Pro Phe Pro Val Arg Pro
            20                  25

<210> SEQ ID NO 247
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 247

Arg Arg Arg Pro Pro Arg Leu Pro Arg Pro Phe Pro Val Arg Pro
1               5                   10                  15

Pro Arg Val Pro Arg Pro Leu Pro Phe Arg Pro
            20                  25

<210> SEQ ID NO 248
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 248

Arg Arg Arg Pro Pro Arg Leu Pro Arg Pro Phe Pro Val Arg Pro
1               5                   10                  15

Pro Arg Val Pro Arg Pro Val Pro Ile Arg Pro
            20                  25

<210> SEQ ID NO 249
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 249

Arg Arg Arg Pro Pro Arg Leu Pro Arg Pro Phe Pro Val Arg Pro
1               5                   10                  15

Pro Arg Val Pro Arg Pro Val Pro Ile Arg Pro
            20                  25

<210> SEQ ID NO 250
<211> LENGTH: 27
<212> TYPE: PRT

<213> ORGANISM: Artificial
<220> FEATURE:
<223> OTHER INFORMATION: Synthetic antimicrobial peptide

<400> SEQUENCE: 250

Arg Arg Arg Pro Pro Arg Leu Pro Arg Pro Ile Pro Phe Arg Pro Pro
1               5                   10                  15
Pro Arg Ile Pro Arg Pro Ile Pro Val Arg Pro
            20                  25

<210> SEQ ID NO 251
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 251

Arg Arg Arg Pro Pro Arg Leu Pro Arg Pro Ile Pro Phe Arg Pro Pro
1               5                   10                  15
Pro Arg Ile Pro Arg Pro Leu Pro Phe Arg Pro
            20                  25

<210> SEQ ID NO 252
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 252

Arg Arg Arg Pro Pro Arg Leu Pro Arg Pro Ile Pro Phe Arg Pro Pro
1               5                   10                  15
Pro Arg Ile Pro Arg Pro Val Pro Val Arg Pro
            20                  25

<210> SEQ ID NO 253
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 253

Arg Arg Arg Pro Pro Arg Leu Pro Arg Pro Ile Pro Phe Arg Pro Pro
1               5                   10                  15
Pro Arg Leu Pro Arg Pro Ile Pro Ile Arg Pro
            20                  25

<210> SEQ ID NO 254
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 254

Arg Arg Arg Pro Pro Arg Leu Pro Arg Pro Ile Pro Phe Arg Pro Pro
1               5                   10                  15
Pro Arg Val Pro Arg Pro Phe Pro Ile Arg Pro
            20                  25

<210> SEQ ID NO 255
<211> LENGTH: 27

```
<212> TYPE: PRT
<213> ORGANISM: Artificial
<220> FEATURE:
<223> OTHER INFORMATION: Synthetic antimicrobial peptide

<400> SEQUENCE: 255

Arg Arg Arg Pro Pro Arg Leu Pro Arg Pro Ile Pro Ile Arg Pro Pro
1               5                   10                  15

Pro Arg Phe Pro Arg Pro Val Pro Phe Arg Pro
            20                  25

<210> SEQ ID NO 256
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 256

Arg Arg Arg Pro Pro Arg Leu Pro Arg Pro Ile Pro Leu Arg Pro Pro
1               5                   10                  15

Pro Arg Val Pro Arg Pro Ile Pro Ile Arg Pro
            20                  25

<210> SEQ ID NO 257
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 257

Arg Arg Arg Pro Pro Arg Leu Pro Arg Pro Ile Pro Val Arg Pro Pro
1               5                   10                  15

Pro Arg Phe Pro Arg Pro Ile Pro Phe Arg Pro
            20                  25

<210> SEQ ID NO 258
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 258

Arg Arg Arg Pro Pro Arg Leu Pro Arg Pro Ile Pro Val Arg Pro Pro
1               5                   10                  15

Pro Arg Phe Pro Arg Pro Ile Pro Phe Arg Pro
            20                  25

<210> SEQ ID NO 259
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 259

Arg Arg Arg Pro Pro Arg Leu Pro Arg Pro Ile Pro Val Arg Pro Pro
1               5                   10                  15

Pro Arg Phe Pro Arg Pro Ile Pro Val Arg Pro
            20                  25

<210> SEQ ID NO 260
```

```
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 260

Arg Arg Arg Pro Pro Arg Leu Pro Arg Pro Ile Pro Val Arg Pro Pro
1               5                   10                  15

Pro Arg Ile Pro Arg Pro Ile Pro Val Arg Pro
            20                  25

<210> SEQ ID NO 261
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 261

Arg Arg Arg Pro Pro Arg Leu Pro Arg Pro Ile Pro Val Arg Pro Pro
1               5                   10                  15

Pro Arg Ile Pro Arg Pro Val Pro Phe Arg Pro
            20                  25

<210> SEQ ID NO 262
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 262

Arg Arg Arg Pro Pro Arg Leu Pro Arg Pro Ile Pro Val Arg Pro Pro
1               5                   10                  15

Pro Arg Leu Pro Arg Pro Val Pro Leu Arg Pro
            20                  25

<210> SEQ ID NO 263
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 263

Arg Arg Arg Pro Pro Arg Leu Pro Arg Pro Ile Pro Val Arg Pro Pro
1               5                   10                  15

Pro Arg Val Pro Arg Pro Ile Pro Leu Arg Pro
            20                  25

<210> SEQ ID NO 264
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 264

Arg Arg Arg Pro Pro Arg Leu Pro Arg Pro Leu Pro Phe Arg Pro Pro
1               5                   10                  15

Pro Arg Phe Pro Arg Pro Val Pro Val Arg Pro
            20                  25
```

<210> SEQ ID NO 265
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 265

Arg Arg Arg Pro Pro Arg Leu Pro Arg Pro Leu Pro Phe Arg Pro Pro
1               5                   10                  15

Pro Arg Leu Pro Arg Pro Phe Pro Val Arg Pro
            20                  25

<210> SEQ ID NO 266
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 266

Arg Arg Arg Pro Pro Arg Leu Pro Arg Pro Leu Pro Phe Arg Pro Pro
1               5                   10                  15

Pro Arg Leu Pro Arg Pro Val Pro Val Arg Pro
            20                  25

<210> SEQ ID NO 267
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 267

Arg Arg Arg Pro Pro Arg Leu Pro Arg Pro Leu Pro Phe Arg Pro Pro
1               5                   10                  15

Pro Arg Val Pro Arg Pro Phe Pro Ile Arg Pro
            20                  25

<210> SEQ ID NO 268
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 268

Arg Arg Arg Pro Pro Arg Leu Pro Arg Pro Leu Pro Phe Arg Pro Pro
1               5                   10                  15

Pro Arg Val Pro Arg Pro Val Pro Leu Arg Pro
            20                  25

<210> SEQ ID NO 269
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 269

Arg Arg Arg Pro Pro Arg Leu Pro Arg Pro Leu Pro Phe Arg Pro Pro
1               5                   10                  15

Pro Arg Val Pro Arg Pro Val Pro Val Arg Pro
            20                  25

<210> SEQ ID NO 270
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 270

Arg Arg Arg Pro Pro Arg Leu Pro Arg Pro Leu Pro Phe Arg Pro Pro
1               5                   10                  15

Pro Arg Val Pro Arg Pro Val Pro Val Arg Pro
            20                  25

<210> SEQ ID NO 271
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 271

Arg Arg Arg Pro Pro Arg Leu Pro Arg Pro Leu Pro Phe Arg Pro Pro
1               5                   10                  15

Pro Arg Val Pro Arg Pro Val Pro Val Arg Pro
            20                  25

<210> SEQ ID NO 272
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 272

Arg Arg Arg Pro Pro Arg Leu Pro Arg Pro Leu Pro Ile Arg Pro Pro
1               5                   10                  15

Pro Arg Phe Pro Arg Pro Ile Pro Val Arg Pro
            20                  25

<210> SEQ ID NO 273
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 273

Arg Arg Arg Pro Pro Arg Leu Pro Arg Pro Leu Pro Ile Arg Pro Pro
1               5                   10                  15

Pro Arg Phe Pro Arg Pro Val Pro Leu Arg Pro
            20                  25

<210> SEQ ID NO 274
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 274

Arg Arg Arg Pro Pro Arg Leu Pro Arg Pro Leu Pro Ile Arg Pro Pro
1               5                   10                  15

Pro Arg Phe Pro Arg Pro Val Pro Val Arg Pro
            20                  25

<210> SEQ ID NO 275
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 275

Arg Arg Arg Pro Pro Arg Leu Pro Arg Pro Leu Pro Ile Arg Pro Pro
1               5                   10                  15

Pro Arg Leu Pro Arg Pro Phe Pro Val Arg Pro
            20                  25

<210> SEQ ID NO 276
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 276

Arg Arg Arg Pro Pro Arg Leu Pro Arg Pro Leu Pro Ile Arg Pro Pro
1               5                   10                  15

Pro Arg Leu Pro Arg Pro Val Pro Val Arg Pro
            20                  25

<210> SEQ ID NO 277
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 277

Arg Arg Arg Pro Pro Arg Leu Pro Arg Pro Leu Pro Ile Arg Pro Pro
1               5                   10                  15

Pro Arg Val Pro Arg Pro Phe Pro Ile Arg Pro
            20                  25

<210> SEQ ID NO 278
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 278

Arg Arg Arg Pro Pro Arg Leu Pro Arg Pro Leu Pro Ile Arg Pro Pro
1               5                   10                  15

Pro Arg Val Pro Arg Pro Leu Pro Phe Arg Pro
            20                  25

<210> SEQ ID NO 279
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 279

Arg Arg Arg Pro Pro Arg Leu Pro Arg Pro Leu Pro Ile Arg Pro Pro
1               5                   10                  15

Pro Arg Val Pro Arg Pro Leu Pro Leu Arg Pro 20                  25

<210> SEQ ID NO 280
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 280

Arg Arg Arg Pro Pro Arg Leu Pro Arg Pro Leu Pro Leu Arg Pro Pro
1               5                   10                  15

Pro Arg Phe Pro Arg Pro Phe Pro Val Arg Pro
            20                  25

<210> SEQ ID NO 281
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 281

Arg Arg Arg Pro Pro Arg Leu Pro Arg Pro Leu Pro Leu Arg Pro Pro
1               5                   10                  15

Pro Arg Phe Pro Arg Pro Val Pro Leu Arg Pro
            20                  25

<210> SEQ ID NO 282
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 282

Arg Arg Arg Pro Pro Arg Leu Pro Arg Pro Leu Pro Leu Arg Pro Pro
1               5                   10                  15

Pro Arg Leu Pro His Pro Ile Pro Phe Arg Pro
            20                  25

<210> SEQ ID NO 283
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 283

Arg Arg Arg Pro Pro Arg Leu Pro Arg Pro Leu Pro Val Arg Pro Pro
1               5                   10                  15

Pro Arg Phe Pro Arg Pro Val Pro Phe Arg Pro
            20                  25

<210> SEQ ID NO 284
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 284

Arg Arg Arg Pro Pro Arg Leu Pro Arg Pro Leu Pro Val Arg Pro Pro
1               5                   10                  15

Pro Arg Phe Pro Arg Pro Val Pro Val Arg Pro
            20                  25

<210> SEQ ID NO 285
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 285

Arg Arg Arg Pro Pro Arg Leu Pro Arg Pro Leu Pro Val Arg Pro Pro
1               5                   10                  15

Pro Arg Ile Pro Arg Pro Phe Pro Val Arg Pro
            20                  25

<210> SEQ ID NO 286
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 286

Arg Arg Arg Pro Pro Arg Leu Pro Arg Pro Leu Pro Val Arg Pro Pro
1               5                   10                  15

Pro Arg Ile Pro Arg Pro Leu Pro Leu Arg Pro
            20                  25

<210> SEQ ID NO 287
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 287

Arg Arg Arg Pro Pro Arg Leu Pro Arg Pro Leu Pro Val Arg Pro Pro
1               5                   10                  15

Pro Arg Leu Pro Arg Pro Ile Pro Ile Arg Pro
            20                  25

<210> SEQ ID NO 288
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 288

Arg Arg Arg Pro Pro Arg Leu Pro Arg Pro Leu Pro Val Arg Pro Pro
1               5                   10                  15

Pro Arg Val Pro Arg Pro Phe Pro Leu Arg Pro
            20                  25

<210> SEQ ID NO 289
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 289

Arg Arg Arg Pro Pro Arg Leu Pro Arg Pro Leu Pro Val Arg Pro Pro
1               5                   10                  15

Pro Arg Val Pro Arg Pro Phe Pro Val Arg Pro
            20                  25

<210> SEQ ID NO 290
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 290

Arg Arg Arg Pro Pro Arg Leu Pro Arg Pro Leu Pro Val Arg Pro Pro
1               5                  10                  15

Pro Arg Val Pro Arg Pro Leu Pro Leu Arg Pro
            20                  25

<210> SEQ ID NO 291
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 291

Arg Arg Arg Pro Pro Arg Leu Pro Arg Pro Leu Pro Val Arg Pro Pro
1               5                  10                  15

Pro Arg Val Pro Arg Pro Val Pro Phe Arg Pro
            20                  25

<210> SEQ ID NO 292
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 292

Arg Arg Arg Pro Pro Arg Leu Pro Arg Pro Leu Pro Val Arg Pro Pro
1               5                  10                  15

Pro Arg Val Pro Arg Pro Val Pro Phe Arg Pro
            20                  25

<210> SEQ ID NO 293
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 293

Arg Arg Arg Pro Pro Arg Leu Pro Arg Pro Val Pro Phe Arg Pro Pro
1               5                  10                  15

Pro Arg Phe Pro Arg Pro Phe Pro Ile Arg Pro
            20                  25

<210> SEQ ID NO 294
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 294

Arg Arg Arg Pro Pro Arg Leu Pro Arg Pro Val Pro Phe Arg Pro Pro

```
                1               5                  10                 15
Pro Arg Phe Pro Arg Pro Val Pro Leu Arg Pro
                20                 25

<210> SEQ ID NO 295
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 295

Arg Arg Arg Pro Pro Arg Leu Pro Arg Pro Val Pro Phe Arg Pro Pro
1               5                  10                 15
Pro Arg Ile Pro Arg Pro Phe Pro Leu Arg Pro
                20                 25

<210> SEQ ID NO 296
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 296

Arg Arg Arg Pro Pro Arg Leu Pro Arg Pro Val Pro Phe Arg Pro Pro
1               5                  10                 15
Pro Arg Val Pro Arg Pro Ile Pro Phe Arg Pro
                20                 25

<210> SEQ ID NO 297
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 297

Arg Arg Arg Pro Pro Arg Leu Pro Arg Pro Val Pro Phe Arg Pro Pro
1               5                  10                 15
Pro Arg Val Pro Arg Pro Ile Pro Val Arg Pro
                20                 25

<210> SEQ ID NO 298
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 298

Arg Arg Arg Pro Pro Arg Leu Pro Arg Pro Val Pro Phe Arg Pro Pro
1               5                  10                 15
Pro Arg Val Pro Arg Pro Val Pro Leu Arg Pro
                20                 25

<210> SEQ ID NO 299
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 299
```

-continued

Arg Arg Arg Pro Pro Arg Leu Pro Arg Pro Val Pro Ile Arg Pro Pro
1               5                   10                  15

Pro Arg Phe Pro Arg Pro Ile Pro Phe Arg Pro
            20                  25

<210> SEQ ID NO 300
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 300

Arg Arg Arg Pro Pro Arg Leu Pro Arg Pro Val Pro Ile Arg Pro Pro
1               5                   10                  15

Pro Arg Ile Pro Arg Pro Ile Pro Phe Arg Pro
            20                  25

<210> SEQ ID NO 301
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 301

Arg Arg Arg Pro Pro Arg Leu Pro Arg Pro Val Pro Ile Arg Pro Pro
1               5                   10                  15

Pro Arg Val Pro Arg Pro Val Pro Leu Arg Pro
            20                  25

<210> SEQ ID NO 302
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 302

Arg Arg Arg Pro Pro Arg Leu Pro Arg Pro Val Pro Leu Arg Pro Pro
1               5                   10                  15

Pro Arg Phe Pro Arg Pro Val Pro Val Arg Pro
            20                  25

<210> SEQ ID NO 303
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 303

Arg Arg Arg Pro Pro Arg Leu Pro Arg Pro Val Pro Leu Arg Pro Pro
1               5                   10                  15

Pro Arg Val Pro Arg Pro Leu Pro Ile Arg Pro
            20                  25

<210> SEQ ID NO 304
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 304

```
Arg Arg Arg Pro Pro Arg Leu Pro Arg Pro Val Pro Val Arg Pro Pro
1               5                   10                  15

Pro Arg Phe Pro Arg Pro Val Pro Ile Arg Pro
            20                  25
```

<210> SEQ ID NO 305
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 305

```
Arg Arg Arg Pro Pro Arg Leu Pro Arg Pro Val Pro Val Arg Pro Pro
1               5                   10                  15

Pro Arg Phe Pro Arg Pro Val Pro Val Arg Pro
            20                  25
```

<210> SEQ ID NO 306
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 306

```
Arg Arg Arg Pro Pro Arg Leu Pro Arg Pro Val Pro Val Arg Pro Pro
1               5                   10                  15

Pro Arg Phe Pro Arg Pro Val Pro Val Arg Pro
            20                  25
```

<210> SEQ ID NO 307
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 307

```
Arg Arg Arg Pro Pro Arg Leu Pro Arg Pro Val Pro Val Arg Pro Pro
1               5                   10                  15

Pro Arg Val Pro Arg Pro Val Pro Phe Arg Pro
            20                  25
```

<210> SEQ ID NO 308
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 308

```
Arg Arg Arg Pro Pro Arg Leu Pro Arg Pro Val Pro Val Arg Pro Pro
1               5                   10                  15

Pro Arg Val Pro Arg Pro Val Pro Val Arg Pro
            20                  25
```

<210> SEQ ID NO 309
<211> LENGTH: 27
<212> TYPE: PRT
<213> ORGANISM: Artificial
<220> FEATURE:
<223> OTHER INFORMATION: Synthetic antimicrobial peptide

```
<400> SEQUENCE: 309

Arg Arg Arg Pro Pro Arg Val Pro Arg Pro Phe Pro Ile Arg Pro Pro
1               5                   10                  15

Pro Arg Val Pro Arg Pro Ile Pro Phe Arg Pro
            20                  25

<210> SEQ ID NO 310
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 310

Arg Arg Arg Pro Pro Arg Val Pro Arg Pro Phe Pro Ile Arg Pro Pro
1               5                   10                  15

Pro Arg Val Pro Arg Pro Val Pro Val Arg Pro
            20                  25

<210> SEQ ID NO 311
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 311

Arg Arg Arg Pro Pro Arg Val Pro Arg Pro Phe Pro Val Arg Pro Pro
1               5                   10                  15

Pro Arg Phe Pro Arg Pro Val Pro Phe Arg Pro
            20                  25

<210> SEQ ID NO 312
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 312

Arg Arg Arg Pro Pro Arg Val Pro Arg Pro Ile Pro Ile Arg Pro Pro
1               5                   10                  15

Pro Arg Val Pro Arg Pro Val Pro Phe Arg Pro
            20                  25

<210> SEQ ID NO 313
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 313

Arg Arg Arg Pro Pro Arg Val Pro Arg Pro Ile Pro Ile Arg Pro Pro
1               5                   10                  15

Pro Arg Val Pro Arg Pro Val Pro Val Arg Pro
            20                  25

<210> SEQ ID NO 314
<211> LENGTH: 27
<212> TYPE: PRT
<213> ORGANISM: Artificial
<220> FEATURE:
<223> OTHER INFORMATION: Synthetic antimicrobial peptide
```

-continued

```
<400> SEQUENCE: 314

Arg Arg Arg Pro Pro Arg Val Pro Arg Pro Leu Pro Phe Arg Pro Pro
1               5                   10                  15

Pro Arg Phe Pro Arg Pro Ile Pro Phe Arg Pro
            20                  25

<210> SEQ ID NO 315
<211> LENGTH: 27
<212> TYPE: PRT
<213> ORGANISM: Artificial
<220> FEATURE:
<223> OTHER INFORMATION: Synthetic antimicrobial peptide

<400> SEQUENCE: 315

Arg Arg Arg Pro Pro Arg Val Pro Arg Pro Val Pro Val Arg Pro Pro
1               5                   10                  15

Pro Arg Ile Pro Arg Pro Phe Pro Val Arg Pro
            20                  25

<210> SEQ ID NO 316
<211> LENGTH: 28
<212> TYPE: PRT
<213> ORGANISM: Artificial
<220> FEATURE:
<223> OTHER INFORMATION: Synthetic antimicrobial peptide

<400> SEQUENCE: 316

Arg Arg Arg Thr Arg His Val Phe Ala Arg Pro Phe Pro Phe Arg Pro
1               5                   10                  15

Pro Pro Arg Ile Pro Arg Pro Phe Pro Leu Arg Pro
            20                  25

<210> SEQ ID NO 317
<211> LENGTH: 28
<212> TYPE: PRT
<213> ORGANISM: Artificial
<220> FEATURE:
<223> OTHER INFORMATION: Synthetic antimicrobial peptide

<400> SEQUENCE: 317

Arg Arg Arg Thr Arg His Val Phe Ala Arg Pro Val Pro Val Arg Pro
1               5                   10                  15

Pro Pro Arg Val Pro Arg Pro Phe Pro Val Arg Pro
            20                  25

<210> SEQ ID NO 318
<211> LENGTH: 28
<212> TYPE: PRT
<213> ORGANISM: Artificial
<220> FEATURE:
<223> OTHER INFORMATION: Synthetic antimicrobial peptide

<400> SEQUENCE: 318

Arg Arg Arg Thr Arg His Val Val Pro Arg Pro Leu Pro Val Arg Pro
1               5                   10                  15

Pro Pro Arg Val Pro Arg Pro Phe Pro Leu Arg Pro
            20                  25

<210> SEQ ID NO 319
<211> LENGTH: 41
<212> TYPE: PRT
<213> ORGANISM: Artificial
<220> FEATURE:
```

<223> OTHER INFORMATION: Synthetic antimicrobial peptide

<400> SEQUENCE: 319

Arg Arg Arg Pro Pro Arg Val Pro Arg Pro Phe Pro Val Arg Pro Pro
1               5                   10                  15

Pro Arg Val Pro Arg Pro Ile Pro Phe Val His Asn Cys Ser Arg Thr
            20                  25                  30

Lys Thr His Leu Arg Arg Gly Ser Glu
        35                  40

<210> SEQ ID NO 320
<211> LENGTH: 120
<212> TYPE: DNA
<213> ORGANISM: Artificial
<220> FEATURE:
<223> OTHER INFORMATION: Primer1

<400> SEQUENCE: 320
ccatagcacc atggcgcgtc gccgtccgcc acgttttcca cctcgttttc cacctcgttt    60
ccctccacgt ttccctccac gcttcccacc tcgtttctaa ttgctctaga acaaaaactc   120

<210> SEQ ID NO 321
<211> LENGTH: 120
<212> TYPE: DNA
<213> ORGANISM: Artificial
<220> FEATURE:
<223> OTHER INFORMATION: Primer2

<400> SEQUENCE: 321
ccatagcacc atggcgcgtc gccgtccacg ttttccacct cgttttccac ctcgtttccc    60
tccacgtttc cctccacgct tcccacctcg tttcccgtaa ttgctctaga acaaaaactc   120

<210> SEQ ID NO 322
<211> LENGTH: 120
<212> TYPE: DNA
<213> ORGANISM: Artificial
<220> FEATURE:
<223> OTHER INFORMATION: Primer3

<400> SEQUENCE: 322
ccatagcacc atggcgcgtc gccgtcgttt tccacctcgt tttccacctc gtttccctcc    60
acgtttccct ccacgcttcc cacctcgttt cccgccataa ttgctctaga acaaaaactc   120

<210> SEQ ID NO 323
<211> LENGTH: 120
<212> TYPE: DNA
<213> ORGANISM: Artificial
<220> FEATURE:
<223> OTHER INFORMATION: Primer4

<400> SEQUENCE: 323
ccatagcacc atggcgcgtc gccgttttcc acctcgtttt ccacctcgtt tccctccacg    60
tttccctcca cgcttccacc tcgtttccc gccacgttaa ttgctctaga acaaaaactc   120

<210> SEQ ID NO 324
<211> LENGTH: 120
<212> TYPE: DNA
<213> ORGANISM: Artificial
<220> FEATURE:
<223> OTHER INFORMATION: Primer5

<400> SEQUENCE: 324

```
ccatagcacc atggcgcgtc gccgtccacg tccttttccg cgccttttc cacgtccatt    60 ccctcgtcct ttcccacgcc cttttccacg cccattctaa ttgctctaga acaaaaactc   120
```

<210> SEQ ID NO 325
<211> LENGTH: 120
<212> TYPE: DNA
<213> ORGANISM: Artificial
<220> FEATURE:
<223> OTHER INFORMATION: Primer6

<400> SEQUENCE: 325

```
ccatagcacc atggcgcgtc gccgtcgtcc ttttccgcgc ccttttccac gtccattccc    60
tcgtcctttc ccacgccctt ttccacgccc attcccataa ttgctctaga acaaaaactc   120
```

<210> SEQ ID NO 326
<211> LENGTH: 120
<212> TYPE: DNA
<213> ORGANISM: Artificial
<220> FEATURE:
<223> OTHER INFORMATION: Primer7

<400> SEQUENCE: 326

```
ccatagcacc atggcgcgtc gccgtccttt tccgcgccct tttccacgtc cattccctcg    60
tcctttccca cgcccttttc acgcccattc ccacgttaa ttgctctaga acaaaaactc   120
```

<210> SEQ ID NO 327
<211> LENGTH: 120
<212> TYPE: DNA
<213> ORGANISM: Artificial
<220> FEATURE:
<223> OTHER INFORMATION: Primer8

<400> SEQUENCE: 327

```
ccatagcacc atggcgcgtc gccgttttcc gcgcccttt ccacgtccat tccctcgtcc    60
tttcccacgc ccttttccac gcccattccc acgtccttaa ttgctctaga acaaaaactc   120
```

<210> SEQ ID NO 328
<211> LENGTH: 120
<212> TYPE: DNA
<213> ORGANISM: Artificial
<220> FEATURE:
<223> OTHER INFORMATION: Primer9

<400> SEQUENCE: 328

```
ccatagcacc atggcgcgtc gccgtccacc atttcgtcca cctttccgtc ctccatttcg    60
cccgccgttt cggccaccgt ttcgacctcc tttccgttaa ttgctctaga acaaaaactc   120
```

<210> SEQ ID NO 329
<211> LENGTH: 120
<212> TYPE: DNA
<213> ORGANISM: Artificial
<220> FEATURE:
<223> OTHER INFORMATION: Primer10

<400> SEQUENCE: 329

```
ccatagcacc atggcgcgtc gccgtccatt tcgtccacct ttccgtcctc catttcgccc    60
gccgtttcgg ccaccgtttc gacctccttt ccgtccataa ttgctctaga acaaaaactc   120
```

<210> SEQ ID NO 330
<211> LENGTH: 120
<212> TYPE: DNA
<213> ORGANISM: Artificial

```
<220> FEATURE:
<223> OTHER INFORMATION: Primer11

<400> SEQUENCE: 330
ccatagcacc atggcgcgtc gccgttttcg tccacctttc cgtcctccat ttcgcccgcc      60
gtttcggcca ccgtttcgac ctcctttccg tccaccataa ttgctctaga acaaaaactc    120

<210> SEQ ID NO 331
<211> LENGTH: 120
<212> TYPE: DNA
<213> ORGANISM: Artificial
<220> FEATURE:
<223> OTHER INFORMATION: Primer12

<400> SEQUENCE: 331
ccatagcacc atggcgcgtc gccgtcgtcc acctttccgt cctccatttc gcccgccgtt     60
tcggccaccg tttcgacctc ctttccgtcc accattttaa ttgctctaga acaaaaactc    120

<210> SEQ ID NO 332
<211> LENGTH: 23
<212> TYPE: DNA
<213> ORGANISM: Artificial
<220> FEATURE:
<223> OTHER INFORMATION: Primer13

<400> SEQUENCE: 332 gagttttttgt tctagagcaa tta                                            23

<210> SEQ ID NO 333
<211> LENGTH: 140
<212> TYPE: DNA
<213> ORGANISM: Artificial
<220> FEATURE:
<223> OTHER INFORMATION: Primer14

<400> SEQUENCE: 333
gtatcgatgg ccaagagaga agccgacgat gacgatgaac gtcgccgtcc gccacgtttt     60
ccacctcgtt tttccacctcg tttccctcca cgtttccctc cacgcttccc acctcgtttc   120
tagatggctc tagagggccg                                                140

<210> SEQ ID NO 334
<211> LENGTH: 140
<212> TYPE: DNA
<213> ORGANISM: Artificial
<220> FEATURE:
<223> OTHER INFORMATION: Primer15

<400> SEQUENCE: 334
gtatcgatgg ccaagagaga agccgacgat gacgatgaac gtcgccgtcc acgtcctttt     60
ccgcgccctt tttccacgtcc attccctcgt cctttcccac gcccttttcc acgcccattc   120
tagatggctc tagagggccg                                                140

<210> SEQ ID NO 335
<211> LENGTH: 140
<212> TYPE: DNA
<213> ORGANISM: Artificial
<220> FEATURE:
<223> OTHER INFORMATION: Primer16

<400> SEQUENCE: 335
gtatcgatgg ccaagagaga agccgacgat gacgatgaac gtcgccgtcc atttcgtcca     60
```

```
cctttccgtc ctccatttcg cccgccgttt cggccaccgt ttcgacctcc tttccgtcca      120
tagatggctc tagagggccg                                                   140

<210> SEQ ID NO 336
<211> LENGTH: 20
<212> TYPE: DNA
<213> ORGANISM: Artificial
<220> FEATURE:
<223> OTHER INFORMATION: Primer17

<400> SEQUENCE: 336
cggccctcta gagccatcta                                                    20

<210> SEQ ID NO 337
<211> LENGTH: 120
<212> TYPE: DNA
<213> ORGANISM: Artificial
<220> FEATURE:
<223> OTHER INFORMATION: SEQ ID NO:1 - degenerate primer
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 337
ccatagcacc atggcgcgtc gccgtccgcc acgtnttcca cctcgtnttc cacctcgtnt       60
ccctccacgt ntccctccac gcntcccacc tcgtntctaa ttgctctaga acaaaaactc     120

<210> SEQ ID NO 338
<211> LENGTH: 120
<212> TYPE: DNA
<213> ORGANISM: Artificial
<220> FEATURE:
<223> OTHER INFORMATION: SEQ ID NO:5 - degenerate primer
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
```

```
<222> LOCATION: (83)..(83)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t

<400> SEQUENCE: 338
ccatagcacc atggcgcgtc gccgtccacg tcctnttccg cgccctnttc cacgtccant        60
ccctcgtcct ntcccacgcc ctnttccacg cccantctaa ttgctctaga acaaaaactc      120

<210> SEQ ID NO 339
<211> LENGTH: 120
<212> TYPE: DNA
<213> ORGANISM: Artificial
<220> FEATURE:
<223> OTHER INFORMATION: SEQ ID NO:10 - degenerate primer
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t

<400> SEQUENCE: 339
ccatagcacc atggcgcgtc gccgtccant tcgtccacct ntccgtcctc canttcgccc        60
gccgnttcgg ccaccgnttc gacctcctnt ccgtccataa ttgctctaga acaaaaactc      120

<210> SEQ ID NO 340
<211> LENGTH: 120
<212> TYPE: DNA
<213> ORGANISM: Artificial
<220> FEATURE:
<223> OTHER INFORMATION: Mixed-motif - degenerate primer
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
```

```
<221> NAME/KEY: misc_feature
<222> LOCATION: (89)..(89)
<223> OTHER INFORMATION: n is a, c, g, or t

<400> SEQUENCE: 340
ccatagcacc atggcgcgtc gccgtccgcc acgtnttcca cgtcctnttc canttcgtcc      60
accgccacgt nttccacgtc ctnttccant tcgtccataa ttgctctaga acaaaaactc    120

<210> SEQ ID NO 341
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (4)..(4)
<223> OTHER INFORMATION: Xaa denotes Phe, Ile, Leu, or Val

<400> SEQUENCE: 341

Pro Pro Arg Xaa
1

<210> SEQ ID NO 342
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (3)..(3)
<223> OTHER INFORMATION: Xaa denotes Phe, Ile, Leu, or Val

<400> SEQUENCE: 342

Pro Arg Xaa Pro
1

<210> SEQ ID NO 343
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (2)..(2)
<223> OTHER INFORMATION: Xaa denotes Phe, Ile, Leu, or Val

<400> SEQUENCE: 343

Arg Xaa Pro Pro
1

<210> SEQ ID NO 344
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (1)..(1)
<223> OTHER INFORMATION: Xaa denotes Phe, Ile, Leu, or Val

<400> SEQUENCE: 344

Xaa Pro Pro Arg
1
```

```
<210> SEQ ID NO 345
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (4)..(4)
<223> OTHER INFORMATION: Xaa denotes Phe, Ile, Leu, or Val

<400> SEQUENCE: 345

Pro Arg Pro Xaa
1

<210> SEQ ID NO 346
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_Feature
<222> LOCATION: (3)..(3)
<223> OTHER INFORMATION: Xaa denotes Phe, Ile, Leu, or Val

<400> SEQUENCE: 346

Arg Pro Xaa Pro
1

<210> SEQ ID NO 347
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (2)..(2)
<223> OTHER INFORMATION: Xaa denotes Phe, Ile, Leu, or Val

<400> SEQUENCE: 347

Pro Xaa Pro Arg
1

<210> SEQ ID NO 348
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (1)..(1)
<223> OTHER INFORMATION: Xaa denotes Phe, Ile, Leu, or Val

<400> SEQUENCE: 348

Xaa Pro Arg Pro
1

<210> SEQ ID NO 349
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (3)..(3)
<223> OTHER INFORMATION: Xaa denotes Phe, Ile, Leu, or Val
```

```
<400> SEQUENCE: 349

Pro Pro Xaa Arg
1

<210> SEQ ID NO 350
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (2)..(2)
<223> OTHER INFORMATION: Xaa denotes Phe, Ile, Leu, or Val

<400> SEQUENCE: 350

Pro Xaa Arg Pro
1

<210> SEQ ID NO 351
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (1)..(1)
<223> OTHER INFORMATION: Xaa denotes Phe, Ile, Leu, or Val

<400> SEQUENCE: 351

Xaa Arg Pro Pro
1

<210> SEQ ID NO 352
<211> LENGTH: 4
<212> TYPE: PRT
<213> ORGANISM: Artificial
<220> FEATURE:
<223> OTHER INFORMATION: Synthetic antimicrobial peptide
<220> FEATURE:
<221> NAME/KEY: Misc_feature
<222> LOCATION: (4)..(4)
<223> OTHER INFORMATION: Xaa denotes Phe, Ile, Leu, or Val

<400> SEQUENCE: 352

Arg Pro Pro Xaa
1

<210> SEQ ID NO 353
<211> LENGTH: 5
<212> TYPE: PRT
<213> ORGANISM: Artificial
<220> FEATURE:
<223> OTHER INFORMATION: Synthetic antimicrobial peptide

<400> SEQUENCE: 353

Asp Asp Asp Asp Glu
1               5
```

SYNTHETIC ANTIMICROBIAL POLYPEPTIDES

CROSS-REFERENCE TO RELATED APPLICATIONS

This application is a continuation of PCT application no. PCT/DK2004/000606 filed Sep. 13, 2004, which claims priority or the benefit under 35 U.S.C. 119 of Danish application no. PA 2003 01324 filed Sep. 12, 2003 and U.S. provisional application No. 60/546,541 filed Feb. 20, 2004, the contents of which are fully incorporated herein by reference.

BACKGROUND OF THE INVENTION

Antimicrobial peptides (AMPs) are a relatively newly discovered group of antimicrobial agents with new modes of action.

AMPs are widely distributed in animals, plants and microbes and are among the most ancient host defense factors. Most of the peptides are cationic and amphipatic in nature; a feature that allows interaction with the negatively charged bacterial or fungal membrane.

The peptides range in size from 6-7 amino acids up to 60. More than 500 different AMPs have been isolated to date. They can be divided into several classes based on structure or amino acid composition. The simplest structures are small alpha-helical peptides. Other AMPs folds into beta-sheet structures, while others again form rigid, disulfide bridged tertiary structures.

The AMPs are normally microbicidal (as opposed to static) and are extremely fast acting. Usually, the target organism is killed within minutes. They work by interfering with the membrane function of the target organisms. Several different mechanisms of actions have been shown to exist, but for most AMPs, the overall result is membrane disruption and/or cell lysis.

The selectivity of microbial membranes is mediated by membrane composition, membrane charge and trans-membrane potential. Microbial membranes have a higher negative charge than the membrane of higher organisms, contains different types of phospholipids, and no cholesterol.

It has proven extremely difficult to induce resistance to AMPs in target organisms. This is a reflection of the target; multiple genomic alterations would have to occur to significantly alter the membrane composition or charge.

SUMMARY OF THE INVENTION

The present invention relates to polypeptides having antimicrobial activity, comprising the amino acid sequence:

$X_1$-$X_2$-$X_3$-$X_4$-$X_5$ wherein each of $X_1$, $X_2$, $X_3$, $X_4$ and $X_5$ is one of the amino acid sequences:

| | |
|---|---|
| P-P-R-F, | (SEQ ID NO: 341) |
| P-R-F-P, | (SEQ ID NO: 342) |
| R-F-P-P, | (SEQ ID NO: 343) |
| F-P-P-R, | (SEQ ID NO: 344) |
| P-R-P-F, | (SEQ ID NO: 345) |
| R-P-F-P, | (SEQ ID NO: 346) |
| P-F-P-R, | (SEQ ID NO: 347) |
| F-P-R-P, | (SEQ ID NO: 348) |
| P-P-F-R, | (SEQ ID NO: 349) |
| P-F-R-P, | (SEQ ID NO: 350) |
| F-R-P-P, | (SEQ ID NO: 351) |
| R-P-P-F, | (SEQ ID NO: 352) |
| P-P-R-L, | (SEQ ID NO: 341) |
| P-R-L-P, | (SEQ ID NO: 342) |
| R-L-P-P, | (SEQ ID NO: 343) |
| L-P-P-R, | (SEQ ID NO: 344) |
| P-R-P-L, | (SEQ ID NO: 345) |
| R-P-L-P, | (SEQ ID NO: 346) |
| P-L-P-R, | (SEQ ID NO: 347) |
| L-P-R-P, | (SEQ ID NO: 348) |
| P-P-L-R, | (SEQ ID NO: 349) |
| P-L-R-P, | (SEQ ID NO: 350) |
| L-R-P-P, | (SEQ ID NO: 351) |
| R-P-P-L, | (SEQ ID NO: 352) |
| P-P-R-V, | (SEQ ID NO: 341) |
| P-R-V-P, | (SEQ ID NO: 342) |
| R-V-P-P, | (SEQ ID NO: 343) |
| V-P-P-R, | (SEQ ID NO: 344) |
| P-R-P-V, | (SEQ ID NO: 345) |
| R-P-V-P, | (SEQ ID NO: 346) |
| P-V-P-R, | (SEQ ID NO: 347) |
| V-P-R-P, | (SEQ ID NO: 348) |
| P-P-V-R, | (SEQ ID NO: 349) |
| P-V-R-P, | (SEQ ID NO: 350) |
| V-R-P-P, | (SEQ ID NO: 351) |
| R-P-P-V, | (SEQ ID NO: 352) |
| P-P-R-I, | (SEQ ID NO: 341) |
| P-R-I-P, | (SEQ ID NO: 342) |
| R-I-P-P, | (SEQ ID NO: 343) |
| I-P-P-R, | (SEQ ID NO: 344) |
| P-R-P-I, | (SEQ ID NO: 345) |
| R-P-I-P, | (SEQ ID NO: 346) |
| P-I-P-R, | (SEQ ID NO: 347) |
| I-P-R-P, | (SEQ ID NO: 348) |
| P-P-I-R, | (SEQ ID NO: 349) |

-continued

```
P-I-R-P,        (SEQ ID NO: 350)

I-R-P-P         (SEQ ID NO: 351)
and

R-P-P-I;        (SEQ ID NO: 352)
``` and wherein at most four of $X_1$-$X_5$ are identical.

The present invention also relates to polynucleotides having a nucleotide sequence which encodes for the polypeptide of the invention.

The present invention also relates to a nucleic acid construct comprising the nucleotide sequence, which encodes for the polypeptide of the invention, operably linked to one or more control sequences that direct the production of the polypeptide in a suitable host.

The present invention also relates to a recombinant expression vector comprising the nucleic acid construct of the invention and to a recombinant host cell comprising the nucleic acid construct of the invention.

The present invention also relates to a method for producing a polypeptide of the invention, comprising (a) cultivating a recombinant host cell of the invention under conditions conducive for production of the polypeptide; and (b) recovering the polypeptide.

Definitions

Before discussing the present invention in further details, the following terms and conventions will first be defined:

Antimicrobial activity: The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect, wherein the term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

For purposes of the present invention, antimicrobial activity may be determined according to the procedure described by Lehrer et al., 1991, *Journal of Immunological Methods* 137(2): 167-174.

Polypeptides having antimicrobial activity may be capable of reducing the number of living cells of *Escherichia coli* (DSM 1576) to $\frac{1}{100}$ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Escherichia coli* (DSM 1576) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

Polypeptides having antimicrobial activity may be capable of reducing the number of living cells of *Bacillus subtilis* (ATCC 6633) to $\frac{1}{100}$ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the polypeptides having antimicrobial activity.

Polypeptides having antimicrobial activity may also be capable of inhibiting the outgrowth of *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The polypeptides of the present invention should preferably have at least 20% of the antimicrobial activity of the polypeptide consisting of the amino acid sequence of any of SEQ ID NO: 1 to SEQ ID NO: 319. In a particular preferred embodiment, the polypeptides should have at least 40%, such as at least 50%, preferably at least 60%, such as at least 70%, more preferably at least 80%, such as at least 90%, most preferably at least 95%, such as about or at least 100% of the antimicrobial activity of the polypeptide consisting of the amino acid sequence of any of SEQ ID NO: 1 to SEQ ID NO: 319.

Fragment: When used herein, a "fragment" of the amino acid sequences of the invention is a subsequence of the polypeptides wherein one or more amino acids have been deleted from the amino and/or carboxyl terminus. Preferably the one or more amino acids have been deleted from the carboxyl terminus. Preferably a fragment consists of at least 20 amino acids.

Allelic variant: In the present context, the term "allelic variant" denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Substantially pure polynucleotide: The term "substantially pure polynucleotide" as used herein refers to a polynucleotide preparation, wherein the polynucleotide has been removed from its natural genetic milieu, and is thus free of other extraneous or unwanted coding sequences and is in a form suitable for use within genetically engineered protein production systems. Thus, a substantially pure polynucleotide contains at most 10% by weight of other polynucleotide material with which it is natively associated (lower percentages of other polynucleotide material are preferred, e.g. at most 8% by weight, at most 6% by weight, at most 5% by weight, at most 4%, at most 3% by weight, at most 2% by weight, at most 1% by weight, and at most 0.5% by weight). A substantially pure polynucleotide may, however, include naturally occurring 5' and 3' untranslated regions, such as promoters and terminators. It is preferred that the substantially pure polynucleotide is at least 92% pure, i.e. that the polynucleotide constitutes at least 92% by weight of the total polynucleotide material present in the preparation, and higher percentages are preferred such as at least 94% pure, at least 95% pure, at least 96% pure, at least 96% pure, at least 97% pure, at least 98% pure, at least 99%, and at most 99.5% pure. The polynucleotides disclosed herein are preferably in a substantially pure form. In particular, it is preferred that the polynucleotides disclosed herein are in "essentially pure form", i.e. that the polynucleotide preparation is essentially free of other polynucleotide material with which it is natively associated. Herein, the term "substantially pure polynucleotide" is synonymous with the terms "isolated polynucleotide" and "polynucleotide in isolated form".

Modification(s): In the context of the present invention the term "modification(s)" is intended to mean any chemical modification of the polypeptide consisting of the amino acid sequence $X_1$-$X_2$-$X_3$-$X_4$-$X_5$; wherein $X_1$, $X_2$, $X_3$, $X_4$ and $X_5$ are one of the amino acid sequences: P-P-R-F (SEQ ID NO: 341), P-R-F-P (SEQ ID NO: 342), R-F-P-P (SEQ ID NO: 343), F-P-P-R (SEQ ID NO: 344), P-R-P-F (SEQ ID NO: 345), R-P-F-P (SEQ ID NO: 346), P-F-P-R (SEQ ID NO: 347), F-P-R-P (SEQ ID NO: 348), P-P-F-R (SEQ ID NO: 349), P-F-R-P (SEQ ID NO: 350), F-R-P-P (SEQ ID NO: 351), R-P-P-F (SEQ ID NO: 352), P-P-R-L (SEQ ID NO: 341), P-R-L-P (SEQ ID NO: 342), R-L-P-P (SEQ ID NO: 343), L-P-P-R (SEQ ID NO: 344), P-R-P-L (SEQ ID NO: 345), R-P-L-P (SEQ ID NO: 346), P-L-P-R (SEQ ID NO: 347), L-P-R-P (SEQ ID NO: 348), P-P-L-R (SEQ ID NO: 349), P-L-R-P (SEQ ID NO: 350), L-R-P-P (SEQ ID NO: 351), R-P-P-L (SEQ ID NO: 352), P-P-R-V (SEQ ID NO: 341), P-R-V-P (SEQ ID NO: 342), R-V-P-P (SEQ ID NO: 343), V-P-P-R (SEQ ID NO: 344), P-R-P-V (SEQ ID NO: 345), R-P-V-P (SEQ ID NO: 346), P-V-P-R (SEQ ID NO: 347), V-P-R-P (SEQ ID NO: 348), P-P-V-R (SEQ ID NO: 349), P-V-R-P (SEQ ID NO: 350), V-R-P-P (SEQ ID NO: 351), R-P-P-V (SEQ ID NO: 352), P-P-R-I (SEQ ID NO: 341), P-R-I-P (SEQ ID NO: 342), R-I-P-P (SEQ ID NO: 343), I-P-P-R (SEQ ID NO: 344), P-R-P-I (SEQ ID NO: 345), R-P-I-P (SEQ ID NO: 346), P-I-P-R (SEQ ID NO: 347), I-P-R-P (SEQ ID NO: 348), P-P-I-R (SEQ ID NO: 349), P-I-R-P (SEQ ID NO: 350), I-R-P-P (SEQ ID NO: 351) and R-P-P-I (SEQ ID NO: 352); and wherein at most four of $X_1$-$X_5$ are identical; or the amino acid sequence of any of SEQ ID NO: 1 to SEQ ID NO: 319 as well as genetic manipulation of the DNA encoding the polypeptides. The modification(s) can be replacement(s) of the amino acid side chain(s), substitution(s), deletion(s) and/or insertions(s) in or at the amino acid(s) of interest; or use of unnatural amino acids with similar characteristics in the amino acid sequence. In particular the modification(s) can be amidations, such as amidation of the C-terminus.

cDNA: The term "cDNA" when used in the present context, is intended to cover a DNA molecule which can be prepared by reverse transcription from a mature, spliced, mRNA molecule derived from a eukaryotic cell. cDNA lacks the intron sequences that are usually present in the corresponding genomic DNA. The initial, primary RNA transcript is a precursor to mRNA and it goes through a series of processing events before appearing as mature spliced mRNA. These events include the removal of intron sequences by a process called splicing. When cDNA is derived from mRNA it therefore lacks intron sequences.

Nucleic acid construct: When used herein, the term "nucleic acid construct" means a nucleic acid molecule, either single- or double-stranded, which is isolated from a naturally occurring gene or which has been modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" is defined herein as a configuration in which a control sequence is appropriately placed at a position relative to the coding sequence of the DNA sequence such that the control sequence directs the expression of a polypeptide.

Coding sequence: When used herein the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes DNA, cDNA, and recombinant nucleotide sequences.

Expression: In the present context, the term "expression" includes any step involved in the production of the polypeptide including, but not limited to, transcription, post-transcriptional modification, translation, and post-translational modification. Preferably expression also comprises secretion of the polypeptide.

Expression vector: In the present context, the term "expression vector" covers a DNA molecule, linear or circular, that comprises a segment encoding a polypeptide of the invention, and which is operably linked to additional segments that provide for its transcription.

Host cell: The term "host cell", as used herein, includes any cell type which is susceptible to transformation with a nucleic acid construct.

The terms "polynucleotide probe", "hybridization" as well as the various stringency conditions are defined in the section titled "Polypeptides Having Antimicrobial Activity".

DETAILED DESCRIPTION OF THE INVENTION

Polypeptides Having Antimicrobial Activity

In a first aspect, the present invention relates to polypeptides having antimicrobial activity and where the polypeptides comprise, preferably consist of the amino acid sequence $X_1$-$X_2$-$X_3$-$X_4$-$X_5$; wherein $X_1$, $X_2$, $X_3$, $X_4$ and $X_5$ independently are P-P-R-$Z_1$ (SEQ ID NO: 341), P-R-$Z_2$-P (SEQ ID NO: 342), R-$Z_3$-P-P (SEQ ID NO: 343), $Z_4$-P-P-R (SEQ ID NO: 344), P-R-P-$Z_5$ (SEQ ID NO: 345), R-P-$Z_6$-P (SEQ ID NO: 346), P-$Z_7$-P-R (SEQ ID NO: 347), $Z_8$-P-R-P (SEQ ID NO: 348), P-P-$Z_9$-R (SEQ ID NO: 349), P-$Z_{10}$-R-P (SEQ ID NO: 350), $Z_{11}$-R-P-P (SEQ ID NO: 351) or R-P-P-$Z_{12}$ (SEQ ID NO: 352); wherein $Z_1$, $Z_2$, $Z_3$, $Z_4$, $Z_5$, $Z_6$, $Z_7$, $Z_8$, $Z_9$, $Z_{10}$, $Z_{11}$ and $Z_{12}$ independently are F, I, L, or V.

The invention also relates to polypeptides having antimicrobial activity which comprise, preferably consist of the amino acid sequence $X_1$-$X_2$-$X_3$-$X_4$-$X_5$; wherein $X_1$, $X_2$, $X_3$, $X_4$ and $X_5$ are one of the amino acid sequences:

| | |
|---|---|
| P-P-R-F, | (SEQ ID NO: 341) |
| P-R-F-P, | (SEQ ID NO: 342) |
| R-F-P-P, | (SEQ ID NO: 343) |
| F-P-P-R, | (SEQ ID NO: 344) |
| P-R-P-F, | (SEQ ID NO: 345) |
| R-P-F-P, | (SEQ ID NO: 346) |
| P-F-P-R, | (SEQ ID NO: 347) |
| F-P-R-P, | (SEQ ID NO: 348) |
| P-P-F-R, | (SEQ ID NO: 349) |
| P-F-R-P, | (SEQ ID NO: 350) |
| F-R-P-P, | (SEQ ID NO: 351) |
| R-P-P-F, | (SEQ ID NO: 352) |
| P-P-R-L, | (SEQ ID NO: 341) |
| P-R-L-P, | (SEQ ID NO: 342) |
| R-L-P-P, | (SEQ ID NO: 343) |
| L-P-P-R, | (SEQ ID NO: 344) |
| P-R-P-L, | (SEQ ID NO: 345) |
| R-P-L-P, | (SEQ ID NO: 346) |
| P-L-P-R, | (SEQ ID NO: 347) |
| L-P-R-P, | (SEQ ID NO: 348) |
| P-P-L-R, | (SEQ ID NO: 349) |
| P-L-R-P, | (SEQ ID NO: 350) |
| L-R-P-P, | (SEQ ID NO: 351) |
| R-P-P-L, | (SEQ ID NO: 352) |
| P-P-R-V, | (SEQ ID NO: 341) |
| P-R-V-P, | (SEQ ID NO: 342) |
| R-V-P-P, | (SEQ ID NO: 343) |
| V-P-P-R, | (SEQ ID NO: 344) |
| P-R-P-V, | (SEQ ID NO: 345) |
| R-P-V-P, | (SEQ ID NO: 346) |
| P-V-P-R, | (SEQ ID NO: 347) |
| V-P-R-P, | (SEQ ID NO: 348) |
| P-P-V-R, | (SEQ ID NO: 349) |
| P-V-R-P, | (SEQ ID NO: 350) |
| V-R-P-P, | (SEQ ID NO: 351) |
| R-P-P-V, | (SEQ ID NO: 352) |
| P-P-R-I, | (SEQ ID NO: 341) |
| P-R-I-P, | (SEQ ID NO: 342) |
| R-I-P-P, | (SEQ ID NO: 343) |
| I-P-P-P, | (SEQ ID NO: 344) |
| P-R-P-I, | (SEQ ID NO: 345) |
| R-P-I-P, | (SEQ ID NO: 346) |
| P-I-P-R, | (SEQ ID NO: 347) |
| I-P-R-P, | (SEQ ID NO: 348) |
| P-P-I-R, | (SEQ ID NO: 349) |
| P-I-R-P, | (SEQ ID NO: 350) |
| I-R-P-P and | (SEQ ID NO: 351) |
| R-P-P-I. | (SEQ ID NO: 352) |

In an embodiment $X_1$, $X_2$, $X_3$, $X_4$ and $X_5$ are one of the amino acid sequences:

| | |
|---|---|
| P-P-R-$Z_1$, | (SEQ ID NO: 341) |
| P-R-$Z_2$-P, | (SEQ ID NO: 342) |
| R-$Z_3$-P-P, | (SEQ ID NO: 343) |
| $Z_4$-P-P-R, | (SEQ ID NO: 344) |
| P-R-P-$Z_5$, | (SEQ ID NO: 345) |
| R-P-$Z_6$-P, | (SEQ ID NO: 346) |
| P-$Z_7$-P-R, | (SEQ ID NO: 347) |
| $Z_8$-P-R-P, | (SEQ ID NO: 348) |
| P-P-$Z_9$-R, | (SEQ ID NO: 349) |
| P-$Z_{10}$-R-P, | (SEQ ID NO: 350) |
| $Z_{11}$-R-P-P, and | (SEQ ID NO: 351) |
| R-P-P-$Z_{12}$; | (SEQ ID NO: 352) | wherein $X_1$-$X_5$ are identical, except for the $Z_1$-$Z_{12}$ amino acids; wherein $Z_1$-$Z_{12}$ are F, I, L, or V.

Preferably at most four, more preferably at most three, even more preferably at most two of $X_1$-$X_5$ are identical; and most preferably none of $X_1$-$X_5$ are identical.

In another embodiment $X_1$=$X_2$=$X_3$=$X_4$=$X_5$ and are P-P-R-$Z_1$ SEQ ID NO: 341), P-R-$Z_2$-P (SEQ ID NO: 342), R-$Z_3$-P-P (SEQ ID NO: 343), $Z_4$-P-P-R (SEQ ID NO: 344), P-R-P-$Z_5$ (SEQ ID NO: 345), R-P-$Z_6$-P (SEQ ID NO: 346), P-$Z_7$-P-R (SEQ ID NO: 347), $Z_8$-P-R-P (SEQ ID NO: 348), P-P-$Z_9$-R (SEQ ID NO: 349), P-$Z_{10}$-R-P (SEQ ID NO: 350), $Z_{11}$-R-P-P (SEQ ID NO: 351) or R-P-P-$Z_{12}$ (SEQ ID NO: 352); except that $Z_1$, $Z_2$, $Z_3$, $Z_4$, $Z_5$, $Z_6$, $Z_7$, $Z_8$, $Z_9$, $Z_{10}$, $Z_{11}$ and $Z_{12}$ independently of $X_1$, $X_2$, $X_3$, $X_4$ and $X_5$ are F, I, L, or V.

In another embodiment the present invention relates to polypeptides having antimicrobial activity and where the polypeptides comprises, preferably consists of the amino acid sequence $X_1$-$X_2$-$X_3$-$X_4$-$X_5$-$X_6$; wherein $X_1$, $X_2$, $X_3$, $X_4$, $X_5$ and $X_6$ independently are P-P-R-$Z_1$ (SEQ ID NO: 341), P-R-$Z_2$-P (SEQ ID NO: 342), R-$Z_3$-P-P (SEQ ID NO: 343), $Z_4$-P-P-R (SEQ ID NO: 344), P-R-P-$Z_5$ (SEQ ID NO: 345), R-P-$Z_6$-P (SEQ ID NO: 346), P-$Z_7$-P-R (SEQ ID NO: 347), $Z_8$-P-R-P (SEQ ID NO: 348), P-P-$Z_9$-R (SEQ ID NO: 349), P-$Z_{10}$-R-P (SEQ ID NO: 350), $Z_{11}$-R-P-P (SEQ ID NO: 351) or R-P-P-$Z_{12}$ (SEQ ID NO: 352); wherein $Z_1$, $Z_2$, $Z_3$, $Z_4$, $Z_5$, $Z_6$, $Z_7$, $Z_8$, $Z_9$, $Z_{10}$, $Z_{11}$ and $Z_{12}$ independently are F, I, L, or V.

In another embodiment the invention relates to polypeptides having antimicrobial activity which comprise, preferably consist of the amino acid sequence $X_1$-$X_2$-$X_3$-$X_4$-$X_5$-$X_6$; wherein $X_1$, $X_2$, $X_3$, $X_4$, $X_5$ and $X_6$ are one of the amino acid sequences:

| | |
|---|---|
| P-P-R-F, | (SEQ ID NO: 341) |
| P-R-F-P, | (SEQ ID NO: 342) |
| R-F-P-P, | (SEQ ID NO: 343) |
| F-P-P-R, | (SEQ ID NO: 344) |
| P-R-P-F, | (SEQ ID NO: 345) |
| R-P-F-P, | (SEQ ID NO: 346) |
| P-F-P-R, | (SEQ ID NO: 347) |
| F-P-R-P, | (SEQ ID NO: 348) |
| P-P-F-R, | (SEQ ID NO: 349) |
| P-F-R-P, | (SEQ ID NO: 350) |
| F-R-P-P, | (SEQ ID NO: 351) |
| R-P-P-F, | (SEQ ID NO: 352) |
| P-P-R-L, | (SEQ ID NO: 341) |
| P-R-L-P, | (SEQ ID NO: 342) |
| R-L-P-P, | (SEQ ID NO: 343) |
| L-P-P-R, | (SEQ ID NO: 344) |
| P-R-P-L, | (SEQ ID NO: 345) |
| R-P-L-P, | (SEQ ID NO: 346) |
| P-L-P-R, | (SEQ ID NO: 347) |
| L-P-R-P, | (SEQ ID NO: 348) |
| P-P-L-R, | (SEQ ID NO: 349) |
| P-L-R-P, | (SEQ ID NO: 350) |
| L-R-P-P, | (SEQ ID NO: 351) |
| R-P-P-L, | (SEQ ID NO: 352) |
| P-P-R-V, | (SEQ ID NO: 341) |
| P-R-V-P, | (SEQ ID NO: 342) |
| R-V-P-P, | (SEQ ID NO: 343) |
| V-P-P-R, | (SEQ ID NO: 344) |
| P-R-P-V, | (SEQ ID NO: 345) |
| R-P-V-P, | (SEQ ID NO: 346) |
| P-V-P-R, | (SEQ ID NO: 347) |
| V-P-R-P, | (SEQ ID NO: 348) |
| P-P-V-R, | (SEQ ID NO: 349) |
| P-V-R-P, | (SEQ ID NO: 350) |
| V-R-P-P, | (SEQ ID NO: 351) |
| R-P-P-V, | (SEQ ID NO: 352) |
| P-P-R-I, | (SEQ ID NO: 341) |
| P-R-I-P, | (SEQ ID NO: 342) |
| R-I-P-P, | (SEQ ID NO: 343) |
| I-P-P-R, | (SEQ ID NO: 344) |
| P-R-P-I, | (SEQ ID NO: 345) |
| R-P-I-P, | (SEQ ID NO: 346) |
| P-I-P-R, | (SEQ ID NO: 347) |
| I-P-R-P, | (SEQ ID NO: 348) |
| P-P-I-R, | (SEQ ID NO: 349) |
| P-I-R-P, | (SEQ ID NO: 350) |
| I-R-P-P and | (SEQ ID NO: 351) |
| R-P-P-I. | (SEQ ID NO: 352) |

In another embodiment $X_1$, $X_2$, $X_3$, $X_4$, $X_5$ and $X_6$ are one of the amino acid sequences: P-P-R-$Z_1$ SEQ ID NO: 341), P-R-$Z_2$-P (SEQ ID NO: 342), R-$Z_3$-P-P (SEQ ID NO: 343), $Z_4$-P-P-R (SEQ ID NO: 344), P-R-P-$Z_5$ (SEQ ID NO: 345), R-P-$Z_6$-P (SEQ ID NO: 346), P-$Z_7$-P-R (SEQ ID NO: 347), $Z_8$-P-R-P (SEQ ID NO: 348), P-P-$Z_9$-R (SEQ ID NO: 349), P-$Z_{10}$-R-P (SEQ ID NO: 350), $Z_{11}$-R-P-P (SEQ ID NO: 351) and R-P-P-$Z_{12}$ (SEQ ID NO: 352); wherein $X_1$-$X_6$ are identical, except for the $Z_1$-$Z_{12}$ amino acids; wherein $Z_1$-$Z_{12}$ are F, I, L, or V.

Preferably at most four, more preferably at most three, even more preferably at most two of $X_1$-$X_6$ are identical; and most preferably none of $X_1$-$X_6$ are identical.

In another embodiment $X_1$=$X_2$=$X_3$=$X_4$=$X_5$=$X_6$ are P-P-R-$Z_1$ SEQ ID NO: 341), P-R-$Z_2$-P (SEQ ID NO: 342), R-$Z_3$-P-P (SEQ ID NO: 343), $Z_4$-P-P-R (SEQ ID NO: 344), P-R-P-$Z_5$ (SEQ ID NO: 345), R-P-$Z_6$-P (SEQ ID NO: 346), P-$Z_7$-P-R (SEQ ID NO: 347), $Z_8$-P-R-P (SEQ ID NO: 348), P-P-$Z_9$-R (SEQ ID NO: 349), P-$Z_{10}$-R-P (SEQ ID NO: 350), $Z_{11}$-R-P-P (SEQ ID NO: 351) or R-P-P-$Z_{12}$ (SEQ ID NO: 352); except that $Z_1$, $Z_2$, $Z_3$, $Z_4$, $Z_5$, $Z_6$, $Z_7$, $Z_8$, $Z_9$, $Z_{10}$, $Z_{11}$ and $Z_{12}$ independently of $X_1$, $X_2$, $X_3$, $X_4$, $X_5$ and $X_6$ are F, I, L, or V.

In a preferred embodiment, the present invention relates to polypeptides having antimicrobial activity, which comprise, preferably consist of the amino acid sequence of any of SEQ ID NO: 1 to SEQ ID NO: 319.

In yet another embodiment, the amino acid sequence differs by at most five amino acids (e.g. by five amino acids), such as by at most four amino acids (e.g. by four amino acids), e.g. by at most three amino acids (e.g. by three amino acids), particularly by at most two amino acids (e.g. by two amino acids), such as by one amino acid from the amino acid sequence $X_1$-$X_2$-$X_3$-$X_4$-$X_5$; wherein each of $X_1$, $X_2$, $X_3$, $X_4$ and $X_5$ are:

```
P-P-R-F,        (SEQ ID NO: 341)
P-R-F-P,        (SEQ ID NO: 342)
R-F-P-P,        (SEQ ID NO: 343)
F-P-P-R,        (SEQ ID NO: 344)
P-R-P-F,        (SEQ ID NO: 345)
R-P-F-P,        (SEQ ID NO: 346)
P-F-P-R,        (SEQ ID NO: 347)
F-P-R-P,        (SEQ ID NO: 348)
P-P-F-R,        (SEQ ID NO: 349)
P-F-R-P,        (SEQ ID NO: 350)
F-R-P-P,        (SEQ ID NO: 351)
R-P-P-F,        (SEQ ID NO: 352)
P-P-R-L,        (SEQ ID NO: 341)
P-R-L-P,        (SEQ ID NO: 342)
R-L-P-P,        (SEQ ID NO: 343)
L-P-P-R,        (SEQ ID NO: 344)
P-R-P-L,        (SEQ ID NO: 345)
R-P-L-P,        (SEQ ID NO: 346)
P-L-P-R,        (SEQ ID NO: 347)
L-P-R-P,        (SEQ ID NO: 348)
P-P-L-R,        (SEQ ID NO: 349)
P-L-R-P,        (SEQ ID NO: 350)
L-R-P-P,        (SEQ ID NO: 351)
R-P-P-L,        (SEQ ID NO: 352)
P-P-R-V,        (SEQ ID NO: 341)
P-R-V-P,        (SEQ ID NO: 342)
R-V-P-P,        (SEQ ID NO: 343)
V-P-P-R,        (SEQ ID NO: 344)
P-R-P-V,        (SEQ ID NO: 345)
R-P-V-P,        (SEQ ID NO: 346)
P-V-P-R,        (SEQ ID NO: 347)
V-P-R-P,        (SEQ ID NO: 348)
P-P-V-R,        (SEQ ID NO: 349)
P-V-R-P,        (SEQ ID NO: 350)
V-R-P-P,        (SEQ ID NO: 351)
R-P-P-V,        (SEQ ID NO: 352)
P-P-R-I,        (SEQ ID NO: 341)
P-R-I-P,        (SEQ ID NO: 342)
R-I-P-P,        (SEQ ID NO: 343)
I-P-P-R,        (SEQ ID NO: 344)
P-R-P-I,        (SEQ ID NO: 345)
R-P-I-P,        (SEQ ID NO: 346)
P-I-P-R,        (SEQ ID NO: 347)
I-P-R-P,        (SEQ ID NO: 348)
P-P-I-R,        (SEQ ID NO: 349)
P-I-R-P,        (SEQ ID NO: 350)
I-R-P-P        (SEQ ID NO: 351)
or
R-P-P-I;        (SEQ ID NO: 352)
``` or the amino acid sequence $X_1$-$X_2$-$X_3$-$X_4$-$X_5$-$X_6$; wherein each of $X_1$, $X_2$, $X_3$, $X_4$, $X_5$ and $X_6$ are:

```
P-P-R-F,        (SEQ ID NO: 341)
P-R-F-P,        (SEQ ID NO: 342)
R-F-P-P,        (SEQ ID NO: 343)
F-P-P-R,        (SEQ ID NO: 344)
P-R-P-F,        (SEQ ID NO: 345)
R-P-F-P,        (SEQ ID NO: 346)
P-F-P-R,        (SEQ ID NO: 347)
F-P-R-P,        (SEQ ID NO: 348)
P-P-F-R,        (SEQ ID NO: 349)
P-F-R-P,        (SEQ ID NO: 350)
F-R-P-P,        (SEQ ID NO: 351)
R-P-P-F,        (SEQ ID NO: 352)
P-P-R-L,        (SEQ ID NO: 341)
P-R-L-P,        (SEQ ID NO: 342)
R-L-P-P,        (SEQ ID NO: 343)
L-P-P-R,        (SEQ ID NO: 344)
P-R-P-L,        (SEQ ID NO: 345)
R-P-L-P,        (SEQ ID NO: 346)
P-L-P-R,        (SEQ ID NO: 347)
L-P-R-P,        (SEQ ID NO: 348)
P-P-L-R,        (SEQ ID NO: 349)
P-L-R-P,        (SEQ ID NO: 350)
L-R-P-P,        (SEQ ID NO: 351)
R-P-P-L,        (SEQ ID NO: 352)
P-P-R-V,        (SEQ ID NO: 341)
P-R-V-P,        (SEQ ID NO: 342)
R-V-P-P,        (SEQ ID NO: 343)
```

-continued

| | |
|---|---|
| V-P-P-R, | (SEQ ID NO: 344) |
| P-R-P-V, | (SEQ ID NO: 345) |
| R-P-V-P, | (SEQ ID NO: 346) |
| P-V-P-R, | (SEQ ID NO: 347) |
| V-P-R-P, | (SEQ ID NO: 348) |
| P-P-V-R, | (SEQ ID NO: 349) |
| P-V-R-P, | (SEQ ID NO: 350) |
| V-R-P-P, | (SEQ ID NO: 351) |
| R-P-P-V, | (SEQ ID NO: 352) |
| P-P-R-I, | (SEQ ID NO: 341) |
| P-R-I-P, | (SEQ ID NO: 342) |
| R-I-P-P, | (SEQ ID NO: 343) |
| I-P-P-R, | (SEQ ID NO: 344) |
| P-R-P-I, | (SEQ ID NO: 345) |
| R-P-I-P, | (SEQ ID NO: 346) |
| P-I-P-R, | (SEQ ID NO: 347) |
| I-P-R-P, | (SEQ ID NO: 348) |
| P-P-I-R, | (SEQ ID NO: 349) |
| P-I-R-P, | (SEQ ID NO: 350) |
| I-R-P-P or | (SEQ ID NO: 351) |
| R-P-P-I; | (SEQ ID NO: 352) | or the amino acid sequence of any of SEQ ID NO: 1 to SEQ ID NO: 319.

Preferably, the polypeptides of the present invention comprise the amino acid sequence $X_1$-$X_2$-$X_3$-$X_4$-$X_5$ or $X_1$-$X_2$-$X_3$-$X_4$-$X_5$-$X_6$ or the amino acid sequence of any of SEQ ID NO: 1 to SEQ ID NO: 319; or a fragment thereof that has antimicrobial activity. In another preferred embodiment, the polypeptides consist of the amino acid sequence $X_1$-$X_2$-$X_3$-$X_4$-$X_5$ or $X_1$-$X_2$-$X_3$-$X_4$-$X_5$-$X_6$ or the amino acid sequence of any of SEQ ID NO: 1 to SEQ ID NO: 319.

The amino acids making up the polypeptides of the invention may independently be selected from D or L forms.

The polypeptides of the invention may consist of from 20 to 500 amino acids, preferably from 20 to 400 amino acids, more preferably from 20 to 300 amino acids, even more preferably from 20 to 200 amino acids (such as from 20 to 150 amino acids), most preferably from 20 to 100 amino acids and in particular from 20 to 50 amino acids.

The amino acid sequence $X_1$-$X_2$-$X_3$-$X_4$-$X_5$ or $X_1$-$X_2$-$X_3$-$X_4$-$X_5$-$X_6$ may be directly preceded by an amino acid sequence of from 3 to 10 amino acids (such as from 3 to 5 amino acids) of which at least two amino acids are positively charged at neutral pH (such as arginine, lysine or histidine). Preferably the amino acid sequence $X_1$-$X_2$-$X_3$-$X_4$-$X_5$ or $X_1$-$X_2$-$X_3$-$X_4$-$X_5$-$X_6$ may be directly preceded by the amino acid sequence R-$X_7$-R; wherein $X_7$ is F, I, L, R, or V. The term "directly preceded by" means that the amino acid sequence is attached to the N-terminal of the amino acid sequence $X_1$-$X_2$-$X_3$-$X_4$-$X_5$ or $X_1$-$X_2$-$X_3$-$X_4$-$X_5$-$X_6$.

The polypeptide of the invention may be an artificial variant which comprises, preferably consists of, an amino acid sequence that has at most three, e.g. at most two, such as at most one, substitutions, deletions and/or insertions of amino acids as compared to the amino acid sequences $X_1$-$X_2$-$X_3$-$X_4$-$X_5$ or $X_1$-$X_2$-$X_3$-$X_4$-$X_5$-$X_6$; or the amino acid sequence of any of SEQ ID NO: 1 to SEQ ID NO: 319.

Such artificial variants may be constructed by standard techniques known in the art, such as by site-directed/random mutagenesis of the polypeptide comprising the amino acid sequence $X_1$-$X_2$-$X_3$-$X_4$-$X_5$ or $X_1$-$X_2$-$X_3$-$X_4$-$X_5$-$X_6$ or the amino acid sequence of any of SEQ ID NO: 1 to SEQ ID NO: 319. In one embodiment of the invention, amino acid changes are of a minor nature, that is conservative amino acid substitutions that do not significantly affect the folding and/or activity of the protein; small deletions, typically of one to about 5 amino acids; small amino- or carboxyl-terminal extensions, such as an amino-terminal methionine residue; a small linker peptide of up to about 10-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In an interesting embodiment of the invention, the amino acid changes are of such a nature that the physico-chemical properties of the polypeptides are altered. For example, amino acid changes may be performed, which improve the thermal stability of the polypeptide, which alter the substrate specificity, which changes the pH optimum, and the like.

N-Terminal Extension

An N-terminal extension of the polypeptides of the invention may suitably consist of from 1 to 50 amino acids, preferably 2-20 amino acids, especially 3-15 amino acids. In one embodiment N-terminal peptide extension does not contain an Arg (R). In another embodiment the N-terminal extension comprises a kex2 or kex2-like cleavage site as will be defined further below. In a preferred embodiment the N-terminal extension is a peptide, comprising at least two Glu (E) and/or Asp (D) amino acid residues, such as an N-terminal extension comprising one of the following sequences: EAE, EE, DE and DD.

Kex2 Sites

Kex2 sites (see, e.g., Methods in Enzymology, Vol. 185, ed. D. Goeddel, Academic Press Inc. (1990), San Diego, Calif., "Gene Expression Technology") and kex2-like sites are di-basic recognition sites (i.e., cleavage sites) found between the pro-peptide encoding region and the mature region of some proteins.

Insertion of a kex2 site or a kex2-like site have in certain cases been shown to improve correct endopeptidase processing at the pro-peptide cleavage site resulting in increased protein secretion levels.

In the context of the invention insertion of a kex2 or kex2-like site result in the possibility to obtain cleavage at a certain position in the N-terminal extension resulting in an antimicrobial polypeptide being extended in comparison to the mature polypeptide shown as the amino acid sequences $X_1$-$X_2$-$X_3$-$X_4$-$X_5$ or $X_1$-$X_2$-$X_3$-$X_4$-$X_5$-$X_6$; or the amino acid sequence of any of SEQ ID NO: 1 to SEQ ID NO: 319.

Fused polypeptides

The polypeptides of the present invention also include fused polypeptides or cleavable fusion polypeptides in which another polypeptide is fused at the N-terminus or the C-terminus of the polypeptide of the invention or a fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides and Nucleotide Sequences

The present invention also relates to polynucleotides having a nucleotide sequence which encodes for a polypeptide of the invention. In particular, the present invention relates to polynucleotides consisting of a nucleotide sequence which encodes for a polypeptide of the invention. Due to the degeneracy of the genetic code, the skilled person will easily recognize that several nucleotide sequences encoding each of the polypeptides of the invention may be prepared. It is well known in the art which nucleotides make up codons encoding the amino acids of the polypeptides of the invention.

The present invention also relates to polynucleotides which encode fragments of the amino acid sequences $X_1$-$X_2$-$X_3$-$X_4$-$X_5$ or $X_1$-$X_2$-$X_3$-$X_4$-$X_5$-$X_6$; or the amino acid sequence of any of SEQ ID NO: 1 to SEQ ID NO: 319 that have antimicrobial activity. A subsequence of the polynucleotides is a nucleotide sequence wherein one or more nucleotides from the 5' and/or 3' end have been deleted.

The nucleotide sequence may be obtained by standard cloning procedures used in genetic engineering to relocate the nucleotide sequence from one location to a different site where it will be reproduced. The cloning procedures may involve excision and isolation of a desired fragment comprising the nucleotide sequence encoding the polypeptide, insertion of the fragment into a vector molecule, and incorporation of the recombinant vector into a host cell where multiple copies or clones of the nucleotide sequence will be replicated. The nucleotide sequence may be of genomic, cDNA, RNA, semisynthetic, synthetic origin, or any combinations thereof.

Modification of a nucleotide sequence encoding a polypeptide of the present invention may be necessary for the synthesis of a polypeptide, which comprises an amino acid sequence that has at least one substitution, deletion and/or insertion as compared to the amino acid sequences $X_1$-$X_2$-$X_3$-$X_4$-$X_5$ or $X_1$-$X_2$-$X_3$-$X_4$-$X_5$-$X_6$; or the amino acid sequence of any of SEQ ID NO: 1 to SEQ ID NO: 319. These artificial variants may differ in some engineered way from the polypeptide isolated from its native source, e.g., variants that differ in specific activity, thermostability, pH optimum, or the like.

It will be apparent to those skilled in the art that such modifications can be made outside the regions critical to the function of the molecule and still result in an active polypeptide. Amino acid residues essential to the activity of the polypeptide encoded by the nucleotide sequence of the invention, and therefore preferably not subject to modification, such as substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for antimicrobial activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Moreover, a nucleotide sequence encoding a polypeptide of the present invention may be modified by introduction of nucleotide substitutions which do not give rise to another amino acid sequence of the polypeptide encoded by the nucleotide sequence, but which correspond to the codon usage of the host organism intended for production of the enzyme.

The introduction of a mutation into the nucleotide sequence to exchange one nucleotide for another nucleotide may be accomplished by site-directed mutagenesis using any of the methods known in the art. Particularly useful is the procedure, which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. For a general description of nucleotide substitutions, see, e.g., Ford et al., 1991, *Protein Expression and Purification* 2: 95-107.

Nucleic Acid Constructs

The present invention also relates to nucleic acid constructs comprising a nucleotide sequence of the present invention operably linked to one or more control sequences that direct the expression of the coding sequence in a suitable host cell under conditions compatible with the control sequences.

A nucleotide sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof.

Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant a host cell comprising the nucleic acid construct of the invention, which are advantageously used in the recombinant production of the polypeptides. A vector comprising a nucleotide sequence of the present invention is introduced into a host cell so that the vector is maintained as a chromosomal integrant or as a self-replicating extra-chromosomal vector as described earlier.

The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus*, or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (*Nirenberg* sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Plants

The present invention also relates to a transgenic plant, plant part, or plant cell which has been transformed with a nucleotide sequence encoding a polypeptide having antimicrobial activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor. The recovered polypeptide, plant or plant part may also be used to improve or alter digestive flora in animals and livestock.

The transgenic plant can be dicotyledonous (a dicot) or monocotyledonous (a monocot). Examples of monocot plants are grasses, such as meadow grass (blue grass, *Poa*), forage grass such as Festuca, Lolium, temperate grass, such as Agrostis, and cereals, e.g., wheat, oats, rye, barley, rice, sorghum, and maize (corn).

Examples of dicot plants are tobacco, potato, sugar beet, legumes, such as lupins, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleotide sequence encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences, is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285-294). Organ-specific promoters may be, for example, a promoter from storage sink tissues such as seeds, potato tubers, and fruits (Edwards & Coruzzi, 1990, *Ann. Rev. Genet* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the enzyme in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleotide sequence encoding a polypeptide having antimicrobial activity of the present invention under conditions conducive for production of the polypeptide; and (b) recovering the polypeptide.

Compositions

In a still further aspect, the present invention relates to compositions, such as pharmaceutical compositions, comprising an antimicrobial polypeptide of the invention.

The composition may comprise a polypeptide of the invention as the major polypeptide component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase.

The compositions may further comprise another pharmaceutically active agent, such as an additional biocidal agent, such as another antimicrobial polypeptide exhibiting antimicrobial activity as defined above. The biocidal agent may be an antibiotic, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. The biocidal agent may also be an anti-mycotic agent, including polyenes, e.g. amphotericin B, nystatin; 5-flucosyn; and azoles, e.g. miconazol, ketoconazol, itraconazol and fluconazol.

In an embodiment the biocidal agent is a non-enzymatic chemical agent. In another embodiment the biocidal agent is a non-polypeptide chemical agent.

The biocidal agent may be capable of reducing the number of living cells of *Escherichia coli* (DSM 1576) or *Bacillus subtilis* (ATCC 6633) to $\frac{1}{100}$ after 8 hours (preferably after 4 hours, more preferably after 2 hours, most preferably after 1 hour, and in particular after 30 minutes) incubation at 20° C. in an aqueous solution of 25% (w/w); preferably in an aqueous solution of 10% (w/w); more preferably in an aqueous solution of 5% (w/w); even more preferably in an aqueous solution of 1% (w/w); most preferably in an aqueous solution of 0.5% (w/w); and in particular in an aqueous solution of 0.1% (w/w) of the biocidal agent.

The biocidal agent may also be capable of inhibiting the outgrowth of *Escherichia coli* (DSM 1576) or *Bacillus subtilis* (ATCC 6633) for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

The antimicrobial polypeptide of the invention and the biocidal agent of the composition may be selected so that a synergistic antimicrobial effect is obtained.

The compositions may comprise a suitable carrier material. The compositions may also comprise a suitable delivery vehicle capable of delivering the antimicrobial polypeptides of the invention to the desired locus when the compositions are used as a medicament.

The compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Methods and Uses

The present invention also encompasses various uses of the antimicrobial polypeptides of the invention. The antimicrobial polypeptides are typically useful at any locus subject to contamination by bacteria, fungi, yeast or algae. Typically, loci are in aqueous systems such as cooling water systems, laundry rinse water, oil systems such as cutting oils, lubricants, oil fields and the like, where microorganisms need to be killed or where their growth needs to be controlled. However, the present invention may also be used in all applications for which known antimicrobial compositions are useful, such as protection of wood, latex, adhesive, glue, paper, cardboard, textile, leather, plastics, caulking, and feed.

Other uses include preservation of foods, beverages, cosmetics such as lotions, creams, gels, ointments, soaps, shampoos, conditioners, antiperspirants, deodorants, mouth wash, contact lens products, enzyme formulations, or food ingredients.

Thus, the antimicrobial polypeptides of the invention may by useful as a disinfectant, e.g., in the treatment of acne, infections in the eye or the mouth, skin infections; in antiperspirants or deodorants; in foot bath salts; for cleaning and disinfection of contact lenses, hard surfaces, teeth (oral care), wounds, bruises and the like.

In general it is contemplated that the antimicrobial polypeptides of the present invention are useful for cleaning, disinfecting or inhibiting microbial growth on any hard surface. Examples of surfaces, which may advantageously be contacted with the antimicrobial polypeptides of the invention are surfaces of process equipment used e.g. dairies, chemical or pharmaceutical process plants, water sanitation systems, oil processing plants, paper pulp processing plants, water treatment plants, and cooling towers. The antimicrobial polypeptides of the invention should be used in an amount, which is effective for cleaning, disinfecting or inhibiting microbial growth on the surface in question.

Further, it is contemplated that the antimicrobial polypeptides of the invention can advantageously be used in a cleaning-in-place (C.I.P.) system for cleaning of process equipment of any kind.

The antimicrobial polypeptides of the invention may additionally be used for cleaning surfaces and cooking utensils in food processing plants and in any area in which food is prepared or served such as hospitals, nursing homes, restaurants, especially fast food restaurants, delicatessens and the like. It may also be used as an antimicrobial in food products and would be especially useful as a surface antimicrobial in cheeses, fruits and vegetables and food on salad bars.

It may also be used as a preservation agent or a disinfection agent in water based paints.

The antimicrobial polypeptides of the present invention are also useful for microbial control of water lines, and for disinfection of water, in particular for disinfection of industrial water.

The invention also relates to the use of an antimicrobial polypeptide or composition of the invention as a medicament. Further, an antimicrobial polypeptide or composition of the invention may also be used for the manufacture of a medicament for controlling or combating microorganisms, such as fungal organisms or bacteria, preferably gram positive bacteria.

The composition and antimicrobial polypeptide of the invention may be used as an antimicrobial veterinarian or human therapeutic or prophylactic agent. Thus, the composition and antimicrobial polypeptide of the invention may be used in the preparation of veterinarian or human therapeutic agents or prophylactic agents for the treatment of microbial infections, such as bacterial or fungal infections, preferably gram positive bacterial infections. In particular the microbial infections may be associated with lung diseases including, but not limited to, tuberculosis, pneumonia and cystic fibrosis; and sexual transmitted diseases including, but not limited to, gonorrhea and chlamydia.

The composition of the invention comprises an effective amount of the antimicrobial polypeptide of the invention.

The term "effective amount" when used herein is intended to mean an amount of the antimicrobial polypeptides of the invention, which is sufficient to inhibit growth of the microorganisms in question.

The invention also relates to wound healing compositions or products such as bandages, medical devices such as, e.g., catheters and further to anti-dandruff hair products, such as shampoos.

Formulations of the antimicrobial polypeptides of the invention are administered to a host suffering from or predisposed to a microbial infection. Administration may be topical, localized or systemic, depending on the specific microorganism, preferably it will be localized. Generally the dose of the antimicrobial polypeptides of the invention will be sufficient to decrease the microbial population by at least about 50%, usually by at least 1 log, and may be by 2 or more logs of killing. The compounds of the present invention are administered at a dosage that reduces the microbial population while minimizing any side-effects. It is contemplated that the composition will be obtained and used under the guidance of a physician for in vivo use. The antimicrobial polypeptides of the invention are particularly useful for killing gram negative bacteria, including *Pseudomonas aeruginosa*, and *Chlamydia trachomatis*; and gram-positive bacteria, including various staphylococci and streptococci.

The antimicrobial polypeptides of the invention are also useful for in vitro formulations to kill microbes, particularly where one does not wish to introduce quantities of conventional antibiotics. For example, the antimicrobial polypeptides of the invention may be added to animal and/or human food preparations; or they may be included as an additive for in vitro cultures of cells, to prevent the overgrowth of microbes in tissue culture.

The susceptibility of a particular microbe to killing with the antimicrobial polypeptides of the invention may be determined by in vitro testing, as detailed in the experimental section. Typically a culture of the microbe is combined with the antimicrobial polypeptide at varying concentrations for a period of time sufficient to allow the protein to act, usually between about one hour and one day. The viable microbes are then counted, and the level of killing determined.

Microbes of interest include, but are not limited to, Gram-negative bacteria, for example: *Citrobacter* sp.; *Enterobacter* sp.; *Escherichia* sp., e.g. *E. coli, Klebsiella* sp.; *Morganella* sp.; *Proteus* sp.; *Providencia* sp.; *Salmonella* sp., e.g. *S. typhi, S. typhimurium; Serratia* sp.; *Shigella* sp.; *Pseudomonas* sp., e.g. *P. aeruginosa; Yersinia* sp., e.g. *Y. pestis, Y. pseudotuberculosis, Y. enterocolitica; Franciscella* sp.; *Pasturella* sp.; *Vibrio* sp., e.g. *V. cholerae, V. parahemolyticus; Campylobacter* sp., e.g. *C. jejuni; Haemophilus* sp., e.g. *H. influenzae,* H. ducreyi; *Bordetella* sp., e.g. *B. pertussis, B. bronchiseptica,* B. parapertussis; *Brucella* sp., *Neisseria* sp., e.g. *N. gonorrhoeae, N. meningitidis,* etc. Other bacteria of interest include *Legionella* sp., e.g. *L. pneumophila; Listeria* sp., e.g. *L. monocytogenes; Mycoplasma* sp., e.g. *M. hominis, M. pneumoniae; Mycobacterium* sp., e.g. *M. tuberculosis, M. leprae; Treponema* sp., e.g. *T. pallidum; Borrelia* sp., e.g. *B. burgdorferi; Leptospirae* sp.; *Rickettsia* sp., e.g. *R. rickettsii, R. typhi; Chlamydia* sp., e.g. *C. trachomatis, C. pneumoniae, C. psittaci; Helicobacter* sp., e.g. *H. pylori*, etc.

Non bacterial pathogens of interest include fungal and protozoan pathogens, e.g. *Plasmodia* sp., e.g. *P. falciparum, Trypanosoma* sp., e.g. *T. brucei*; shistosomes; *Entaemoeba* sp., *Cryptococcus* sp., *Candida* sp., e.g. *C. albicans*; etc.

Various methods for administration may be employed. The polypeptide formulation may be given orally, or may be injected intravascularly, subcutaneously, peritoneally, by aerosol, opthalmically, intra-bladder, topically, etc. For example, methods of administration by inhalation are well-known in the art. The dosage of the therapeutic formulation will vary widely, depending on the specific antimicrobial polypeptide to be administered, the nature of the disease, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered once or several times daily, semi-weekly, etc. to maintain an effective dosage level. In many cases, oral administration will require a higher dose than if administered intravenously. The amide bonds, as well as the amino and carboxy termini, may be modified for greater stability on oral administration. For example, the carboxy terminus may be amidated.

Formulations

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, creams, foams, solutions, suppositories, injections, inhalants, gels, microspheres, lotions, and aerosols. As such, administration of the compounds can be achieved in various ways, including oral, buccal, rectal, parenteral, intraperitoneal, intradermal, transdermal, intracheal, etc., administration. The antimicrobial polypeptides of the invention may be systemic after administration or may be localized by the use of an implant or other formulation that acts to retain the active dose at the site of implantation.

In one embodiment, a formulation for topical use comprises a chelating agent that decreases the effective concentration of divalent cations, particularly calcium and magnesium. For example, agents such as citrate, EGTA or EDTA may be included, where citrate is preferred. The concentration of citrate will usually be from about 1 to 10 mM.

The compounds of the present invention can be administered alone, in combination with each other, or they can be used in combination with other known compounds (e.g., perforin, anti-inflammatory agents, antibiotics, etc.) In pharmaceutical dosage forms, the compounds may be administered in the form of their pharmaceutically acceptable salts. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation.

The compounds of the present invention can be formulated into pressurized acceptable propellants such as dichlorodifluoromethane, propane, nitrogen and the like.

The compounds can be used as lotions, for example to prevent infection of burns, by formulation with conventional additives such as solubilizers, isotonic agents, suspending agents, emulsifying agents, stabilizers and preservatives.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well-known in the art. Implants are formulated as microspheres, slabs, etc. with biodegradable or non-biodegradable polymers. For example, polymers of lactic acid and/or glycolic acid form an erodible polymer that is well-tolerated by the host. The implant containing the antimicrobial polypeptides of the invention is placed in proximity to the site of infection, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the unit dosage forms of the present invention depend on the particular compound employed and the effect to be achieved, and the pharmacodynamics associated with the compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Typical dosages for systemic administration range from 0.1 pg to 100 milligrams per kg weight of subject per administration. A typical dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

The use of liposomes as a delivery vehicle is one method of interest. The liposomes fuse with the cells of the target site and deliver the contents of the lumen intracellularly. The liposomes are maintained in contact with the cells for sufficient time for fusion, using various means to maintain contact, such as isolation, binding agents, and the like. In one aspect of the invention, liposomes are designed to be aerosolized for pulmonary administration. Liposomes may be prepared with purified proteins or peptides that mediate fusion of membranes, such as Sendai virus or influenza virus, etc. The lipids may be any useful combination of known liposome forming lipids, including cationic or zwitterionic lipids, such as phosphatidylcholine. The remaining lipid will be normally be neutral or acidic lipids, such as cholesterol, phosphatidyl serine, phosphatidyl glycerol, and the like.

For preparing the liposomes, the procedure described by Kato et al., 1991, J. Biol. Chem. 266: 3361 may be used. Briefly, the lipids and lumen composition containing peptides are combined in an appropriate aqueous medium, conveniently a saline medium where the total solids will be in the range of about 1-10 weight percent. After intense agitation for short periods of time, from about 5-60 sec., the tube is placed in a warm water bath, from about 25-40° C. and this cycle repeated from about 5-10 times. The composition is then sonicated for a convenient period of time, generally from about 1-10 sec. and may be further agitated by vortexing. The volume is then expanded by adding aqueous medium, generally increasing the volume by about from 1-2 fold, followed by shaking and cooling. This method allows for the incorporation into the lumen of high molecular weight molecules.

Formulations with Other Active Agents

For use in the subject methods, the antimicrobial polypeptides of the invention may be formulated with other pharmaceutically active agents, particularly other antimicrobial agents. Other agents of interest include a wide variety of antibiotics, as known in the art. Classes of antibiotics include penicillins, e.g. penicillin G, penicillin V, methicillin, oxacillin, carbenicillin, nafcillin, ampicillin, etc.; penicillins in combination with beta-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc.

Anti-mycotic agents are also useful, including polyenes, e.g. amphotericin B, nystatin; 5-flucosyn; and azoles, e.g. miconazol, ketoconazol, itraconazol and fluconazol. Antituberculotic drugs include isoniazid, ethambutol, streptomycin and rifampin. Cytokines may also be included in a formulation of the antimicrobial polypeptides of the invention, e.g. interferon gamma, tumor necrosis factor alpha, interleukin 12, etc.

In Vitro Synthesis

The antimicrobial peptides of the invention may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulfide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Animal Feed

The present invention is also directed to methods for using the polypeptides having antimicrobial activity in animal feed, as well as to feed compositions and feed additives comprising the antimicrobial polypeptides of the invention.

The term animal includes all animals, including human beings. Examples of animals are non-ruminants, and ruminants, such as cows, sheep and horses. In a particular embodiment, the animal is a non-ruminant animal. Non-ruminant animals include mono-gastric animals, e.g. pigs or swine (including, but not limited to, piglets, growing pigs, and sows); poultry such as turkeys and chicken (including but not limited to broiler chicks, layers); young calves; and fish (including but not limited to salmon).

The term feed or feed composition means any compound, preparation, mixture, or composition suitable for, or intended for intake by an animal.

In the use according to the invention the antimicrobial polypeptide can be fed to the animal before, after, or simultaneously with the diet. The latter is preferred.

In a particular embodiment, the antimicrobial polypeptide, in the form in which it is added to the feed, or when being included in a feed additive, is well defined. Well-defined means that the antimicrobial polypeptide preparation is at least 50% pure as determined by Size-exclusion chromatography (see Example 12 of WO 01/58275). In other particular embodiments the antimicrobial polypeptide preparation is at least 60, 70, 80, 85, 88, 90, 92, 94, or at least 95% pure as determined by this method.

A well-defined antimicrobial polypeptide preparation is advantageous. For instance, it is much easier to dose correctly to the feed an antimicrobial polypeptide that is essentially free from interfering or contaminating other antimicrobial polypeptides. The term dose correctly refers in particular to the objective of obtaining consistent and constant results, and the capability of optimising dosage based upon the desired effect.

For the use in animal feed, however, the antimicrobial polypeptide need not be that pure; it may e.g. include other enzymes, in which case it could be termed an antimicrobial polypeptide preparation.

The antimicrobial polypeptide preparation can be (a) added directly to the feed (or used directly in a treatment process of vegetable proteins), or (b) it can be used in the production of one or more intermediate compositions such as feed additives or premixes that is subsequently added to the feed (or used in a treatment process). The degree of purity described above refers to the purity of the original antimicrobial polypeptide preparation, whether used according to (a) or (b) above.

Antimicrobial polypeptide preparations with purities of this order of magnitude are in particular obtainable using recombinant methods of production, whereas they are not so easily obtained and also subject to a much higher batch-to-batch variation when the antimicrobial polypeptide is produced by traditional fermentation methods.

Such antimicrobial polypeptide preparation may of course be mixed with other enzymes.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

The antimicrobial polypeptide can be added to the feed in any form, be it as a relatively pure antimicrobial polypeptide, or in admixture with other components intended for addition to animal feed, i.e. in the form of animal feed additives, such as the so-called pre-mixes for animal feed.

In a further aspect the present invention relates to compositions for use in animal feed, such as animal feed, and animal feed additives, e.g. premixes.

Apart from the antimicrobial polypeptide of the invention, the animal feed additives of the invention contain at least one fat soluble vitamin, and/or at least one water soluble vitamin, and/or at least one trace mineral, and/or at least one macro mineral.

Further, optional, feed-additive ingredients are coloring agents, aroma compounds, stabilizers, and/or at least one other enzyme selected from amongst phytases EC 3.1.3.8 or 3.1.3.26; xylanases EC 3.2.1.8; galactanases EC 3.2.1.89; and/or beta-glucanases EC 3.2.1.4.

In a particular embodiment these other enzymes are well defined (as defined above for antimicrobial polypeptide preparations).

Examples of other antimicrobial peptides (AMP's) are CAP18, Leucocin A, Tritrpticin, Protegrin-1, Thanatin, Defensin, Ovispirin such as Novispirin (Robert Lehrer, 2000), and variants, or fragments thereof which retain antimicrobial activity.

Examples of other antifungal polypeptides (AFP's) are the Aspergillus giganteus, and Aspergillus niger peptides, as well as variants and fragments thereof which retain antifungal activity, as disclosed in WO 94/01459 and WO 02/090384.

Usually fat and water soluble vitamins, as well as trace minerals form part of a so-called premix intended for addition to the feed, whereas macro minerals are usually separately added to the feed. Either of these composition types, when enriched with an antimicrobial polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat soluble vitamins are vitamin A, vitamin D3, vitamin E, and vitamin K, e.g. vitamin K3.

Examples of water soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterized as indicated in Table B of WO 01/58275, columns 2-3. Fish diets can be characterized as indicated in column 4 of this Table B. Furthermore such fish diets usually have a crude fat content of 200-310 g/kg.

An animal feed composition according to the invention has a crude protein content of 50-800 g/kg, and furthermore comprises at least one antimicrobial polypeptide as claimed herein.

Furthermore, or in the alternative (to the crude protein content indicated above), the animal feed composition of the invention has a content of metabolizable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolizable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolizable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 5-30 mg enzyme protein per kg animal diet.

The antimicrobial polypeptide may be administered in one or more of the following amounts (dosage ranges): 0.01-200; or 0.01-100; or 0.05-100; or 0.05-50; or 0.10-10—all these ranges being in mg antimicrobial polypeptide protein per kg feed (ppm).

For determining mg antimicrobial polypeptide protein per kg feed, the antimicrobial polypeptide is purified from the feed composition, and the specific activity of the purified antimicrobial polypeptide is determined using a relevant assay (see under antimicrobial activity, substrates, and assays). The antimicrobial activity of the feed composition as such is also determined using the same assay, and on the basis of these two determinations, the dosage in mg antimicrobial polypeptide protein per kg feed is calculated.

The same principles apply for determining mg antimicrobial polypeptide protein in feed additives. Of course, if a sample is available of the antimicrobial polypeptide used for preparing the feed additive or the feed, the specific activity is determined from this sample (no need to purify the antimicrobial polypeptide from the feed composition or the additive).

Detergent Compositions

The antimicrobial polypeptides of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the antimicrobial polypeptides of the invention and a surfactant. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase (such as a laccase), and/or a peroxidase (such as a haloperoxidase).

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp.

strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Amylases: Suitable amylases (alpha and/or beta) include those of bacterial or fungal origin. Chemically modified or protein engineered mutants are included. Amylases include, for example, alpha-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora* thermophila and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a H2O2 source such as perborate or percarbonate which may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, and the antimicrobial polypeptides of the invention, may be added in an amount corresponding to 0.01-100 mg of enzyme protein per liter of wash liquor, preferably 0.05-10 mg of enzyme protein per liter of wash liquor, more preferably 0.1-5 mg of enzyme protein per liter of wash liquor, and most preferably 0.1-1 mg of enzyme protein per liter of wash liquor.

The antimicrobial polypeptides of the invention may additionally be incorporated in the detergent formulations disclosed in WO 97/07202 which is hereby incorporated as reference.

The present invention is further described by the following examples which should not be construed as limiting the scope of the invention.

EXAMPLES

Chemicals used as buffers and substrates were commercial products of at least reagent grade.

Example 1

Design, Construction and Evaluation of Synthetic Antimicrobial Peptides

To investigate and design new AMPs with potent antimicrobial activity, a series of putative AMPs were constructed. Three proximal arginines were chosen to precede 6 consecutive 4 amino acid repeats. Based on its membrane-interacting ability and abundance in natural PR-rich peptides, phenylalanine was chosen as the hydrophobic residue ($Z_1$-$Z_{12}$) for the initial series. This resulted in 12 different derivatives having amino acids sequences of SEQ ID NO: 1 to SEQ ID NO: 12.

The 12 genes encoding SEQ ID NO: 1 to SEQ ID NO: 12 were synthesized from 12 specific oligonucleotides (Primer 1 to Primer 12) each encoding one of the peptides. The single-stranded oligonucleotide was turned into double-stranded DNA by polymerization with a complementary primer (Primer 13) by 5 cycles in a standard PCR reaction. A NcoI (underlined) DNA restriction site is located in the proximal part while a XbaI (underlined) restriction site is located in the distal part of the primer—these sites are used for cloning into the corresponding expression vector, pBAD/gIIIA (Invitrogen, USA).

```
Primer 1 - SEQ ID NO: 1 forward (SEQ ID NO: 320):
CCATAGCACC ATGGCGCGTC GCCGTCCGCC ACGTTTTCCA CCTCGTTTTC CACCTCGTTT
CCCTCCACGT TTCCCTCCAC GCTTCCCACC TCGTTTCTAA TTGCTCTAGA ACAAAAACTC Primer 2 - SEQ ID NO: 2 forward (SEQ ID NO: 321):
CCATAGCACC ATGGCGCGTC GCCGTCCACG TTTTCCACCT CGTTTTCCAC CTCGTTTCCC
TCCACGTTTC CCTCCACGCT TCCCACCTCG TTTCCCGTAA TTGCTCTAGA ACAAAAACTC Primer 3 - SEQ ID NO: 3 forward (SEQ ID NO: 322):
CCATAGCACC ATGGCGCGTC GCCGTCGTTT TCCACCTCGT TTTCCACCTC GTTTCCCTCC
ACGTTTCCCT CCACGCTTCC CACCTCGTTT CCCGCCATAA TTGCTCTAGA ACAAAAACTC Primer 4 - SEQ ID NO: 4 forward (SEQ ID NO: 323):
CCATAGCACC ATGGCGCGTC GCCGTTTTCC ACCTCGTTTT CCACCTCGTT TCCCTCCACG
TTTCCCTCCA CGCTTCCCAC CTCGTTTCCC GCCACGTTAA TTGCTCTAGA ACAAAAACTC Primer 5 - SEQ ID NO: 5 forward (SEQ ID NO: 324):
CCATAGCACC ATGGCGCGTC GCCGTCCACG TCCTTTTCCG CGCCCTTTTC CACGTCCATT
CCCTCGTCCT TTCCCACGCC CTTTTCCACG CCCATTCTAA TTGCTCTAGA ACAAAAACTC Primer 6 - SEQ ID NO: 6 forward (SEQ ID NO: 325):
CCATAGCACC ATGGCGCGTC GCCGTCGTCC TTTTCCGCGC CCTTTTCCAC GTCCATTCCC
TCGTCCTTTC CCACGCCCTT TTCCACGCCC ATTCCCATAA TTGCTCTAGA ACAAAAACTC Primer 7 - SEQ ID NO: 7 forward (SEQ ID NO: 326):
CCATAGCACC ATGGCGCGTC GCCGTCCTTT TCCGCGCCCT TTTCCACGTC CATTCCCTCG
TCCTTTCCCA CGCCCTTTTC CACGCCCATT CCCACGTTAA TTGCTCTAGA ACAAAAACTC Primer 8 - SEQ ID NO: 8 forward (SEQ ID NO: 327):
CCATAGCACC ATGGCGCGTC GCCGTTTTCC GCGCCCTTTT CCACGTCCAT TCCCTCGTCC
TTTCCCACGC CCTTTTCCAC GCCCATTCCC ACGTCCTTAA TTGCTCTAGA ACAAAAACTC Primer 9 - SEQ ID NO: 9 forward (SEQ ID NO: 328):
CCATAGCACC ATGGCGCGTC GCCGTCCACC ATTTCGTCCA CCTTTCCGTC CTCCATTTCG
CCCGCCGTTT CGGCCACCGT TTCGACCTCC TTTCCGTTAA TTGCTCTAGA ACAAAAACTC Primer 10 - SEQ ID NO: 10 forward (SEQ ID NO: 329):
CCATAGCACC ATGGCGCGTC GCCGTCCATT TCGTCCACCT TTCCGTCCTC CATTTCGCCC
GCCGTTTCGG CCACCGTTTC GACCTCCTTT CCGTCCATAA TTGCTCTAGA ACAAAAACTC Primer 11 - SEQ ID NO: 11 forward (SEQ ID NO: 330):
CCATAGCACC ATGGCGCGTC GCCGTTTTCG TCCACCTTTC CGTCCTCCAT TTCGCCCGCC
GTTTCGGCCA CCGTTTCGAC CTCCTTTCCG TCCACCATAA TTGCTCTAGA ACAAAAACTC Primer 12- SEQ ID NO: 12 forward (SEQ ID NO: 331):
CCATAGCACC ATGGCGCGTC GCCGTCGTCC ACCTTTCCGT CCTCCATTTC GCCCGCCGTT
TCGGCCACCG TTTCGACCTC CTTTCCGTCC ACCATTTTAA TTGCTCTAGA ACAAAAACTC Primer 13 - reverse (SEQ ID NO: 332):
GAGTTTTTGT TCTAGAGCAA TTA
```

The antibiotic activity of AMPs can be tested in a suicide expression system (SES), as disclosed in Example 1 of International patent application WO 00/73433. This system employs a sensitive host (here *E. coli*) and a plasmid with an inducible promoter (pBAD/gIIIA). If the peptide has antibacterial activity, induction of peptide synthesis will result in growth inhibition and/or cell death of the producing cell—hence suicide expression system. Generally, the stronger the antimicrobial activity, the stronger the inhibition observed.

The 12 double-stranded PCR fragments were purified, restricted with XbaI and NcoI, and cloned into pBAD/gIIIA, which were transformed into *E. coli* TOP10 (Invitrogen), and re-streaked on LB agar plates with 100 micrograms/ml Ampicillin. Individual clones of SEQ ID NO: 1 to SEQ ID NO: 12 was grown in a 100-microwell plate (Honeycomb plate) in 150 microliters RM+0.2% glucose+100 micrograms/ml ampicillin at 37° C. at medium shaking in a Bioscreen C (Thermosystems, Finland).

The overnight cultures were diluted 50-fold in 150 microliters RM+0.2% glycerol+100 ug/ml ampicillin with either 0% or 0.1% inducer (arabinose) in a 100-well honeycomb plate. Cell density was monitored every 30 minutes by measuring at OD450 in a Bioscreen C at 37° C. The percentage of growth inhibition was calculated as the end point OD measurement of each sample divided by the end point OD measurement obtained from cells containing the control vector and multiplied by 100. The formula is the following:

Growth inhibition (%)=(1−(sample *OD*−blank *OD*)/
(control vector *OD*−blank *OD*))×100 where "blank OD" corresponds to the OD of only the growth medium.

The amino acid sequences of the synthetic AMPs and the corresponding growth inhibitions are shown in Table 1.

As expected, no or very little inhibition was observed in the absence of inducer. In the presence of 0.1% inducer all synthetic AMPs resulted in growth inhibition.

Example 2

Expression of Synthetic AMPs in Yeast

The AMPs designated SEQ ID NO: 1, SEQ ID NO: 5 and SEQ ID NO: 10 were cloned into the yeast expression vector pHH3885. Briefly, pHH3885 is a yeast/*E. coli* shuttle vector based on pYES (Invitrogen). This plasmid contains the 2μ yeast replication origin and the Ura3 gene for selection in yeast. For propagation in *E. coli* i the pUC origin and bla gene were used. Expression was controlled by the Gal promoter, and the *S. cerevisiae* alpha-leader was used to mediate secretion of the peptides.

An expression of a potent AMP will kill the producing organism, the antimicrobial activity has to be shielded. This can be done using a stretch of anionic amino acids that will shield the proximal charges that are crucial for antimicrobial activity. Correspondingly, all three AMPs are preceded by a stretch of aspartates and glutamates (DDDDE (SEQ ID NO: 353)). As some proteases specifically cleave after glutamic acid residues (E), the anionic stretch can be liberated from the AMP allowing for monitoring of the antimicrobial activity of the AMP.

The PR-rich AMPs designated SEQ ID NO: 1, SEQ ID NO: 5 and SEQ ID NO: 10 were amplified using the specific Forward primer and the general Reverse primer in a standard PCR reaction. No template is needed as the forward oligo contains all the coding information.

TABLE 1

| SEQ ID NO | Amino acid sequence | Growth inhibition (%) |
|---|---|---|
| Control | TMELEICSWYHMGIRSFLEQKLISEEDLNSAVDHHHHHH | 0 |
| 1 | RRRPPRFPPRFPPRFPPRFPPRFPPRF | 48 |
| 2 | RRRPRFPPRFPPRFPPRFPPRFPPRFP | 45 |
| 3 | RRRRFPPRFPPRFPPRFPPRFPPRFPP | 43 |
| 4 | RRRFPPRFPPRFPPRFPPRFPPRFPPR | 46 |
| 5 | RRRPRPFPRPFPRPFPRPFPRPFPRPF | 57 |
| 6 | RRRRPFPRPFPRPFPRPFPRPFPRPFP | 57 |
| 7 | RRRPFPRPFPRPFPRPFPRPFPRPFPR | 39 |
| 8 | RRRFPRPFPRPFPRPFPRPFPRPFPRP | 38 |
| 9 | RRRPPFRPPFRPPFRPPFRPPFRPPFR | 67 |
| 10 | RRRPFRPPFRPPFRPPFRPPFRPPFRP | 78 |
| 11 | RRRFRPPFRPPFRPPFRPPFRPPFRPP | 73 |
| 12 | RRRRPPFRPPFRPPFRPPFRPPFRPPF | 76 |

```
Primer 14 - SEQ ID NO: 1 forward (SEQ ID NO: 333):
GTATCGATGG CCAAGAGAGA AGCCGACGAT GACGATGAAC GTCGCCGTCC GCCACGTTTT
CCACCTCGTT TTCCACCTCG TTTCCCTCCA CGTTTCCCTC CACGCTTCCC ACCTCGTTTC
TAGATGGCTC TAGAGGGCCG Primer 15 - SEQ ID NO: 5 forward (SEQ ID NO: 334):
GTATCGATGG CCAAGAGAGA AGCCGACGAT GACGATGAAC GTCGCCGTCC ACGTCCTTTT
CCGCGCCCTT TTCCACGTCC ATTCCCTCGT CCTTTCCCAC GCCCTTTTCC ACGCCCATTC
TAGATGGCTC TAGAGGGCCG Primer 16 - SEQ ID NO: 10 forward (SEQ ID NO: 335):
GTATCGATGG CCAAGAGAGA AGCCGACGAT GACGATGAAC GTCGCCGTCC ATTTCGTCCA
CCTTTCCGTC CTCCATTTCG CCCGCCGTTT CGGCCACCGT TTCGACCTCC TTTCCGTCCA
TAGATGGCTC TAGAGGGCCG Primer 17 - reverse (SEQ ID NO: 336):
CGGCCCTCTA GAGCCATCTA
```

The double-stranded PCR fragments were restricted with BalI and XbaI and cloned into pHH3885 restricted with the same two enzymes. The corresponding plasmids were transformed into *E. coli* and sequenced. After sequence-verification, the shuttle-vectors were electro-transformed to *S. cerevisiae* (JG169) and plated on SC+2% glucose+100 micrograms/ml Ampicillin agar plates.

The yeast colonies were re-streaked and grown in 5 ml of liquid SC ground media (supplemented with 2% glucose) at 30° C. for 3 days.

Cells were pelleted by centrifugation at 3500 rpm for 5 minutes. 500 microliters were transferred to microcon YM-3 centrifugational filters (Millipore Corp., USA) and the volume reduced to approximately 20 microliters by centrifugation. The concentrated samples were mixed with Tricine Employing only one type of hydrophobic amino acid is probably not optimal for antimicrobial activity; this is emphasized by natural peptides, that all contain a mix of hydrophobic residues. Degenerate DNA oligos were designed that codes for each of the 4 hydrophobic amino acids instead of being restricted to phenylalanine. In principle, as SEQ ID NO: 1, SEQ ID NO: 5 and SEQ ID NO: 10 each contains 6 phenylalanine residues, the library theoretically can encode 46 or 4096 different variants.

The libraries were constructed as above with one long forward primer encoding the entire peptide (SEQ ID NO: 1 degenerate primer, SEQ ID NO: 5 degenerate primer and SEQ ID NO: 10 degenerate primer) and a smaller reverse primer for synthesis of the reverse strand (Primer 13). N represents 25% of each of the 4 nucleotides (A, C, G, and T) allowing for incorporation of the four hydrophobic amino acids in the designated positions.

```
SEQ ID NO: 1 degenerate primer (SEQ ID NO: 337)
CCATAGCACC ATGGCGCGTC GCCGTCCGCC ACGTNTTCCA CCTCGTNTTC CACCTCGTNT
CCCTCCACGT NTCCCTCCAC GCNTCCCACC TCGTNTCTAA TTGCTCTAGA ACAAAAACTC SEQ ID NO: 5 degenerate primer (SEQ ID NO: 338)
CCATAGCACC ATGGCGCGTC GCCGTCCACG TCCTNTTCCG CGCCCTNTTC CACGTCCANT
CCCTCGTCCT NTCCCACGCC CTNTTCCACG CCCANTCTAA TTGCTCTAGA ACAAAAACTC SEQ ID NO: 10 degenerate primer (SEQ ID NO: 339)
CCATAGCACC ATGGCGCGTC GCCGTCCANT TCGTCCACCT NTCCGTCCTC CANTTCGCCC
GCCGNTTCGG CCACCGNTTC GACCTCCTNT CCGTCCATAA TTGCTCTAGA ACAAAAACTC
``` loading buffer and analyzed in 16% Tricine gels (Novex, Invitrogen, USA).

Distinct bands with the expected molecular weight were observed in each of the three cultures indicating expression of the three peptides. No bands were observed in supernatants of yeast cells harboring the control plasmid.

Example 3

Evaluation of Variants of SEQ ID NO: 1, SEQ ID NO: 5 and SEQ ID NO: 10

SEQ ID NO: 1, SEQ ID NO: 5 and SEQ ID NO: 10 were used as a starting point in a mutational high throughput screening for obtaining AMPs with improved activity. For simplicity SEQ ID NO: 1, SEQ ID NO: 5 and SEQ ID NO: 10 all contained phenylalanine as the hydrophobic residue.

The DNA fragments were cloned into the SES vector pBAD/gIIIA and transformed into *E. coli* to give three independent libraries of approximately a million colonies each.

The libraries were plated and around 10,000 individual colonies from each library were picked into 96-well microtiter plates containing 20× diluted RM+200 micrograms/ml Ampicillin by a colony picker. These master plates were replica-plated into a new set of 96-well plates containing 20× diluted RM media and either 0.1% or 0% inducer and incubated overnight at 37° C. A number of the most growth inhibited clones from each library were isolated, sequenced and re-tested for growth inhibition in the Bioscreen C.

The amino acid sequences of the variants of SEQ ID NO: 1 and the corresponding growth inhibitions are shown in Table 2; variants of SEQ ID NO: 5 are shown in Table 3; and variants of SEQ ID NO: 10 are shown in Table 4.

TABLE 2

Variants of SEQ ID NO: 1 and the corresponding growth inhibitions.

| SEQ ID NO | Amino acid sequence | Growth inhibition (%) |
|---|---|---|
| 13 | RRRPPRFPPRFPPRFPPRFPPRF | 51 |
| 14 | RRRPPRFPPRIPPRFPPRLPPRIPPRL | 90 |
| 15 | RRRPPRFPPRIPPRLPPRVPPRVPPRL | 57 |
| 16 | RRRPPRIPPRFPPRVPPRFPPRVPPRV | 98 |
| 17 | RRRPPRIPPRLPPRIPPRFPPRFPPRL | 95 |
| 18 | RRRPPRLPPRFPPRFPPRIPPRFPPRT | 99 |
| 19 | RRRPPRLPPRFPPRFPPRIPPRFPPRI | 78 |
| 20 | RRRPPRLPPRFPPRFPPRVPPRFPPRV | 86 |
| 21 | RRRPPRLPPRFPPRFPPRVPPRFPPRV | 86 |
| 22 | RRRPPRLPPRFPPRFPPRVPPRLPPRF | 81 |
| 23 | RRRPPRLPPRFPPRFPPRVPPRVPPRF | 82 |
| 24 | RRRPPRLPPRFPPRFPPRVPPRVPPRF | 90 |
| 25 | RRRPPRLPPRFPPRFPPRVPPRVPPRI | 81 |
| 26 | RRRPPRVPPRFPPRVPPRFPPRVPLRL | 86 |
| 27 | RRRPPRLPPRLPPRLPPRVPPRVPLVSNCSRTKTHLRRGSE | 90 |

TABLE 3

Variants of SEQ ID NO: 5 and the corresponding growth inhibitions.

| SEQ ID NO | Amino acid sequence | Growth inhibition (%) |
|---|---|---|
| 28 | RRRPRPFPRPFPRPFPRPFPRPFPRPF | 57 |
| 29 | RRRPRLPRPFPRPVPRPLPRPVPRPI | 63 |
| 30 | RRRPRPFPPPFPRPIPRPFPRPFPRPL | 61 |
| 31 | RRRPRPFPRPFPHPFPRPFPRPIPRPI | 73 |
| 32 | RRRPRPFPRPFPHPIPRPLPRPFPRPI | 77 |
| 33 | RRRPRPFPRPFPRPFPRPFPRPFPRPF | 79 |
| 34 | RRRPRPFPRPFPRPFPRPFPRPFPRPL | 74 |
| 35 | RRRPRPFPRPFPRPFPRPFPRPIPRPF | 78 |
| 36 | RRRPRPFPRPFPRPFPRPFPRPIPRPI | 77 |
| 37 | RRRPRPFPRPFPRPFPRPIPRPFPRPV | 68 |
| 38 | RRRPRPFPRPFPRPFPRPIPRPVPRPI | 64 |
| 39 | RRRPRPFPRPFPRPFPRPLPRPFPRPF | 56 |
| 40 | RRRPRPFPRPFPRPFPRPVPRPLPRPI | 69 |
| 41 | RRRPRPFPRPFPRPFPRPVPRPLPRPV | 71 |
| 42 | RRRPRPFPRPFPRPIPRPFPRPLPRPI | 66 |
| 43 | RRRPRPFPRPFPRPIPRPFPRPVPRPV | 68 |
| 44 | RRRPRPFPRPFPRPLPRPFPRPVPRPF | 95 |

TABLE 3-continued

Variants of SEQ ID NO: 5 and the corresponding growth inhibitions.

| SEQ ID NO | Amino acid sequence | Growth inhibition (%) |
|---|---|---|
| 45 | RRRPRPFPRPFPRPLPRPTPRPFPRPV | 69 |
| 46 | RRRPRPFPRPFPRPVPRPFPRPFPRPI | 84 |
| 47 | RRRPRPFPRPFPRPVPRPIPRPFPRPF | 92 |
| 48 | RRRPRPFPRPFPRPVPRPVPRPVPRPF | 59 |
| 49 | RRRPRPFPRPLPRPVPRPFPRPVPRPL | 51 |
| 50 | RRRPRPFPRPLPRPVPRPFPRPVPRPV | 69 |
| 51 | RRRPRPFPRPVPRPFPRPFPRPFPRPF | 77 |
| 52 | RRRPRPFPRPVPRPIPRPFPRPVPRPF | 53 |
| 53 | RRRPRPFPRPVPRPIPRPFPRPVPRPV | 62 |
| 54 | RRRPRPFPRPVPRPVPRPFPRPIPRPL | 65 |
| 55 | RRRPRPFPRPVPRPVPRPFPRPLPRPI | 63 |
| 56 | RRRPRPIPRPFPRPFPRPFPRPFPRPI | 51 |
| 57 | RRRPRPIPRPFPRPTPRPIPRPFPRPF | 73 |
| 58 | RRRPRPIPRPFPRPIPRPVPRPFPRPF | 77 |
| 59 | RRRPRPIPRPFPRPIPRPVPRPFPRPF | 75 |
| 60 | RRRPRPIPRPFPRPVPRPVPRPFPRPF | 70 |
| 61 | RRRPRPVPRPFPRPVPRPLPRPFPRPF | 97 |
| 62 | RRRPRPIPRPIPRPFPRPFPRPFHAQSNCSRTKTHLRRGSE | 77 |
| 63 | RRRPRPFPRPFPRPVPRPFPRPFPRQSNCSRTKTHLRRGSE | 80 |

TABLE 4

Variants of SEQ ID NO: 10 and the corresponding growth inhibitions.

| SEQ ID NO | Amino acid sequence | Growth inhibition (%) |
|---|---|---|
| 64 | RRRPFRPPFRPPFRPPFRPPFRPPFRP | 82 |
| 65 | RRRPLRPPLRPPVRPPVRPPFRPPFRP | 89 |
| 66 | RRRPFRPPFRPPFRPPIRPPLRPPIRP | 76 |
| 67 | RRRPLRPPLRPPIRPPFRPPVRPPFRP | 80 |
| 68 | RRRPIRPPFRPPFRPPLRPPVRPPFRP | 78 |
| 69 | RRRPIRPPFRPPFRPPLRPPFRPPIRP | 75 |
| 70 | RRRPLRPPLRPPFRPPIRPPLRPPFRP | 76 |
| 71 | RRRPLRPPTRPPFRPPIRPPFRPPFRP | 82 |
| 72 | RRRPIRPPFRPPFRPPFRPPFRPPFRP | 49 |
| 73 | RRRPFRPPVRPPFRPPVRPPIRPPVRP | 65 |
| 74 | RRRPFRPPVRPPFRPPFRPPIRPPIRP | 76 |
| 75 | RRRPFRPPIRPPVRPPFRPPFRPPFRP | 79 |
| 76 | RRRPIRPPFRPPIRPPVRPPFRPPIRP | 86 |
| 77 | RRRPFRPPFRPPTRPPVRPPFRPPFRP | 72 |
| 78 | RRRPLRPPFRPPFRPPFRPPIRPPVRP | 83 |
| 79 | RRRPFRPPFRPPFRPPVRPPVRPPFRP | 82 |
| 80 | RRRPFRPPFRPPIRPPVRPPVRPPFRP | 81 |
| 81 | RRRPFRPPIRPPFRPPFRPPVRPPIRP | 80 |
| 82 | RRRPIRPPFRPPVRPPFRPPFRPPFRP | 71 |
| 83 | RRRPLRPPFRPPIRPPVRPPFRPPVRP | 72 |
| 84 | RRRPIRPPLRPPIRPPFRPPFRPPLRP | 80 |
| 85 | RRRPFRPPTRPPIRPPFRPPFRPPIRP | 67 |
| 86 | RRRPIRPPFRPPLRPPLRPPVRPPFRP | 74 |
| 87 | RRRPFRPPFRPPIRPPFRPPVRPPVRP | 80 |

TABLE 4-continued

Variants of SEQ ID NO: 10 and the corresponding growth inhibitions.

| SEQ ID NO | Amino acid sequence | Growth inhibition (%) |
|---|---|---|
| 88 | RRRPFRPPLRPPLRPPVRPPVRPPFRP | 82 |
| 89 | RRRPFRPPFRPPFRPPVRPPVRPPLRP | 70 |
| 90 | RRRPFRPPIRPPFRPPFRPPVRPPFRP | 74 |
| 91 | RRRPFRPPVRPPIRPPVRPPFRPPVRP | 52 |
| 92 | RRRPVRPPIRPPFRPPFRPPFRPPFRP | 85 |
| 93 | RRRPFRPPFRPPFRPPVRPPLRPPIRP | 61 |
| 94 | RRRPFRPPVRPPIRPPVRPPFRPPFRP | 77 |
| 95 | RRRPFRPPLRPPLRPPTRPPVRPPFRP | 80 |
| 96 | RRRPFRPPIRPPFRPPIRPPLRPPIRP | 71 |
| 97 | RRRPLRPPFRPPFRPPLRPPFRPPIRP | 69 |
| 98 | RRRPFRPPFRPPVRPPTRPPLRPPFRP | 63 |
| 99 | RRRPFRPPIRPPIRPPFRPPIRPPFRP | 79 |
| 100 | RRRPIRPPFRPPFRPPFRPPFRPPFRP | 84 |
| 101 | RRRPIRPPFRPPLRPPFRPPIRPPIRP | 81 |
| 102 | RRRPTRPPFRPPTRPPFRPPLRPPFRP | 77 |
| 103 | RRRPLRPPIRPPIRPPVRPPFRPPTRP | 73 |
| 104 | RRRPFRPPFRPPIRPPFRPPFRPPLRP | 76 |
| 105 | RRRPIRPPLRPPLRPPFRPPFRPPFRP | 73 |
| 106 | RRRPFRPPFRPPFRPPIRPPIRPPLRP | 75 |
| 107 | RRRPFRPPFRPPVRPPFRPPIRPPFRP | 69 |
| 108 | RRRPLRPPFRPPTRPPVRPPVRPPFRP | 76 |
| 109 | RRRPFRPPIRPPVRPPLRPPVRPPFRP | 71 |
| 110 | RRRPFRPPLRPPFRPPIRPPIRPPVRP | 73 |
| 111 | RRRPLRPPVRPPFRPPVRPPLRPPFRP | 59 |
| 112 | RRRPFRPPIRPPFRPPVRPPVRPPVRP | 69 |
| 113 | RRRPLRPPVRPPFRPPVRPPFRPPFRP | 75 |
| 114 | RRRPLRPPLRPPFRPPLRPPFRPPFRP | 74 |
| 115 | RRRPLRPPFRPPIRPPFRPPFRPPFRP | 79 |
| 116 | RRRPIRPPFRPPFRPPVRPPIRPPFRP | 69 |
| 117 | RRRPIRPPIRPPFRPPFRPPTRPPFRP | 77 |
| 118 | RRRPFRPPFRPPLRPPFRPPVRPPLRP | 73 |
| 119 | RRRPIRPPFRPPIRPPFRPPVRPPVRP | 69 |
| 120 | RRRPLRPPFRPPFRPPFRPPVRPPIRP | 68 |
| 121 | RRRPIRPPLRPPVRPPIRPPFRPPFRP | 65 |
| 122 | RRRPFRPPFRPPFRPPVRPPFRPPLRP | 64 |
| 123 | RRRPFRPPLRPPIRPPIRPPFRPPFRP | 65 |
| 124 | RRRPFRPPIRPPLRPPVRPPLRPPFRP | 73 |
| 125 | RRRPIRPPFRPPLRPPFRPPVRPPVRP | 73 |
| 126 | RRRPIRPPIRPPLRPPFRPPFRPPFRP | 77 |
| 127 | RRRPIRPPFRPPLRPPFRPPFRPPLRP | 67 |
| 128 | RRRPFRPPFRPPLRPPFRPPVRPPLRP | 69 |
| 129 | RRRPFRPPFRPPVRPPFRPPIRPPLRP | 69 |
| 130 | RRRPFRPPIRPPLRPPFRPPVRPPLRP | 78 |
| 131 | RRRPIRPPFRPPFRPPIRPPIRPPVRP | 75 |
| 132 | RRRPFRPPFRPPLRPPVRPPVRPPTRP | 72 |
| 133 | RRRPFRPPIRPPFRPPVRPPIRPPVRP | 62 |
| 134 | RRRPFRPPFRPPFRPPVRPPLRPPVRP | 68 |
| 135 | RRRPIRPPIRPPIRPPIRPPIRPPLRP | 38 |
| 136 | RRRPFRPPFRPPIRPPFRPPIRPPLRP | 77 |
| 137 | RRRPLRPPFRPPFRPPIRPPFRPPVRP | 58 |
| 138 | RRRPLRPPFRPPVRPPFRPPFRPPFRP | 78 |
| 139 | RRRPFRPPFRPPTRPPFRPPIRPPVRP | 67 |
| 140 | RRRPIRPPIRPPFRPPVRPPVRPPFRP | 70 |
| 141 | RRRPIRPPIRPPFRPPFRPPLRPPTRP | 65 |
| 142 | RRRPLRPPIRPPVRPPFRPPVRPPFRP | 70 |
| 143 | RRRPFRPPVRPPVRPPFRPPLRPPVRP | 43 |
| 144 | RRRPIRPPLRPPVRPPVRPPFRPPFRP | 64 |
| 145 | RRRPLRPPVRPPFRPPFRPPLRPPFRP | 59 |
| 146 | RRRPLRPPFRPPIRPPFRPPFRPPLRP | 68 |
| 147 | RRRPFRPPFRPPIRPPVRPPVRPPFRP | 79 |
| 148 | RRRPIRPPFRPPFRPPFRPPFRPPLRP | 76 |
| 149 | RRRPIRPPIRPPFRPPFRPPVRPPVRP | 62 |
| 150 | RRRPIRPPIRPPFRPPIRPPFRPPVRP | 68 |
| 151 | RRRPLRPPVRPPLRPPVRPPFRPPFRP | 68 |
| 152 | RRRPFRPPFRPPFRPPFRPPVRPPIRP | 75 |
| 153 | RRRPIRPPFRPPIRPPVRPPIRPPFRP | 68 |
| 154 | RRRPFRPPFRPPVRPPVRPPFRPPFRP | 75 |
| 155 | RRRPFRPPFRPPFRPPFRPPFRPPLRP | 83 |
| 156 | RRRPFRPPLRPPFRPPFRPPIRPPFRP | 67 |
| 157 | RRRPIRPPFRPPIRPPFRPPVRPPLRP | 64 |
| 158 | RRRPIRPPFRPPIRPPIRPPIRPPVRP | 67 |
| 159 | RRRPVRPPTRPPIRPPVRPPLRPPVRP | 35 |
| 160 | RRRPFRPPVRPPFRPPVRPPFRPPFRP | 77 |

TABLE 4-continued

Variants of SEQ ID NO: 10 and the corresponding growth inhibitions.

| SEQ ID NO | Amino acid sequence | Growth inhibition (%) |
|---|---|---|
| 161 | RRRPFRPPVRPPIRPPVRPPFRPPFRP | 78 |
| 162 | RRRPFRPPTRPPFRPPFRPPLRPPLRP | 68 |
| 163 | RRRPIRPPFRPPFRPPFRPPIRPPIRP | 79 |
| 164 | RRRPFRPPIRPPLRPPFRPPFRPPFRP | 78 |
| 165 | RRRPFRPPLRPPFRPPVRPPLRPPVRP | 65 |
| 166 | RRRPLRPPVRPPFRPPVRPPVRPPLRP | 55 |
| 167 | RRRPFRPPLRPPFRPPLRPPLRPPVRP | 58 |
| 168 | RRRPLRPPFRPPIRPPVRPPLRPPFRP | 71 |
| 169 | RRRPIRPPLRPPVRPPFRPPVRPPFRP | 67 |
| 170 | RRRPIRPPFRPPFRPPFRPPVRPPFRP | 80 |
| 171 | RRRPIRPPIRPPIRPPTRPPFRPPFRP | 77 |
| 172 | RRRPFRPPIRPPFRPPIRPPVRPPFRP | 82 |
| 173 | RRRPLRPPIRPPLRPPVRPPFRPPFRP | 81 |
| 174 | RRRPIRPPIRPPFRPPLRPPFRPPFRP | 80 |
| 175 | RRRPFRPPVRPPFRPPLRPPFRPPFRP | 77 |
| 176 | RRRPLRPPVRPPTRPPIRPPFRPPFRP | 81 |
| 177 | RRRPFRPPIRPPFRPPIRPPVRPPIRP | 75 |
| 178 | RRRPLRPPFRPPVRPPFRPPFRPPFRP | 81 |
| 179 | RRRPFRPPIRPPIRPPFRPPFRPPFRP | 87 |
| 180 | RRRPLRPPIRPPIRPPIRPPFRPPFRP | 76 |
| 181 | RRRPIRPPTRPPFRPPFRPPFRPPFRP | 83 |
| 182 | RRRPFRPPIRPPFRPPIRPPVRPPFRP | 83 |
| 183 | RRRPFRPPVRPPLRPPFRPPFRPPFRP | 80 |
| 184 | RRRPIRPPIRPPFRPPLRPPFRPPFRP | 78 |
| 185 | RRRPLRPPIRPPIRPPFRPPFRPPFRP | 79 |
| 186 | RRRPIRPPIRPPIRPPFRPPFRPPFRP | 77 |
| 187 | RRRPTRPPFRPPFRPPVRPPFRPPFRP | 85 |
| 188 | RRRPFRPPFRPPIRPPVRPPVRPPFRP | 83 |
| 189 | RRRPFRPPFRPPIRPPVRPPIRPPFRP | 79 |
| 190 | RRRPFRPPIRPPFRPPIRPPFRPPFRP | 83 |
| 191 | RRRPFRPPFRPPIRPPFRPPVRPPFRP | 77 |
| 192 | RRRPFRPPFRPPFRPPVRPPVRPPFRP | 92 |
| 193 | RRRPFRPPIRPPFRPPIRPPFRPPFRP | 81 |
| 194 | RRRPLRPPFRPPFRPPIRPPFRPPFRP | 81 |
| 195 | RRRPFRPPIRPPFRPPVRPPVRPPVRP | 76 |
| 196 | RRRPFRPPLRPPIRPPIRPPFRPPFRP | 77 |
| 197 | RRRPFRPPFRPPFRPPFRPPLRPPFRP | 86 |
| 198 | RRRPFRPPFRPPFRPPFRPPFRPPFRP | 91 |
| 199 | RRRPLRPPIRPPFRPPVRPPFRPPFRP | 80 |
| 200 | RRRPFRPPFRPPLRPPFRPPVRPPFRP | 87 |
| 201 | RRRPFRPPTRPPIRPPFRPPTRPPFRP | 78 |
| 202 | RRRPFRPPFRPPFRPPLRPPFRPPFRP | 84 |
| 203 | RRRPFRPPIRPPFRPPTRPPFRPPFRP | 79 |
| 204 | RRRPLRPPLRPPFRPPIRPPFRPPFRP | 76 |
| 205 | RRRPFRPPFRPPIRPPVRPPFRPPFRP | 77 |
| 206 | RRRPFRPPFRPPFRPPFRPPFRPPFRP | 77 |

Example 4

Evaluation of Synthetic PR-Rich AMPs from a Mixed-Motif Library

The AMPs tested in Example 3 consisted of degenerate but otherwise identical repeats. To test whether the 12 different "4 amino acid sequence motifs" when mixed in one sequence would give rise to potent AMPs, a new library was constructed. The parent backbone in this series was composed of the following sequence motifs: PPRX, PRPX, PXRP, PPRX, PRPX and PXRP; where X denotes any of the hydrophobic amino acids valine, phenylalamine, isoleucine or leucine. Again, an equal ratio of hydrophobic amino acids was used.

The library was constructed as in Example 3 above with one long forward primer encoding the entire peptide (Mixed-motif degenerate primer) and a smaller reverse primer for synthesis of the reverse strand (Primer 13). N represents 25% of each of the 4 nucleotides (A, C, G, and T).

```
Mixed-motif degenerate primer (SEQ ID NO: 340)
CCATAGCACC ATGGCGCGTC GCCGTCCGCC ACGTNTTCCA CGTCCTNTTC CANTTCGTCC

ACCGCCACGT NTTCCACGTC CTNTTCCANT TCGTCCATAA TTGCTCTAGA ACAAAAACTC
```

The PCR synthesized DNA fragments were cloned into the SES vector pBAD/gIIIA and transformed into *E. coli* to a library of approximately a million colonies each.

The library was plated and around 10,000 individual colonies were picked into 96-well microtiter plates containing 20× diluted RM+200 micrograms/ml Ampicillin by a colony picker. These master plates were replica-plated into a new set of 96-well plates containing 20× diluted RM media and either 0.1% or 0% inducer and incubated overnight at 37° C. A number of the most growth inhibited clones were isolated, sequenced and re-tested for growth inhibition in the Bioscreen C.

The amino acid sequences of the variants from the mixed-motif library and the corresponding growth inhibitions are shown in Table 5.

TABLE 5

Synthetic PR-rich AMPs with a mixed-motif.

| SEQ ID NO | Amino acid sequence | Growth inhibition (%) |
|---|---|---|
| 207 | RRRPPRFPRPFPIRPPPRFPRPIPFRP | 93 |
| 208 | RRRPPRFPRPFPVRPPPRFPRPIPVRP | 95 |
| 209 | RRRPPRIPRPFPIRPPPRFPRPIPFRP | 78 |
| 210 | RRRPPRIPRPIPVRPPPRTPRPIPFRP | 94 |
| 211 | RRRPPRLPRPFPFRPPPRFPRPIPFRP | 96 |
| 212 | RRRPPRLPRPFPFRPPPRFPRPVPIRP | 96 |
| 213 | RRRPPRLPRPFPFRPPPRLPRPFPIRP | 94 |
| 214 | RRRPPRLPRPFPFRPPPRLPRPIPLRP | 95 |
| 215 | RRRPPRLPRPFPFRPPPRPRPFPFRP | 94 |
| 216 | RRRPPRLPRPFPFRPPPRPRPLPVRP | 95 |
| 217 | RRRPPRLPRPFPFRPPPRVPRPFPLRP | 93 |
| 218 | RRRPPRLPRPFPFRPPPRVPRPIPVRP | 93 |
| 219 | RRRPPRLPRPFPFRPPPRVPRPLPFRP | 93 |
| 220 | RRRPPRLPRPFPIRPPPRFPRPFPVRP | 90 |
| 221 | RRRPPRLPRPFPIRPPPRFPRPLPFRP | 93 |
| 222 | RRRPPRLPRPFPIRPPPRFPRPVPLRP | 93 |
| 223 | RRRPPRLPRPFPIRPPPRLPRPLPFRP | 90 |
| 224 | RRRPPRLPRPFPIRPPPRVPRPFPVRP | 93 |
| 225 | RRRPPRLPRPFPIRPPPRVPRPIPIRP | 97 |
| 226 | RRRPPRLPRPFPIRPPPRVPRPTPVRP | 94 |
| 227 | RRRPPRLPRPFPIRPPPRVPRPVPIRP | 94 |
| 228 | RRRPPRLPRPFPLRPPPRFPRPFPIRP | 96 |
| 229 | RRRPPRLPRPFPLRPPPRFPRPFPLRP | 95 |
| 230 | RRRPPRLPRPFPLRPPPRFPRPLPLRP | 94 |
| 231 | RRRPPRLPRPFPLRPPPRLPRPFPFRP | 98 |
| 232 | RRRPPRLPRPFPLRPPPRLPRPIPVRP | 92 |
| 233 | RRRPPRLPRPFPLRPPPRLPRPLPVRP | 91 |
| 234 | RRRPPRLPRPFPLRPPPRVPRPLPIRP | 93 |
| 235 | RRRPPRLPRPFPLRPPPRVPRPVPFRP | 94 |
| 236 | RRRPPRLPRPFPLRPPPRVPRPVPFRP | 91 |
| 237 | RRRPPRLPRPFPLRPPPRVPRPVPVRP | 96 |
| 238 | RRRPPRLPRPFPVRPPPRFPRPFPIRP | 95 |

TABLE 5-continued

Synthetic PR-rich AMPs with a mixed-motif.

| SEQ ID NO | Amino acid sequence | Growth inhibition (%) |
|---|---|---|
| 239 | RRRPPRLPRPFPVRPPPRFPRPFPLRP | 99 |
| 240 | RRRPPRLPRPFPVRPPPRFPRPVPFRP | 91 |
| 241 | RRRPPRLPRPFPVRPPPRIPRPIPFRP | 96 |
| 242 | RRRPPRLPRPFPVRPPPRLPRPVPFRP | 90 |
| 243 | RRRPPRLPRPFPVRPPPRLPRPVPFRP | 91 |
| 244 | RRRPPRLPRPFPVRPPPRLPRPVPFRP | 90 |
| 245 | RRRPPRLPRPFPVRPPPRVPRPFPVRP | 95 |
| 246 | RRRPPRLPRPFPVRPPPRVPRPFPVRP | 95 |
| 247 | RRRPPRLPRPFPVRPPPRVPRPLPFRP | 93 |
| 248 | RRRPPRLPRPFPVRPPPRVPRPVPIRP | 94 |
| 249 | RRRPPRLPRPFPVRPPPRVPRPVPIRP | 93 |
| 250 | RRRPPRLPRPIPFRPPPRIPRPIPVRP | 96 |
| 251 | RRRPPRLPRPTPFRPPPRTPRPLPFRP | 96 |
| 252 | RRRPPRLPRPIPFRPPPRIPRPVPVRP | 92 |
| 253 | RRRPPRLPRPIPFRPPPRLPRPIPIRP | 91 |
| 254 | RRRPPRLPRPIPFRPPPRVPRPFPIRP | 77 |
| 255 | RRRPPRLPRPIPIRPPPRFPRPVPFRP | 93 |
| 256 | RRRPPRLPRPIPLRPPPRVPRPIPIRP | 91 |
| 257 | RRRPPRLPRPIPVRPPPRFPRPIPFRP | 92 |
| 258 | RRRPPRLPRPIPVRPPPRFPRPIPFRP | 92 |
| 259 | RRRPPRLPRPIPVRPPPRFPRPIPVRP | 98 |
| 260 | RRRPPRLPRPIPVRPPPRIPRPIPVRP | 90 |
| 261 | RRRPPRLPRPIPVRPPPRIPRPVPFRP | 92 |
| 262 | RRRPPRLPRPIPVRPPPRLPRPVPLRP | 93 |
| 263 | RRRPPRLPRPIPVRPPPRVPRPIPLRP | 94 |
| 264 | RRRPPRLPRPLPFRPPPRFPRPVPVRP | 92 |
| 265 | RRRPPRLPRPLPFRPPPRLPRPFPVRP | 94 |
| 266 | RRRPPRLPRPLPFRPPPRLPRPVPVRP | 94 |
| 267 | RRRPPRLPRPLPFRPPPRVPRPFPIRP | 94 |
| 268 | RRRPPRLPRPLPFRPPPRVPRPVPLRP | 93 |
| 269 | RRRPPRLPRPLPFRPPPRVPRPVPVRP | 90 |
| 270 | RRRPPRLPRPLPFRPPPRVPRPVPVRP | 90 |
| 271 | RRRPPRLPRPLPFRPPPRVPRPVPVRP | 97 |
| 272 | RRRPPRLPRPLPIRPPPRFPRPIPVRP | 91 |
| 273 | RRRPPRLPRPLPIRPPPRFPRPVPLRP | 92 |
| 274 | RRRPPRLPRPLPIRPPPRFPRPVPVRP | 93 |
| 275 | RRRPPRLPRPLPIRPPPRLPRPFPVRP | 92 |
| 276 | RRRPPRLPRPLPTRPPPRLPRPVPVRP | 94 |

TABLE 5-continued

Synthetic PR-rich AMPs with a mixed-motif.

| SEQ ID NO | Amino acid sequence | Growth inhibition (%) |
|---|---|---|
| 277 | RRRPPRLPRPLPIRPPPRVPRPFPIRP | 91 |
| 278 | RRRPPRLPRPLPIRPPPRVPRPLPFRP | 98 |
| 279 | RRRPPRLPRPLPIRPPPRVPRPLPLRP | 91 |
| 280 | RRRPPRLPRPLPLRPPPRFPRPFPVRP | 97 |
| 281 | RRRPPRLPRPLPLRPPPRFPRPVPLRP | 91 |
| 282 | RRRPPRLPRPLPLRPPPRLPHPIPFRP | 95 |
| 283 | RRRPPRLPRPLPVRPPPRFPRPVPFRP | 95 |
| 284 | RRRPPRLPRPLPVRPPPRFPRPVPVRP | 89 |
| 285 | RRRPPRLPRPLPVRPPPRIPRPFPVRP | 91 |
| 286 | RRRPPRLPRPLPVRPPPRIPRPLPLRP | 95 |
| 287 | RRRPPRLPRPLPVRPPPRLPRPIPIRP | 94 |
| 288 | RRRPPRLPRPLPVRPPPRVPRPFPLRP | 96 |
| 289 | RRRPPRLPRPLPVRPPPRVPRPFPVRP | 95 |
| 290 | RRRPPRLPRPLPVRPPPRVPRPLPLRP | 94 |
| 291 | RRRPPRLPRPLPVRPPPRVPRPVPFRP | 90 |
| 292 | RRRPPRLPRPLPVRPPPRVPRPVPFRP | 93 |
| 293 | RRRPPRLPRPVPFRPPPRFPRPFPIRP | 93 |
| 294 | RRRPPRLPRPVPFRPPPRFPRPVPLRP | 95 |
| 295 | RRRPPRLPRPVPFRPPPRTPRPFPLRP | 59 |
| 296 | RRRPPRLPRPVPFRPPPRVPRPIPFRP | 88 |
| 297 | RRRPPRLPRPVPFRPPPRVPRPIPVRP | 90 |
| 298 | RRRPPRLPRPVPFRPPPRVPRPVPLRP | 92 |
| 299 | RRRPPRLPRPVPIRPPPRFPRPIPFRP | 96 |
| 300 | RRRPPRLPRPVPIRPPPRTPRPIPFRP | 92 |
| 301 | RRRPPRLPRPVPIRPPPRVPRPVPLRP | 92 |
| 302 | RRRPPRLPRPVPLRPPPRFPRPVPVRP | 82 |
| 303 | RRRPPRLPRPVPLRPPPRVPRPLPIRP | 91 |
| 304 | RRRPPRLPRPVPVRPPPRFPRPVPIRP | 90 |
| 305 | RRRPPRLPRPVPVRPPPRFPRPVPVRP | 90 |
| 306 | RRRPPRLPRPVPVRPPPRFPRPVPVRP | 90 |
| 307 | RRRPPRLPRPVPVRPPPRVPRPVPFRP | 92 |
| 308 | RRRPPRLPRPVPVRPPPRVPRPVPVRP | 96 |
| 309 | RRRPPRVPRPFPIRPPPRVPRPIPFRP | 76 |
| 310 | RRRPPRVPRPFPIRPPPRVPRPVPVRP | 93 |
| 311 | RRRPPRVPRPFPVRPPPRFPRPVPFRP | 96 |
| 312 | RRRPPRVPRPIPIRPPPRVPRPVPFRP | 93 |

TABLE 5-continued

Synthetic PR-rich AMPs with a mixed-motif.

| SEQ ID NO | Amino acid sequence | Growth inhibition (%) |
|---|---|---|
| 313 | RRRPPRVPRPIPTRPPPRVPRPVPVRP | 92 |
| 314 | RRRPPRVPRPLPFRPPPRFPRPIPFRP | 94 |
| 315 | RRRPPRVPRPVPVRPPPRIPRPFPVRP | 98 |
| 316 | RRRTRHVFARPFPFRPPPRIPRPFPLRP | 97 |
| 317 | RRRTRHVFARPVPVRPPPRVPRPFPVRP | 95 |
| 318 | RRRTRHVVPRPLPVRPPPRVPRPFPLRP | 93 |
| 319 | RRRPPRVPRPFPVRPPPRVPRPIPFVHNCSRTKTHLRRGSE | 93 |

Example 5

Determination of the MIC, MBC and MEC of Selected Peptides

To verify the antimicrobial potency of the peptides identified and described in Examples 1-4, the Minimal Inhibitory Concentration (MIC), Minimal Bactericidal Concentration (MBC) and Minimal Effective Concentration (MEC) of three structurally different peptides were determined against a range of microorganisms.

The following three peptides were selected for chemical synthesis and determination of antimicrobial potency:

PR-1 (RRR-PRPV-PRPF-PRPV-PRPL-PRPF-PRPF) (SEQ ID NO: 61)

PR-2 (RRR-PFRP-PFRP-PFRP-PVRP-PVRP-PFRP) (SEQ ID NO: 79)

PR-3 (RRR-PPRL-PRPF-PVRP-PPRF-PRPF-PLRP) (SEQ ID NO: 239)

The tested microorganisms included *E. coli* (ATCC 10536), *S. carnosus*, *S. simulans*, *M. luteus* (ATCC 9341), *B. subtilis* (ATCC 6633) and *S. cerevisiae* (ATCC 9763).

The MIC and MBC determinations were carried out in accordance to the NCCLS protocol with the minor modification that the peptide was dissolved in 0.01% acetic acid and 0.1% BSA to avoid precipitation at high concentrations and minimize peptide binding to plastic The MEC determinations were done according to Steinberg and Lehrer (Methods in Biology, Vol. 78: Antibacterial Peptide Protocols) in a radial diffusion assay setup. The MEC protocol circumvents some of the problems associated testing antimicrobial peptides with the NCCLS protocol and provides a very sensitive test setup. The results are shown in Tables 6-8.

TABLE 6

MIC determination (all values are micrograms/ml)

| Peptide | E. coli | S. carnosus | S. simulans | M. luteus | B. subtilis | S. cerevisiae |
|---|---|---|---|---|---|---|
| PR-1 | 128 | 4 | 16 | 64 | 16 | >128 |
| PR-2 | 64 | 16 | 64 | 64 | 64 | >128 |
| PR-3 | 64 | 4 | 8 | 64 | 4 | >128 |

TABLE 7

MBC determination (all values are micrograms/ml)

| Peptide | E. coli | S. carnosus | S. simulans | M. luteus | B. subtilis | S. cerevisiae |
|---|---|---|---|---|---|---|
| PR-1 | 128 | 64 | 64 | >128 | 64 | >128 |
| PR-2 | >128 | >128 | >128 | 64 | 64 | >128 |
| PR-3 | 128 | 64 | 32 | >128 | 64 | >128 |

TABLE 8

MEC determination (all values are micrograms/ml)

| Peptide | E. coli | S. carnosus | S. simulans | M. luteus | B. subtilis | S. cerevisiae |
|---|---|---|---|---|---|---|
| PR-1 | 3.0 | 1.7 | 0.8 | 0.4 | 2.4 | 32 |
| PR-2 | 3.0 | 2.0 | 1.1 | 0.5 | 3.6 | 32 |
| PR-3 | 3.0 | 1.8 | 0.9 | 0.8 | 2.0 | >128 |

It is evident that the three PR-rich peptides are broadly active against Gram-positive and Gram-negative organisms under defined conditions.

Example 6

Hemolytic Activity of PR-1, PR-2 and PR-3

The ability of the antimicrobial peptides to lyse human red blood cells (hRBC) was analyzed. The Red Blood Cell Test assay provides a simple test system that assesses the membranolytic activity of test materials. It is suitable as a screening assay for hemolytic properties. Hemoglobin release is a useful endpoint of cell membrane integrity. Released hemoglobin is detected by measuring absorbance at 540 nm. Normally, the concentration resulting in 50% hemolysis relative to a totally lysed sample (HL50) would be calculated; however due to the low hemolytic activity of the tested peptides, this was not done in this Example. An 8% RBC suspension (12 days old) was used in the present test setup.

Table 9 shows the individual hemolysis values relative to a 100% lysed sample.

TABLE 9

Hemolysis values.

| Peptide concentration (micrograms/ml) | Hemolysis (%) | | |
|---|---|---|---|
| | PR-1 | PR-2 | PR-3 |
| 0 | 15 | 15 | 15 |
| 47 | 16 | 16 | 19 |
| 94 | 16 | 16 | 16 |
| 188 | 16 | 17 | 16 |
| 375 | 17 | 17 | 18 |

Since the peptides were dissolved in 0.01% acetic acid, vehicle control of the 0.01% acetic acid was included. PBS with 25%, 10%, and 5% 0.01% acetic acid was included on both plates. No hemolytic reaction different from the background was observed at any of the tested concentrations.

To verify that a dose/response effect exists, the hemolytic activity of SDS was also tested.

TABLE 10

SDS dose/response values.

| SDS concentration (micrograms/ml) | Hemolysis (%) |
|---|---|
| 12.5 | 17 |
| 25 | 26 |
| 50 | 68 |
| 100 | 88 |

The three tested peptide variants, PR-1, PR-2 and PR-3, do not show hemolytic properties significantly different from the background level, under the conditions of the assay.

The level of spontaneous hemolysis is high in this assay, probably due to the age of the red blood cells (12 days). The relatively high level of spontaneous hemolysis does not interfere with the conclusion that the three peptides are non-hemolytic at the concentrations tested.

The invention claimed is:
1. An isolated polypeptide having antimicrobial activity, having the amino acid sequence (SEQ ID NO: 354):

```
Xaa Xaa Xaa Pro Pro Xaa Xaa Pro Arg Xaa Xaa Pro Xaa
1           5                   10

Xaa Pro Pro Pro Xaa Xaa Pro Arg Xaa Xaa Pro Xaa Xaa
    15              20                  25

Pro
``` wherein
(a) Xaa Xaa Xaa at positions 1-3 is absent or is Arg-Xaa-Arg wherein Xaa at position 2 is Phe, Ile, Leu, Arg, or Val;
(b) Xaa Xaa at positions 6-7 is selected from the group consisting of
Arg-Phe,
Phe-Arg,
Arg-Leu,
Leu-Arg,
Arg-Val,
Val-Arg,
Arg-Ile, and
Ile-Arg,
(c) Xaa Xaa at positions 10-11 is selected from the group consisting of
Phe-Pro,
Pro-Phe,
Leu-Pro,
Pro-Leu,
Val-Pro,
Pro-Val,
Ile-Pro, and
Pro-Ile.
(d) Xaa Xaa at positions 13-14 is selected from the group consisting of
Arg-Phe,
Phe-Arg,
Arg-Leu,
Leu-Arg,
Arg-Val,
Val-Arg,
Arg-Ile, and
Ile-Arg,
(e) Xaa Xaa at positions 18-19 is selected from the group consisting of
Arg-Phe,
Phe-Arg,
Arg-Leu,
Leu-Arg,
Arg-Val,
Val-Arg,
Arg-Ile, and
Ile-Arg,
(f) Xaa Xaa at positions 22-23 is selected from the group consisting of
Phe-Pro,
Pro-Phe,
Leu-Pro,
Pro-Leu,
Val-Pro,
Pro-Val,
Ile-Pro, and
Pro-Ile, (g) Xaa Xaa at positions 25-26 is selected from the group consisting of
Arg-Phe,
Phe-Arg,
Arg-Leu,
Leu-Arg,
Arg-Val,
Val-Arg,
Arg-Ile, and
Ile-Arg.

2. The polypeptide of claim 1, wherein Xaa Xaa Xaa at positions 1-3 is Arg-Xaa-Arg wherein Xaa at position 2 is Phe, Ile, Leu, Arg, or Val.
3. The polypeptide of claim 2, wherein Xaa at position 2 is Arg.
4. The polypeptide of claim 1, which has an amino acid sequence of

```
                                            (SEQ ID NO:239)
Arg Arg Arg Pro Pro Arg Leu Pro Arg Pro Phe Pro Val
1           5                   10

Arg Pro Pro Pro Arg Phe Pro Arg Pro Phe Pro Leu Arg
    15              20                  25

Pro.
```

5. The polypeptide of claim 1, which has an amino acid sequence selected from the group consisting of:

```
                                            (SEQ ID NO:207)
Arg Arg Arg Pro Pro Arg Phe Pro Arg Pro Phe Pro Ile
1           5                   10

Arg Pro Pro Pro Arg Phe Pro Arg Pro Ile Pro Phe Arg
    15              20                  25

Pro,
```

```
                                            (SEQ ID NO:208)
Arg Arg Arg Pro Pro Arg Phe Pro Arg Pro Phe Pro Val
1           5                   10

Arg Pro Pro Pro Arg Phe Pro Arg Pro Ile Pro Val Arg
    15              20                  25

Pro,
```

```
                                            (SEQ ID NO:209)
Arg Arg Arg Pro Pro Arg Ile Pro Arg Pro Phe Pro Ile
1           5                   10

Arg Pro Pro Pro Arg Phe Pro Arg Pro Ile Pro Phe Arg
    15              20                  25

Pro,
```

```
                                            (SEQ ID NO:210)
Arg Arg Arg Pro Pro Arg Ile Pro Arg Pro Ile Pro Val
1           5                   10

Arg Pro Pro Pro Arg Ile Pro Arg Pro Ile Pro Phe Arg
    15              20                  25

Pro,
```

```
                                            (SEQ ID NO:211)
Arg Arg Arg Pro Pro Arg Leu Pro Arg Pro Phe Pro Phe
1           5                   10

Arg Pro Pro Pro Arg Phe Pro Arg Pro Ile Pro Phe Arg
    15              20                  25

Pro,
```

```
                                           (SEQ ID NO:212)
Arg Arg Arg Pro Pro Arg Leu Pro Arg Pro Phe Pro Phe
 1               5                  10

Arg Pro Pro Pro Arg Phe Pro Arg Pro Val Pro Ile Arg
        15                  20                  25

Pro, (SEQ ID NO:213)
Arg Arg Arg Pro Pro Arg Leu Pro Arg Pro Phe Pro Phe
 1               5                  10

Arg Pro Pro Pro Arg Leu Pro Arg Pro Phe Pro Ile Arg
        15                  20                  25

Pro, (SEQ ID NO:214)
Arg Arg Arg Pro Pro Arg Leu Pro Arg Pro Phe Pro Phe
 1               5                  10

Arg Pro Pro Pro Arg Leu Pro Arg Pro Ile Pro Leu Arg
        15                  20                  25

Pro, and (SEQ ID NO:217)
Arg Arg Arg Pro Pro Arg Leu Pro Arg Pro Phe Pro Phe
 1               5                  10

Arg Pro Pro Pro Arg Val Pro Arg Pro Phe Pro Leu Arg
        15                  20                  25

Pro.

6. The polypeptide of claim 1, which has an amino acid sequence selected from the group consisting of:

(SEQ ID NO:218)
Arg Arg Arg Pro Pro Arg Leu Pro Arg Pro Phe Pro Phe
 1               5                  10

Arg Pro Pro Pro Arg Val Pro Arg Pro Ile Pro Val Arg
        15                  20                  25

Pro, (SEQ ID NO:219)
Arg Arg Arg Pro Pro Arg Leu Pro Arg Pro Phe Pro Phe
 1               5                  10

Arg Pro Pro Pro Arg Val Pro Arg Pro Leu Pro Phe Arg
        15                  20                  25

Pro, (SEQ ID NO:220)
Arg Arg Arg Pro Pro Arg Leu Pro Arg Pro Phe Pro Ile
 1               5                  10

Arg Pro Pro Pro Arg Phe Pro Arg Pro Phe Pro Val Arg
        15                  20                  25

Pro, (SEQ ID NO:221)
Arg Arg Arg Pro Pro Arg Leu Pro Arg Pro Phe Pro Ile
 1               5                  10

Arg Pro Pro Pro Arg Phe Pro Arg Pro Leu Pro Phe Arg
        15                  20                  25

Pro, (SEQ ID NO:222)
Arg Arg Arg Pro Pro Arg Leu Pro Arg Pro Phe Pro Ile
 1               5                  10

Arg Pro Pro Pro Arg Phe Pro Arg Pro Val Pro Leu Arg
        15                  20                  25

Pro, (SEQ ID NO:223)
Arg Arg Arg Pro Pro Arg Leu Pro Arg Pro Phe Pro Ile
 1               5                  10

Arg Pro Pro Pro Arg Leu Pro Arg Pro Leu Pro Phe Arg
        15                  20                  25

Pro, (SEQ ID NO:224)
Arg Arg Arg Pro Pro Arg Leu Pro Arg Pro Phe Pro Ile
 1               5                  10

Arg Pro Pro Pro Arg Val Pro Arg Pro Phe Pro Val Arg
        15                  20                  25

Pro, (SEQ ID NO:225)
Arg Arg Arg Pro Pro Arg Leu Pro Arg Pro Phe Pro Ile
 1               5                  10

Arg Pro Pro Pro Arg Val Pro Arg Pro Ile Pro Ile Arg
        15                  20                  25

Pro, (SEQ ID NO:226)
Arg Arg Arg Pro Pro Arg Leu Pro Arg Pro Phe Pro Ile
 1               5                  10

Arg Pro Pro Pro Arg Val Pro Arg Pro Ile Pro Val Arg
        15                  20                  25

Pro, and (SEQ ID NO:227)
Arg Arg Arg Pro Pro Arg Leu Pro Arg Pro Phe Pro Ile
 1               5                  10

Arg Pro Pro Pro Arg Val Pro Arg Pro Val Pro Ile Arg
        15                  20                  25

Pro.

7. The polypeptide of claim 1, which has an amino acid sequence selected from the group consisting of:

(SEQ ID NO:228)
Arg Arg Arg Pro Pro Arg Leu Pro Arg Pro Phe Pro Leu
 1               5                  10

Arg Pro Pro Pro Arg Phe Pro Arg Pro Phe Pro Ile Arg
        15                  20                  25

Pro, (SEQ ID NO:229)
Arg Arg Arg Pro Pro Arg Leu Pro Arg Pro Phe Pro Leu
 1               5                  10

Arg Pro Pro Pro Arg Phe Pro Arg Pro Phe Pro Leu Arg
        15                  20                  25

Pro,
```

-continued (SEQ ID NO:230)
Arg Arg Arg Pro Pro Arg Leu Pro Arg Pro Phe Pro Leu
1               5                   10
Arg Pro Pro Pro Arg Phe Pro Arg Pro Leu Pro Leu Arg
        15              20              25
Pro, (SEQ ID NO:231)
Arg Arg Arg Pro Pro Arg Leu Pro Arg Pro Phe Pro Leu
1               5                   10
Arg Pro Pro Pro Arg Leu Pro Arg Pro Phe Pro Phe Arg
        15              20              25
Pro, (SEQ ID NO:232)
Arg Arg Arg Pro Pro Arg Leu Pro Arg Pro Phe Pro Leu
1               5                   10
Arg Pro Pro Pro Arg Leu Pro Arg Pro Ile Pro Val Arg
        15              20              25
Pro, (SEQ ID NO:233)
Arg Arg Arg Pro Pro Arg Leu Pro Arg Pro Phe Pro Leu
1               5                   10
Arg Pro Pro Pro Arg Leu Pro Arg Pro Leu Pro Val Arg
        15              20              25
Pro, (SEQ ID NO:234)
Arg Arg Arg Pro Pro Arg Leu Pro Arg Pro Phe Pro Leu
1               5                   10
Arg Pro Pro Pro Arg Val Pro Arg Pro Leu Pro Ile Arg
        15              20              25
Pro, (SEQ ID NO:235)
Arg Arg Arg Pro Pro Arg Leu Pro Arg Pro Phe Pro Leu
1               5                   10
Arg Pro Pro Pro Arg Val Pro Arg Pro Val Pro Phe Arg
        15              20              25
Pro, (SEQ ID NO:236)
Arg Arg Arg Pro Pro Arg Leu Pro Arg Pro Phe Pro Leu
1               5                   10
Arg Pro Pro Pro Arg Val Pro Arg Pro Val Pro Phe Arg
        15              20              25
Pro, and (SEQ ID NO:237)
Arg Arg Arg Pro Pro Arg Leu Pro Arg Pro Phe Pro Leu
1               5                   10
Arg Pro Pro Pro Arg Val Pro Arg Pro Val Pro Val Arg
        15              20              25
Pro.

8. The polypeptide of claim 1, which has an amino acid sequence selected from the group consisting of:

(SEQ ID NO:238)
Arg Arg Arg Pro Pro Arg Leu Pro Arg Pro Phe Pro Val
1               5                   10
Arg Pro Pro Pro Arg Phe Pro Arg Pro Phe Pro Ile Arg
        15              20              25
Pro, (SEQ ID NO:240)
Arg Arg Arg Pro Pro Arg Leu Pro Arg Pro Phe Pro Val
1               5                   10
Arg Pro Pro Pro Arg Phe Pro Arg Pro Val Pro Phe Arg
        15              20              25
Pro, (SEQ ID NO:241)
Arg Arg Arg Pro Pro Arg Leu Pro Arg Pro Phe Pro Val
1               5                   10
Arg Pro Pro Pro Arg Ile Pro Arg Pro Ile Pro Phe Arg
        15              20              25
Pro, (SEQ ID NO:242)
Arg Arg Arg Pro Pro Arg Leu Pro Arg Pro Phe Pro Val
1               5                   10
Arg Pro Pro Pro Arg Leu Pro Arg Pro Val Pro Phe Arg
        15              20              25
Pro, (SEQ ID NO:243)
Arg Arg Arg Pro Pro Arg Leu Pro Arg Pro Phe Pro Val
1               5                   10
Arg Pro Pro Pro Arg Leu Pro Arg Pro Val Pro Phe Arg
        15              20              25
Pro, (SEQ ID NO:244)
Arg Arg Arg Pro Pro Arg Leu Pro Arg Pro Phe Pro Val
1               5                   10
Arg Pro Pro Pro Arg Leu Pro Arg Pro Val Pro Phe Arg
        15              20              25
Pro, (SEQ ID NO:245)
Arg Arg Arg Pro Pro Arg Leu Pro Arg Pro Phe Pro Val
1               5                   10
Arg Pro Pro Pro Arg Val Pro Arg Pro Phe Pro Val Arg
        15              20              25
Pro, (SEQ ID NO:246)
Arg Arg Arg Pro Pro Arg Leu Pro Arg Pro Phe Pro Val
1               5                   10
Arg Pro Pro Pro Arg Val Pro Arg Pro Phe Pro Val Arg
        15              20              25
Pro,

```
                                                (SEQ ID NO:247)
Arg Arg Arg Pro Pro Arg Leu Pro Arg Pro Phe Pro Val
 1               5                   10

Arg Pro Pro Pro Arg Val Pro Arg Pro Leu Pro Phe Arg
        15                  20                  25

Pro, and (SEQ ID NO:248)
Arg Arg Arg Pro Pro Arg Leu Pro Arg Pro Phe Pro Val
 1               5                   10

Arg Pro Pro Pro Arg Val Pro Arg Pro Val Pro Ile Arg
        15                  20                  25

Pro.
```

9. The polypeptide of claim 1, which has an amino acid sequence selected from the group consisting of:

```
                                                (SEQ ID NO:249)
Arg Arg Arg Pro Pro Arg Leu Pro Arg Pro Phe Pro Val
 1               5                   10

Arg Pro Pro Pro Arg Val Pro Arg Pro Val Pro Ile Arg
        15                  20                  25

Pro,
                                                (SEQ ID NO:250)
Arg Arg Arg Pro Pro Arg Leu Pro Arg Pro Ile Pro Phe
 1               5                   10

Arg Pro Pro Pro Arg Ile Pro Arg Pro Ile Pro Val Arg
        15                  20                  25

Pro,
                                                (SEQ ID NO:251)
Arg Arg Arg Pro Pro Arg Leu Pro Arg Pro Ile Pro Phe
 1               5                   10

Arg Pro Pro Pro Arg Ile Pro Arg Pro Leu Pro Phe Arg
        15                  20                  25

Pro,
                                                (SEQ ID NO:252)
Arg Arg Arg Pro Pro Arg Leu Pro Arg Pro Ile Pro Phe
 1               5                   10

Arg Pro Pro Pro Arg Ile Pro Arg Pro Val Pro Val Arg
        15                  20                  25

Pro,
                                                (SEQ ID NO:253)
Arg Arg Arg Pro Pro Arg Leu Pro Arg Pro Ile Pro Phe
 1               5                   10

Arg Pro Pro Pro Arg Leu Pro Arg Pro Ile Pro Ile Arg
        15                  20                  25

Pro,
                                                (SEQ ID NO:254)
Arg Arg Arg Pro Pro Arg Leu Pro Arg Pro Ile Pro Phe
 1               5                   10

Arg Pro Pro Pro Arg Val Pro Arg Pro Phe Pro Ile Arg
        15                  20                  25

Pro,
                                                (SEQ ID NO:255)
Arg Arg Arg Pro Pro Arg Leu Pro Arg Pro Ile Pro Ile
 1               5                   10

Arg Pro Pro Pro Arg Phe Pro Arg Pro Val Pro Phe Arg
        15                  20                  25

Pro,
                                                (SEQ ID NO:256)
Arg Arg Arg Pro Pro Arg Leu Pro Arg Pro Ile Pro Leu
 1               5                   10

Arg Pro Pro Pro Arg Val Pro Arg Pro Ile Pro Ile Arg
        15                  20                  25

Pro,
                                                (SEQ ID NO:257)
Arg Arg Arg Pro Pro Arg Leu Pro Arg Pro Ile Pro Val
 1               5                   10

Arg Pro Pro Pro Arg Phe Pro Arg Pro Ile Pro Phe Arg
        15                  20                  25

Pro, and
                                                (SEQ ID NO:258)
Arg Arg Arg Pro Pro Arg Leu Pro Arg Pro Ile Pro Val
 1               5                   10

Arg Pro Pro Pro Arg Phe Pro Arg Pro Ile Pro Phe Arg
        15                  20                  25

Pro.
```

10. The polypeptide of claim 1, which has an amino acid sequence selected from the group consisting of:

```
                                                (SEQ ID NO:259)
Arg Arg Arg Pro Pro Arg Leu Pro Arg Pro Ile Pro Val
 1               5                   10

Arg Pro Pro Pro Arg Phe Pro Arg Pro Ile Pro Val Arg
        15                  20                  25

Pro,
                                                (SEQ ID NO:260)
Arg Arg Arg Pro Pro Arg Leu Pro Arg Pro Ile Pro Val
 1               5                   10

Arg Pro Pro Pro Arg Ile Pro Arg Pro Ile Pro Val Arg
        15                  20                  25

Pro,
                                                (SEQ ID NO:261)
Arg Arg Arg Pro Pro Arg Leu Pro Arg Pro Ile Pro Val
 1               5                   10

Arg Pro Pro Pro Arg Ile Pro Arg Pro Val Pro Phe Arg
        15                  20                  25

Pro,
                                                (SEQ ID NO:262)
Arg Arg Arg Pro Pro Arg Leu Pro Arg Pro Ile Pro Val
 1               5                   10

Arg Pro Pro Pro Arg Leu Pro Arg Pro Val Pro Leu Arg
        15                  20                  25

Pro,
```

```
                                        (SEQ ID NO:263)
Arg Arg Arg Pro Pro Arg Leu Pro Arg Pro Ile Pro Val
1               5                   10

Arg Pro Pro Pro Arg Val Pro Arg Pro Ile Pro Leu Arg
        15              20              25
Pro,
                                        (SEQ ID NO:264)
Arg Arg Arg Pro Pro Arg Leu Pro Arg Pro Leu Pro Phe
1               5                   10

Arg Pro Pro Pro Arg Phe Pro Arg Pro Val Pro Val Arg
        15              20              25
Pro,
                                        (SEQ ID NO:265)
Arg Arg Arg Pro Pro Arg Leu Pro Arg Pro Leu Pro Phe
1               5                   10

Arg Pro Pro Pro Arg Leu Pro Arg Pro Phe Pro Val Arg
        15              20              25
Pro,
                                        (SEQ ID NO:266)
Arg Arg Arg Pro Pro Arg Leu Pro Arg Pro Leu Pro Phe
1               5                   10

Arg Pro Pro Pro Arg Leu Pro Arg Pro Val Pro Val Arg
        15              20              25
Pro,
                                        (SEQ ID NO:267)
Arg Arg Arg Pro Pro Arg Leu Pro Arg Pro Leu Pro Phe
1               5                   10

Arg Pro Pro Pro Arg Val Pro Arg Pro Phe Pro Ile Arg
        15              20              25
Pro, and
                                        (SEQ ID NO:268)
Arg Arg Arg Pro Pro Arg Leu Pro Arg Pro Leu Pro Phe
1               5                   10

Arg Pro Pro Pro Arg Val Pro Arg Pro Val Pro Leu Arg
        15              20              25
Pro.
```

11. The polypeptide of claim 1, which has an amino acid sequence selected from the group consisting of:

```
                                        (SEQ ID NO:269)
Arg Arg Arg Pro Pro Arg Leu Pro Arg Pro Leu Pro Phe
1               5                   10

Arg Pro Pro Pro Arg Val Pro Arg Pro Val Pro Val Arg
        15              20              25
Pro,
                                        (SEQ ID NO:270)
Arg Arg Arg Pro Pro Arg Leu Pro Arg Pro Leu Pro Phe
1               5                   10

Arg Pro Pro Pro Arg Val Pro Arg Pro Val Pro Val Arg
        15              20              25
Pro,
                                        (SEQ ID NO:271)
Arg Arg Arg Pro Pro Arg Leu Pro Arg Pro Leu Pro Phe
1               5                   10

Arg Pro Pro Pro Arg Val Pro Arg Pro Val Pro Val Arg
        15              20              25
Pro,
                                        (SEQ ID NO:272)
Arg Arg Arg Pro Pro Arg Leu Pro Arg Pro Leu Pro Ile
1               5                   10

Arg Pro Pro Pro Arg Phe Pro Arg Pro Ile Pro Val Arg
        15              20              25
Pro,
                                        (SEQ ID NO:273)
Arg Arg Arg Pro Pro Arg Leu Pro Arg Pro Leu Pro Ile
1               5                   10

Arg Pro Pro Pro Arg Phe Pro Arg Pro Val Pro Leu Arg
        15              20              25
Pro,
                                        (SEQ ID NO:274)
Arg Arg Arg Pro Pro Arg Leu Pro Arg Pro Leu Pro Ile
1               5                   10

Arg Pro Pro Pro Arg Phe Pro Arg Pro Val Pro Val Arg
        15              20              25
Pro,
                                        (SEQ ID NO:275)
Arg Arg Arg Pro Pro Arg Leu Pro Arg Pro Leu Pro Ile
1               5                   10

Arg Pro Pro Pro Arg Leu Pro Arg Pro Phe Pro Val Arg
        15              20              25
Pro,
                                        (SEQ ID NO:276)
Arg Arg Arg Pro Pro Arg Leu Pro Arg Pro Leu Pro Ile
1               5                   10

Arg Pro Pro Pro Arg Leu Pro Arg Pro Val Pro Val Arg
        15              20              25
Pro,
                                        (SEQ ID NO:277)
Arg Arg Arg Pro Pro Arg Leu Pro Arg Pro Leu Pro Ile
1               5                   10

Arg Pro Pro Pro Arg Val Pro Arg Pro Phe Pro Ile Arg
        15              20              25
Pro, and
                                        (SEQ ID NO:278)
Arg Arg Arg Pro Pro Arg Leu Pro Arg Pro Leu Pro Ile
1               5                   10

Arg Pro Pro Pro Arg Val Pro Arg Pro Leu Pro Phe Arg
        15              20              25
Pro.
```

12. The polypeptide of claim 1, which has an amino acid sequence selected from the group consisting of:

(SEQ ID NO:279)
Arg Arg Arg Pro Pro Arg Leu Pro Arg Pro Leu Pro Ile
1               5                   10
Arg Pro Pro Pro Arg Val Pro Arg Pro Leu Pro Leu Arg
       15              20              25
Pro, (SEQ ID NO:280)
Arg Arg Arg Pro Pro Arg Leu Pro Arg Pro Leu Pro Leu
1               5                   10
Arg Pro Pro Pro Arg Phe Pro Arg Pro Phe Pro Val Arg
       15              20              25
Pro, (SEQ ID NO:281)
Arg Arg Arg Pro Pro Arg Leu Pro Arg Pro Leu Pro Leu
1               5                   10
Arg Pro Pro Pro Arg Phe Pro Arg Pro Val Pro Leu Arg
       15              20              25
Pro, (SEQ ID NO:282)
Arg Arg Arg Pro Pro Arg Leu Pro Arg Pro Leu Pro Leu
1               5                   10
Arg Pro Pro Pro Arg Leu Pro His Pro Ile Pro Phe Arg
       15              20              25
Pro, (SEQ ID NO:283)
Arg Arg Arg Pro Pro Arg Leu Pro Arg Pro Leu Pro Val
1               5                   10
Arg Pro Pro Pro Arg Phe Pro Arg Pro Val Pro Phe Arg
       15              20              25
Pro, (SEQ ID NO:284)
Arg Arg Arg Pro Pro Arg Leu Pro Arg Pro Leu Pro Val
1               5                   10
Arg Pro Pro Pro Arg Phe Pro Arg Pro Val Pro Val Arg
       15              20              25
Pro, (SEQ ID NO:285)
Arg Arg Arg Pro Pro Arg Leu Pro Arg Pro Leu Pro Val
1               5                   10
Arg Pro Pro Pro Arg Ile Pro Arg Pro Phe Pro Val Arg
       15              20              25
Pro, (SEQ ID NO:286)
Arg Arg Arg Pro Pro Arg Leu Pro Arg Pro Leu Pro Val
1               5                   10
Arg Pro Pro Pro Arg Ile Pro Arg Pro Leu Pro Leu Arg
       15              20              25
Pro, (SEQ ID NO:287)
Arg Arg Arg Pro Pro Arg Leu Pro Arg Pro Leu Pro Val
1               5                   10
Arg Pro Pro Pro Arg Leu Pro Arg Pro Ile Pro Ile Arg
       15              20              25
Pro, and (SEQ ID NO:288)
Arg Arg Arg Pro Pro Arg Leu Pro Arg Pro Leu Pro Val
1               5                   10
Arg Pro Pro Pro Arg Val Pro Arg Pro Phe Pro Leu Arg
       15              20              25
Pro.

13. The polypeptide of claim 1, which has an amino acid sequence selected from the group consisting of:

(SEQ ID NO:289)
Arg Arg Arg Pro Pro Arg Leu Pro Arg Pro Leu Pro Val
1               5                   10
Arg Pro Pro Pro Arg Val Pro Arg Pro Phe Pro Val Arg
       15              20              25
Pro, (SEQ ID NO:290)
Arg Arg Arg Pro Pro Arg Leu Pro Arg Pro Leu Pro Val
1               5                   10
Arg Pro Pro Pro Arg Val Pro Arg Pro Leu Pro Leu Arg
       15              20              25
Pro, (SEQ ID NO:291)
Arg Arg Arg Pro Pro Arg Leu Pro Arg Pro Leu Pro Val
1               5                   10
Arg Pro Pro Pro Arg Val Pro Arg Pro Val Pro Phe Arg
       15              20              25
Pro, (SEQ ID NO:292)
Arg Arg Arg Pro Pro Arg Leu Pro Arg Pro Leu Pro Val
1               5                   10
Arg Pro Pro Pro Arg Val Pro Arg Pro Val Pro Phe Arg
       15              20              25
Pro, (SEQ ID NO:293)
Arg Arg Arg Pro Pro Arg Leu Pro Arg Pro Val Pro Phe
1               5                   10
Arg Pro Pro Pro Arg Phe Pro Arg Pro Phe Pro Ile Arg
       15              20              25
Pro, (SEQ ID NO:294)
Arg Arg Arg Pro Pro Arg Leu Pro Arg Pro Val Pro Phe
1               5                   10
Arg Pro Pro Pro Arg Phe Pro Arg Pro Val Pro Leu Arg
       15              20              25
Pro, (SEQ ID NO:296)
Arg Arg Arg Pro Pro Arg Leu Pro Arg Pro Val Pro Phe
1               5                   10

Arg Pro Pro Pro Arg Val Pro Arg Pro Ile Pro Phe Arg
        15                  20                  25

Pro, (SEQ ID NO:297)
Arg Arg Arg Pro Pro Arg Leu Pro Arg Pro Val Pro Phe
1               5                   10

Arg Pro Pro Pro Arg Val Pro Arg Pro Ile Pro Val Arg
        15                  20                  25

Pro, (SEQ ID NO:298)
Arg Arg Arg Pro Pro Arg Leu Pro Arg Pro Val Pro Phe
1               5                   10

Arg Pro Pro Pro Arg Val Pro Arg Pro Val Pro Leu Arg
        15                  20                  25

Pro, and (SEQ ID NO:299)
Arg Arg Arg Pro Pro Arg Leu Pro Arg Pro Val Pro Ile
1               5                   10

Arg Pro Pro Pro Arg Phe Pro Arg Pro Ile Pro Phe Arg
        15                  20                  25

Pro.

14. The polypeptide of claim 1, which has an amino acid sequence selected from the group consisting of:

(SEQ ID NO:300)
Arg Arg Arg Pro Pro Arg Leu Pro Arg Pro Val Pro Ile
1               5                   10

Arg Pro Pro Pro Arg Ile Pro Arg Pro Ile Pro Phe Arg
        15                  20                  25

Pro, (SEQ ID NO:301)
Arg Arg Arg Pro Pro Arg Leu Pro Arg Pro Val Pro Ile
1               5                   10

Arg Pro Pro Pro Arg Val Pro Arg Pro Val Pro Leu Arg
        15                  20                  25

Pro, (SEQ ID NO:302)
Arg Arg Arg Pro Pro Arg Leu Pro Arg Pro Val Pro Leu
1               5                   10

Arg Pro Pro Pro Arg Phe Pro Arg Pro Val Pro Val Arg
        15                  20                  25

Pro, (SEQ ID NO:303)
Arg Arg Arg Pro Pro Arg Leu Pro Arg Pro Val Pro Leu
1               5                   10

Arg Pro Pro Pro Arg Val Pro Arg Pro Leu Pro Ile Arg
        15                  20                  25

Pro, (SEQ ID NO:304)
Arg Arg Arg Pro Pro Arg Leu Pro Arg Pro Val Pro Val
1               5                   10

Arg Pro Pro Pro Arg Phe Pro Arg Pro Val Pro Ile Arg
        15                  20                  25

Pro, (SEQ ID NO:305)
Arg Arg Arg Pro Pro Arg Leu Pro Arg Pro Val Pro Val
1               5                   10

Arg Pro Pro Pro Arg Phe Pro Arg Pro Val Pro Val Arg
        15                  20                  25

Pro, (SEQ ID NO:306)
Arg Arg Arg Pro Pro Arg Leu Pro Arg Pro Val Pro Val
1               5                   10

Arg Pro Pro Pro Arg Phe Pro Arg Pro Val Pro Val Arg
        15                  20                  25

Pro, (SEQ ID NO:307)
Arg Arg Arg Pro Pro Arg Leu Pro Arg Pro Val Pro Val
1               5                   10

Arg Pro Pro Pro Arg Val Pro Arg Pro Val Pro Phe Arg
        15                  20                  25

Pro, (SEQ ID NO:308)
Arg Arg Arg Pro Pro Arg Leu Pro Arg Pro Val Pro Val
1               5                   10

Arg Pro Pro Pro Arg Val Pro Arg Pro Val Pro Val Arg
        15                  20                  25

Pro, (SEQ ID NO:309)
Arg Arg Arg Pro Pro Arg Val Pro Arg Pro Phe Pro Ile
1               5                   10

Arg Pro Pro Pro Arg Val Pro Arg Pro Ile Pro Phe Arg
        15                  20                  25

Pro, (SEQ ID NO:310)
Arg Arg Arg Pro Pro Arg Val Pro Arg Pro Phe Pro Ile
1               5                   10

Arg Pro Pro Pro Arg Val Pro Arg Pro Val Pro Val Arg
        15                  20                  25

Pro, (SEQ ID NO:311)
Arg Arg Arg Pro Pro Arg Val Pro Arg Pro Phe Pro Val
1               5                   10

Arg Pro Pro Pro Arg Phe Pro Arg Pro Val Pro Phe Arg
        15                  20                  25

Pro,

```
                                    (SEQ ID NO:312)
Arg Arg Arg Pro Pro Arg Val Pro Arg Pro Ile Pro Ile
1               5                   10

Arg Pro Pro Pro Arg Val Pro Arg Pro Val Pro Phe Arg
        15              20              25

Pro, (SEQ ID NO:313)
Arg Arg Arg Pro Pro Arg Val Pro Arg Pro Ile Pro Ile
1               5                   10

Arg Pro Pro Pro Arg Val Pro Arg Pro Val Pro Val Arg
        15              20              25

Pro, (SEQ ID NO:314)
Arg Arg Arg Pro Pro Arg Val Pro Arg Pro Leu Pro Phe
1               5                   10

Arg Pro Pro Pro Arg Phe Pro Arg Pro Ile Pro Phe Arg
        15              20              25

Pro, and (SEQ ID NO:315)
Arg Arg Arg Pro Pro Arg Val Pro Arg Pro Val Pro Val
1               5                   10

Arg Pro Pro Pro Arg Ile Pro Arg Pro Phe Pro Val Arg
        15              20              25

Pro.
```

15. A composition comprising a polypeptide of claim 1 and an additional biocidal agent.

16. A detergent composition comprising a surfactant and a polypeptide of claim 1.

17. An animal feed additive comprising
   (a) at least one polypeptide of claim 1, and
   (b) at least one fat soluble vitamin, and/or
   (c) at least one water soluble vitamin, and/or
   (d) at least one trace mineral, and/or
   (e) at least one macro mineral.

18. The animal feed additive of claim 17, which further comprises phytase, xylanase, galactanase, and/or beta-glucanase.

19. An animal feed composition having a crude protein content of 50 to 800 g/kg and comprising a polypeptide of claim 1.

20. A method for killing or inhibiting growth of microbial cells comprising contacting the microbial cells with a polypeptide of claim 1.

\* \* \* \* \*